United States Patent
Chow et al.

(10) Patent No.: US 10,471,081 B2
(45) Date of Patent: *Nov. 12, 2019

(54) METHODS FOR DECREASING THE INCIDENCE OF NECROTIZING ENTEROCOLITIS IN INFANTS, TODDLERS, OR CHILDREN USING HUMAN MILK OLIGOSACCHARIDES

(71) Applicant: ABBOTT LABORATORIES, Abbott Park, IL (US)

(72) Inventors: JoMay Chow, Westerville, OH (US); Steven R. Davis, Galena, OH (US); Rachael Buck, Gahanna, OH (US); Geralyn O. Duska-McEwen, Columbus, OH (US); Hawley K. Linke, Columbus, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/401,488

(22) Filed: Jan. 9, 2017

(65) Prior Publication Data

US 2017/0224714 A1  Aug. 10, 2017

Related U.S. Application Data

(62) Division of application No. 13/334,933, filed on Dec. 22, 2011, now Pat. No. 9,539,269.

(60) Provisional application No. 61/428,863, filed on Dec. 31, 2010, provisional application No. 61/428,868, filed on Dec. 31, 2010.

(51) Int. Cl.

| | | |
|---|---|---|
| A01N 43/04 | (2006.01) |
| A61K 31/715 | (2006.01) |
| A61K 31/702 | (2006.01) |
| A61K 31/716 | (2006.01) |
| A61K 45/06 | (2006.01) |
| A23L 33/00 | (2016.01) |
| A23L 33/10 | (2016.01) |
| A23L 33/12 | (2016.01) |
| A23L 33/19 | (2016.01) |
| A23L 33/135 | (2016.01) |
| A61K 9/107 | (2006.01) |
| A61K 31/733 | (2006.01) |
| A61K 35/20 | (2006.01) |
| A61K 35/744 | (2015.01) |
| A61K 35/745 | (2015.01) |
| A61K 35/747 | (2015.01) |
| A61K 36/48 | (2006.01) |
| A61K 38/01 | (2006.01) |
| A61K 35/00 | (2006.01) |

(52) U.S. Cl.
CPC ............ *A61K 31/702* (2013.01); *A23L 33/10* (2016.08); *A23L 33/12* (2016.08); *A23L 33/135* (2016.08); *A23L 33/19* (2016.08); *A23L 33/30* (2016.08); *A23L 33/40* (2016.08); *A61K 9/107* (2013.01); *A61K 31/716* (2013.01); *A61K 31/733* (2013.01); *A61K 35/20* (2013.01); *A61K 35/744* (2013.01); *A61K 35/745* (2013.01); *A61K 35/747* (2013.01); *A61K 36/48* (2013.01); *A61K 38/018* (2013.01); *A61K 45/06* (2013.01); *A23V 2002/00* (2013.01); *A61K 2035/11* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 4,762,822 A | 8/1988 | Ettinger | |
| 5,013,569 A * | 5/1991 | Rubin | A23C 9/1528 426/585 |
| 5,260,280 A | 11/1993 | Isoda et al. | |
| 5,834,423 A | 11/1998 | Koketsu et al. | |
| 5,906,982 A | 5/1999 | Prieto et al. | |
| 6,036,992 A | 3/2000 | Borror et al. | |
| 6,045,854 A | 4/2000 | Prieto et al. | |
| 6,080,787 A | 6/2000 | Carlson et al. | |
| 6,083,934 A | 7/2000 | Prieto et al. | |
| 6,146,670 A | 11/2000 | Prieto et al. | |
| 6,294,206 B1 | 9/2001 | Barrett-Reis | |
| 6,306,908 B1 | 10/2001 | Carlson et al. | |
| 6,365,218 B1 | 4/2002 | Borschel et al. | |
| 6,497,908 B1 | 12/2002 | Oshiro | |
| 6,576,251 B1 | 6/2003 | Stahl et al. | |

(Continued)

FOREIGN PATENT DOCUMENTS

| | | |
|---|---|---|
| CA | 2655665 | 12/2007 |
| CA | 2724766 | 3/2010 |

(Continued)

OTHER PUBLICATIONS

Ben World J. Gastroenterol (2008), vol. 14, pp. 6133-6139.*
Bode Nutrition Reviews (2009), vol. 67 (Suppl. 2), pp. S183-S191.*
Office Action in CA 2,842,672 dated Feb. 23, 2015.
Office Action in CA 2,842,672 dated Dec. 1, 2015.
Office Action in CA 2,842,672 dated Oct. 24, 2016.
Office Action in CA 2,822,660 dated Oct. 4, 2017.

(Continued)

*Primary Examiner* — Patrick T Lewis
(74) *Attorney, Agent, or Firm* — Calfee, Halter & Griswold LLP

(57) ABSTRACT

Disclosed are methods of reducing the incidence of necrotizing enterocolitis in an infant, toddler, or child using nutritional compositions including human milk oligosaccharides. The nutritional compositions including the human milk oligosaccharides are effective in reducing inflammation and the incidence of inflammatory diseases.

19 Claims, 22 Drawing Sheets

(56) References Cited

U.S. PATENT DOCUMENTS

| | | |
|---|---|---|
| 6,630,452 B2 | 10/2003 | Wilson |
| 7,090,862 B2 | 8/2006 | Barrett-Reis et al. |
| 7,090,879 B2 | 8/2006 | Albrecht et al. |
| 7,101,565 B2 | 9/2006 | Monte |
| 7,416,752 B2 | 8/2008 | Holub et al. |
| 8,425,930 B2 | 4/2013 | Barboza |
| 8,703,737 B2 | 4/2014 | Buck et al. |
| 8,802,650 B2 | 8/2014 | Buck et al. |
| 8,815,312 B2 | 8/2014 | Falk |
| 9,539,269 B2 | 1/2017 | Chow et al. |
| 2002/0019991 A1 | 2/2002 | Prieto et al. |
| 2003/0060445 A1 | 3/2003 | Wilson |
| 2004/0001817 A1 | 1/2004 | Giampapa |
| 2004/0202765 A1 | 10/2004 | McMahon et al. |
| 2004/0265462 A1 | 12/2004 | Carlson |
| 2005/0004070 A1 | 1/2005 | Stahl et al. |
| 2005/0070464 A1 | 3/2005 | Stahl et al. |
| 2005/0096295 A1 | 5/2005 | McMahon et al. |
| 2005/0208179 A1 | 9/2005 | Albrecht et al. |
| 2006/0039954 A1 | 2/2006 | Gierhart et al. |
| 2006/0088574 A1 | 4/2006 | Manning et al. |
| 2006/0246146 A1 | 11/2006 | McMahon et al. |
| 2006/0247153 A1 | 11/2006 | McMahon et al. |
| 2006/0270739 A1 | 11/2006 | Johnson et al. |
| 2007/0048405 A1 | 3/2007 | Dewille et al. |
| 2007/0058523 A1 | 3/2007 | Cho et al. |
| 2007/0098849 A1 | 5/2007 | Barrett-Reis et al. |
| 2007/0104700 A1 | 5/2007 | Garcia-Rodenas et al. |
| 2007/0104843 A1 | 5/2007 | Holst et al. |
| 2007/0173480 A1 | 7/2007 | Clandinin et al. |
| 2007/0255598 A1 | 11/2007 | McCarthy |
| 2008/0003329 A1 | 1/2008 | Rueda et al. |
| 2008/0003330 A1 | 1/2008 | Rueda et al. |
| 2008/0015166 A1 | 1/2008 | van Tol et al. |
| 2008/0057178 A1 | 3/2008 | Rueda et al. |
| 2008/0064635 A1 | 3/2008 | Rueda et al. |
| 2008/0089981 A1 | 4/2008 | Butler et al. |
| 2008/0125346 A1 | 5/2008 | Beerman et al. |
| 2009/0082249 A1 | 3/2009 | Garssen et al. |
| 2009/0082240 A1 | 4/2009 | Mills et al. |
| 2009/0092590 A1 | 4/2009 | Rangavajila et al. |
| 2009/0118229 A1 | 5/2009 | Zeina |
| 2009/0143301 A1 | 6/2009 | Olson et al. |
| 2009/0148545 A1 | 6/2009 | Falk |
| 2009/0191151 A1 | 7/2009 | Gai et al. |
| 2009/0305996 A1 | 12/2009 | Beerman et al. |
| 2010/0047393 A1 | 2/2010 | Glas et al. |
| 2010/0063002 A1 | 3/2010 | Stahl et al. |
| 2010/0233129 A1 | 9/2010 | Fichot et al. |
| 2010/0233198 A1 | 9/2010 | Fichot et al. |
| 2010/0254949 A1 | 10/2010 | Barboza |
| 2010/0260720 A1 | 10/2010 | Sprenger |
| 2010/0298244 A1 | 11/2010 | Yang et al. |
| 2010/0316619 A1 | 12/2010 | Wittke |
| 2012/0121561 A1 | 5/2012 | Mercenier et al. |
| 2012/0171166 A1 | 7/2012 | Chow et al. |
| 2012/0172319 A1 | 7/2012 | Chow et al. |
| 2012/0177691 A1 | 7/2012 | Stahl et al. |
| 2012/0294840 A1 | 11/2012 | Newburg et al. |
| 2013/0012472 A1 | 1/2013 | Newburg et al. |
| 2013/0059815 A1 | 3/2013 | Fournell et al. |
| 2014/0294789 A1 | 10/2014 | David et al. |
| 2014/0335065 A1 | 11/2014 | Davis et al. |

FOREIGN PATENT DOCUMENTS

| | | |
|---|---|---|
| CA | 2818505 | 11/2010 |
| CA | 2822660 | 7/2012 |
| CN | 101909615 A | 12/2010 |
| CN | 101909644 A | 12/2010 |
| CN | 103797021 | 5/2014 |
| EP | 1634599 | 3/2006 |
| EP | 1887017 | 2/2008 |
| EP | 2127661 | 2/2009 |
| EP | 2060257 | 5/2009 |
| EP | 2072052 | 6/2009 |
| EP | 1996031 | 7/2009 |
| EP | 2266582 | 12/2010 |
| EP | 2279672 | 2/2011 |
| EP | 2455387 | 5/2012 |
| JP | 8266255 | 10/1996 |
| JP | 10099048 | 4/1998 |
| JP | 10327804 | 12/1998 |
| WO | 1997048388 | 12/1997 |
| WO | 19980043494 | 10/1998 |
| WO | 2001042263 | 6/2001 |
| WO | 2001060346 | 8/2001 |
| WO | 2003003981 | 1/2003 |
| WO | 2003/082313 | 10/2003 |
| WO | 2004032639 | 4/2004 |
| WO | 2004047778 | 6/2004 |
| WO | 2004052121 | 6/2004 |
| WO | 2004112509 | 12/2004 |
| WO | 2005055944 | 6/2005 |
| WO | 2005067962 | 7/2005 |
| WO | 2005122790 | 12/2005 |
| WO | 2007046699 | 4/2007 |
| WO | 2007087468 | 8/2007 |
| WO | 2007/101675 | 9/2007 |
| WO | 2007101675 | 9/2007 |
| WO | 2007108690 | 9/2007 |
| WO | 2007114683 | 10/2007 |
| WO | 2007114696 | 10/2007 |
| WO | 2007136428 | 11/2007 |
| WO | 2008016306 | 2/2008 |
| WO | 2008033520 | 3/2008 |
| WO | 2008056983 | 5/2008 |
| WO | 2008108651 | 9/2008 |
| WO | 2008127104 | 10/2008 |
| WO | 2008139984 | 11/2008 |
| WO | 2008153391 | 12/2008 |
| WO | 2009033011 | 3/2009 |
| WO | 2009059996 | 5/2009 |
| WO | 2009067000 | 5/2009 |
| WO | 2009077352 | 6/2009 |
| WO | 2009102193 | 8/2009 |
| WO | 20090113861 | 9/2009 |
| WO | 2010003803 | 1/2010 |
| WO | 2010023178 | 3/2010 |
| WO | 2010065652 | 6/2010 |
| WO | 20100070104 | 6/2010 |
| WO | 20100115934 | 10/2010 |
| WO | 2010142504 | 12/2010 |
| WO | 2011005681 | 1/2011 |
| WO | 2011008087 | 1/2011 |
| WO | 2011012655 | 2/2011 |
| WO | 2011014468 | 2/2011 |
| WO | 2011090926 | 7/2011 |
| WO | 201196809 | 8/2011 |
| WO | 2011136636 | 11/2011 |
| WO | 2011136647 | 11/2011 |
| WO | 2012009315 | 1/2012 |
| WO | 2012069415 | 5/2012 |
| WO | 2012/076323 | 6/2012 |
| WO | 2012076322 | 6/2012 |
| WO | 2012092153 | 7/2012 |
| WO | 2012092155 | 7/2012 |
| WO | 2012092156 | 7/2012 |
| WO | 2012092157 | 7/2012 |
| WO | 2012092158 | 7/2012 |
| WO | 2012092159 | 7/2012 |
| WO | 2012092160 | 7/2012 |
| WO | 2013016111 | 1/2013 |
| WO | 2013032674 | 7/2013 |
| WO | 2013185780 | 12/2013 |

OTHER PUBLICATIONS

First Office Action in CN 201280046188.2 dated Feb. 17, 2015.
Second Office Action in CN 201280046188.2 dated Nov. 9, 2015.
Decision of Rejection in CN 201280046188.2 dated Jun. 8, 2016.
Notice of Reexamination in CN 201280046188.2 dated Mar. 13, 2017.

(56) References Cited

OTHER PUBLICATIONS

First Office Action in CN 201180067021.x dated Aug. 15, 2014.
Second Office Action in CN 201180067021.x dated Jun. 26, 2015.
Third Office Action in CN 201180067021.x dated Jan. 8, 2016.
Notification of Grant of Patent in CN 201180068703.2 dated Jul. 15, 2015.
First Office Action in CN 201280051863.0 dated Mar. 27, 2015.
Second Office Action in CN 201280051863.0 dated Nov. 4, 2015.
Third Office Action in CN 201280051863.0 dated Apr. 5, 2016.
Fourth Office Action in CN 201280051863.0 dated Dec. 15, 2016.
Fifth Office Action in CN 201280051863.0 dated Jul. 4, 2017.
Rule 161/162 Communication for EP Application No. 11811618.5 dated Aug. 7, 2013.
Communication for EP Application No. 11811618.5 dated Jul. 18, 2016.
Office Action in EP Application No. 11811266.3 dated Aug. 18, 2014.
Rule 161/162 Communication for EP Application No. 12741201.3 dated Feb. 28, 2014.
Communication for EP Application No. 12741201.3 dated Mar. 16, 2016.
Rule 161/162 Communication for EP Application No. 12766344.1 dated Apr. 4, 2014.
Exam Report for EP Application No. 12766344.1 dated Jan. 5, 2015.
Office Action for EP Application No. 12766344.1 dated Jan. 27, 2015.
Office Action for EP Application No. 12741201.3 dated Jan. 12, 2015.
Exam Report for ID Application No. P00201400846 dated Jun. 26, 2016.
Exam Report Stage II for ID Application No. P00201400846 dated Feb. 24, 2017.
Exam Report for ID Application No. P00 2014 01703 dated Jul. 8, 2016.
Exam Report Stage II for ID Application No. P00201401703 dated Mar. 9, 2017.
Exam Report for ID Application No. W00201302959 dated Jun. 8, 2017.
Office Action in MX/a/2013/007675 dated Oct. 30, 2015.
Second Office Action in MX/a/2013/007675 dated Jun. 14, 2016.
Third Office Action in MX/a/2013/007675 dated Mar. 7, 2017.
Fourth Office Action in MX/a/2013/007675 dated Jul. 27, 2017.
Office Action in MX/a/2014/000895 dated Mar. 7, 2017.
Substantive Examination Adverse Report in My Application No. PI2013002504 dated Jan. 31, 2017.
Substantive Examination Adverse Report in My Application No. PI2013002514 dated Jan. 31, 2017.
Substantive Examination Adverse Report in My Application No. PI2014000552 dated May 15, 2017.
First Examination Report in NZ 612,386 dated Dec. 18, 2013.
First Examination Report in NZ 611,807 dated Dec. 19, 2013.
First Examination Report in NZ 620,311 dated Nov. 3, 2014.
Further Examination Report in NZ 620,311 dated May 24, 2016.
First Examination Report in NZ 621,603 dated Nov. 28, 2014.
Substantive Examination Report in PH 1/2013/501382 dated Mar. 10, 2017.
Nritten Opinion in SG 2013050067 dated Aug. 12, 2014.
Written Opinion in SG 2013050067 dated May 28, 2015.
Final Examination Report in SG 2013050067 dated Feb. 19, 2016.
Search Report and Written Opinion in SG 201305083-6 dated Dec. 2, 2014.
Search Report and Written Opinion in SG 201305083-6 dated Jul. 31, 2015.
Buck, "Effect of Dietary Ribonudleotides on Infant Immmune Status. Part 2: Immune Cell Development," Pediatric Research, vol. 56(6), pp. 891-900 (2004).
Campbell, et al., "Selected indigestible oligosaccharides affect large bowel mass, cecal and fecal short-chain fatty acids, pH and microflora in rats," J. Nutr., vol. 127(1), pp. 130-136 (1997).

Castro, et al., "Cutting Edge: IFN-y Regulates the Induction and Expansion of IL-17-Producing CD4 T Cells during Mycobacterial Infection," Journal of Immunology, vol. 177(3), pp. 1416-1420 (2006).
Chaturvedi, "Fucosylated human milk oligosaccharides vary between individuals and over the course of lactation," Glycobiology, vol. 11 pp. 365-372 (2001).
Chen, et al., "Probiotics and prebiotics: role in clinical disease states," Adv. Pediatr., vol. 52, pp. 77-113 (2005).
Chen, L.R., "Introduction of Oligosaccharide," Department of Dietetics, MacKay Memorial Hospital, http://www.mmh.org.tw/nutrition/nutrroom/26 1oligo.htm [cited in English translation of Search Report in TW Application No. 100150004 dated Aug. 7, 2015.
Chierici et al., "Advances in the modulation of the microbial ecology of the gut in early infancy," Acta Paediatr. Suppl., vol. 91(441), pp. 56-63 (2003).
Cherbut et al., "The Prebiotic Characterisitics of Fructooliogosaccharides Are Necessary for Reduction of TNBS-Induced Colitis in Rats," J. of Nutr., vol. 133, pp. 21-27 (2003).
Chou, J.J., "Microorganisms, Foods, Probiotics, and Bifidus," Food and Life, Dec. 2004 http://203.145.193.110/NSC_INDEX/Journal/EJ0001/9312/9312-02.pdf.
Cinquin, et al., "Comparative effects of exopolysaccharides from lactic acid bacteria and fructo-oligosaccharides on infant gut microbiota tested in an in vitro colonic model with immobilized cells," FEMS Microbiol. Ecol., vol. 57(2), pp. 226-238 (2006).
Coppa et al., "Characterization of oligosaccharides in milk and feces of breast-fed infants by high-performance anion-exchange chromatography," Adv. Exp. Med. Biol., vol. 501, pp. 307-314 (2001).
Coppa et al., "The first prebiotics in humans: human milk oligosaccharides," J. Clin. Gastroenterol., vol. 38(Suppl.2), pp. S80-S83 (2004).
Cummings, et al., "Gastrointestinal effects of prebiotics," Br. J. Nutr., vol. 87(Suppl.2), pp. S145-S151 (2002).
Daddaoua, et al., "Goat Milk Oligosaccharides are Anti-Inflammatory in Rats with Hapten-Induced Colitis," Journal of Nutrition, vol. 136(3), pp. 672-676 (2006).
D'Souza et al., "Effects of Probiotics, Prebiotics, and Synbiotics on Messenger RNA Expression of Caveolin-1, NOS and Genes Regulating Oxidative Stress in the Terminal Illeum of Formula-Fed Neonatal Rats," Pediatric Research, vol. 67, pp. 526-531 (2010).
De la Fuente, et al., "Anti Oxidants as modulators of immune function," Immunology and Cell Biology, vol. 78, pp. 49-54 (2000).
De Vrese, et al., "Probiotics, prebiotics, and synbiotics," Adv. Biochem Eng. Biotechnol., vol. 111, pp. 1-66 (2008).
Douville, et al., "Human metapneumovirus elicits weak IFN-g memory responses compared with RSV," J. of Immun., vol. 176, pp. 5848-5855 (2006).
Edwards, et al., "Dietary fibre in infancy and childhood," Proc. Nutr. Soc., vol. 62(1), pp. 17-23 (2003).
Edwards et al., "Intestinal flora during the first months of life: new perspectives," Br. J. Nutr., vol. 88 (Suppl. 1), pp. S11-S18 (2002).
Eiwegger et al., "Human milk-derived oligosaccharides and plant-derived oligosaccharides stimulate cytokine production of cord blood t-cells in vitro," Pediatr. Res., vol. 56, pp. 536-540 (2004).
Eiwegger et al., "Prebiotic oligosaccharides: in vitro evidence for gastrointestinal epithelial transfer and immunomodulatory properties," Pediatric Allergy and Immunology, vol. 21(8), pp. 1179-1188 (2010).
Espinoza et al., "Efforts to emulate human milk oligosaccharides," Br. J. of Nutr., vol. 98 (Suppl. 1), pp. S74-S79 (2007).
Euler, et al., "Prebiotic effect on fructo-oligosaccharide supplemented term infant formula at two concentrations compared with unsupplemented formula and human milk," J. Pediatr. Gastroenterol. Nutr., vol. 40, pp. 157-164 (2005).
Fanaro et al., "Acidic oligosaccharides from pectin hydrolysate as new component for infant formulae: effect on intestinal flora, stool characteristics, and Ph," J. Pediatr. Gastroenterol. Nutr., vol. 41(2), pp. 186-190 (2005).
Fanaro et al., "Galacto-oligosaccharides and long-chain fructo-oligosaccharides as prebiotics in infant formulas: a review," Acta Paediatr. Suppl., vol. 94(449), pp. 22-26 (2005).

(56) References Cited

OTHER PUBLICATIONS

Fisberg et al., "Effect of Oral Nutritional Supplementation with or without Synbiotics on Sickness and Catch-up Growth in Preschool Children,"Intern. Pediatr., vol. 17(4), pp. 216-222 (2002).

Flickinger et al., "In vitro fermentation properties of selected frutoologasaccharide-containing vegetables and in vivo colonic microbial populations are affected by the diets of healthy human infants," J. Nutr., vol. 132(8), pp. 2188-2194 (2002).

Forsythe et al., "Mood and gut feelings," Brain Behav. Immun., vol. 24(1), pp. 1-8 (2009).

Forsythe et al., "Oral treatment with live Lactobacillus reuteri inhibits the allergic airway response in mice," Am. J. Resp. Crit. Care Med., vol. 175(6), pp. 561-569 (2007).

Forsythe et al., "Probiotics in neurology and psychiatry," In Therapeutic Microbiology: Probiotics and Related Strategies, Versalovic, J., Wilson M. ed., Washington D.C., ASM Press, pp. 285-298 (2008).

Friel, et al., "Milk from Mothers of Both Premature and Full-Term Infants Provide Better Antioxidant Protection than Does Infant Formula," Ped. Res., vol. 51(5), pp. 612-618 (2002).

Friesland Foods, Friso Gold Infant Formulas, available at http://www.friso.com.sg/products/frisogold2.php, last accessed Mar. 13, 2012.

German, et al., "Human milk oligosaccharides: evolution, structures and bioselectivity as substrates for intestinal bacteria," Nestle Nutr. Workshop Ser. Pediatr. Program, vol. 62, pp. 218-222 (2008).

Ghoddusi et al., "In vitro study on gas generation and prebiotic effects of some carbohydrates and their mixtures," Anaerobe, vol. 13, pp. 193-199 (2007).

Gibson, et al., "Dietary Modulation of the Human Colonic Microbiota: Introducing the Concept of Prebiotics," J. Nutr., vol. 125(6), pp. 1401-1412 (1995).

Gill et al., "Development and application of a liquid chromatographic method for analysis of nucleotides and nucleosides in milk and infant formulas," Intern. Dairy Journal, vol. 17(6), pp. 596-605 (2007).

Gill, et al., "Differential recruitment of dendritic cells and monocytes to respiratory mucosal sites in children with Influenze Virus or Respiratory Syncytial Virus Infection," Journal of Infectious Disease, vol. 198, pp. 1667-1676 (2008).

Gonzalez et al., "Differential transcriptional response of Bifidobacterium longum to human milk, formula milk, and galactooliogosaccharide," Appl. Environ. Microbiol., vol. 74(15), pp. 4686-4694 (2008).

Grabitske et al., "Gastrointestinal effects of low-digestible carbohydrates," Crit. Rev. Food Sci. Nutr., vol. 49(4), pp. 327-360 (2009).

Grazioso, "Antiinflammatory Effects of Human Milk on Chemically Induced Colitis in Rats," Pediatric Research, vol. 42(5), pp. 639-643 (1997).

Grulee et al., "Breast and artificial feeding: influence of morbidity and mortality of twenty thousand infants," J. Am. Med. Assoc., vol. 103, pp. 735-738 (1934).

Gunnarsson et al., "Sialic acid residues play a pivotal role in alpha 1-acid glycoprotein (AGP)-induced generation of reactive oxygen species in chemotactic peptide pre-activated neutrophil granulocytes," Inflammation Research, vol. 59(2), pp. 89-95 (2010).

Gutierrez et al., "Immune response to nucleotide-supplemented infant formulae: systematic review and meta-analysis," British J. of Nutr., (2007), 98 (Suppl. 1), S64-S67 (2007).

Hernot et al., "In vitro fermentation profiles, gas production rates, and microbiota modulation as affected by certain fructans, galactooligosaccharides, and polydextrose," J. Agric. Food Chem., vol. 57, pp. 1354-1361 (2009).

Hidaka, et al., "Effects of fructooligosaccharides on intestinal flora and human health," Bifidobacteria Microflora, vol. 5(1), pp. 37-50 (1986).

"Human Breast Milk," Wikipedia, last accessed Feb. 2, 2012.

Idota, et al., "Growth-promoting effects of N-Acetylneuraminic acid-containing substances on bifidobacterial," Biosci. Biotech. Biochem., vol. 58, pp. 1720-1722 (1994).

Issacs, "Human milk inactivates pathogens individually, additively, and synergistically," J. Nutr., vol. 135(5), pp. 1286-1288 (2005).

Jantscher-Krenn et al., "Human milk oligosaccharides and their potential benefits for the breast-fed neonate," Minerva Pediatr., vol. 64, pp. 83-99 (2012).

Schrezenmeir et al., "Benefits of oral supplementation with and without synbiotics in young children with acute bacterial infections," Clin. Pediatr., vol. 43(3), pp. 239-249 (2004).

Sela et al., "The genome sequence of Bifidobacterium longum subsp. Infantis reveals adaptations for milk utilization within the infant microbiome," Proc. Natl. Acad. Sci., USA, vol. 105(48), pp. 18964-18969 (2008).

Sela et al., "Nursing our microbiota: molecular linkages between bifidobacteria and milk oligosaccharides," Trends Microb., vol. 18(7), pp. 298-307 (2010).

Sherman et al., "Potential roles and clinical utitlity of prebiotics in newborns, infants, and children," Proceedings from a global prebiotic summit meeting, New York City, Jun. 27-28, 2008, J. Pediatr, vol. 155(5), pp. S61-S70 (2009).

Soitgiu et al., "Immunomodulation of fucosyl-lactose and lacto-N-fucopentaose on mononuclear cells from multiple sclerosis and healthy subjects," Inter. J. Biomediacl. Sci., vol. 2(2), pp. 114-120 (2006).

Soukup et al., "Role of monocytes and eosinophils in human RSV infection in vitro," Clinical Immunology, vol. 107, pp. 178-185 (2003).

Spurrell, et al., "Human airway epithelial cells produce IP-10 (CXCL 10) in vitro and in vivo upon rhinovirus infection," Am. J. Physiol. Lung Cell Mol. Physiol., vol. 289, pp. L85-L95 (2005).

Stevens, et al., "Glycan microarray analysis of the hemagglutinins from modern and pandemic influenza viruses reveals different receptor specificities," Journal of Molecular Biology, vol. 355, pp. 1143-1155 (2006).

Stevens et al., "Structure and receptor specificity of the Hemagglutinin from an H5N1 influenza virus," Science, vol. 312, pp. 404-410 (2006).

Stewart, et al., "Fructooliogosaccharides exhibit more rapid fermentation than long-chain inulin in an in vitro fermentation system," Nutr. Res., vol. 28, pp. 329-334 (2008).

Sumiyoshu W. et al., "Determination of each neutral oligosaccharide in the milk of Japanese women during the course of lactation," Br. J. Nutr. vol. 89, pp. 61-69 Mar. 9, 2003 [cited in Aug. 12, 2014 Written Opinion for SG 2013050067].

Sun, X., "Recent anti-influenza strategies in multivalent sialyloigosaccharides and sialylmimetics approaches," Current Medicinal Chemistry, vol. 14, pp. 2304-2313 (2007).

Suzuki et al., "Receptor specificities of human respiroviruses," J. of Virol., vol. 75(10), pp. 4604-4613 (2001).

Szylit, et al., "Physiological and pathphysiological effects of carbohydrate fermentation," World Rev. Nutr. Diet., vol. 74, pp. 88-122 (1993).

Teneberg, et al., "Inhibition of nonopsonic Helicobacter pylori-induced activation of human neutrophils by sialylated oligosaccharides," Glycobiology, vol. 10(11), pp. 1171-1181 (2000).

Thurl, et al., "Variation of human milk oligosaccharides in relation to milk groups and lactational periods," Br. J. of Nutr., vol. 104(9), pp. 1261-1271 (2010).

Thurl, et al., "Variation of netural oligosaccharides and lactose in human milk during the feeding," Zeitschrift fuer Emaehrungswissenschaft, Steinkopf Verlag, Darmstadt, DE, vol. 32 (41), pp. 262-269 (1993).

Thymann et al., "Formula-feeding reduces lactose digestive capacity in neonatal pigs," British J. of Nutrition, vol. 95, pp. 1075-1081 (2006).

Tijerina-Saenz, "Antioxidant capacity of human milk and its association with vitamins A and E and fatty acid composition," Acta Paediatrica, vol. 98(11), pp. 1793-1798 (2009).

Tsopmo et al., "Human Milk has Anti-Oxidant Properties to Protect Premature Infants," Current Pediatric Reviews, vol. 3, pp. 45-51 (2007).

Urashima, Tadasu et al., "Biological significance of human milk oligosaccharides," Milk Science, vol. 56(4), pp. 155-176 (2008).

(56) References Cited

OTHER PUBLICATIONS

Vandenplas, Y., "Oligosaccharides in infant formula," Br. J. Nutr., vol. 87 (Suppl. 2), pp. S293-S296 (2002).
Varki, et al., "Biological roles of oligosaccharides: all of the theories are correct," Glycobiology, vol. 3(2), pp. 97-130 (1993).
Veereman, G., "Pediatric applications of inulin and oligofructose," J. Nutr., vol. 137(11 Suppl.), pp. 2585S-2589S (2007).
Veereman-Wauters, G., "Application of prebiotics in infant foods," Br. J. Nutr., vol. 93 (Suppl. 1), pp. S57-S60 (2005).
Vester Boler et al., "Carbohydrates blended with polydextrose lower gas production and short-chain fatty acid production in an in vitro system," Nutr. Res., vol. 29, pp. 631-639 (2009).
Videla et al., "Dietary inulin improves distal colitis induced by dextran sodium sulfate in the ratlnulin in Dextran Sodium Sulfate Colitis," Am. J. of Gastro., vol. 96, pp. 1486-1493 (2001).
Von Nicolai et al., "Partial purification and properties of neuraminidase from Bifidobacterium lactentis," Hoppe Seylers Z Physiol. Chem., vol. 362(2), pp. 153-162 (1981).
Vos et al., "Dietary supplementation of neutral and acidic oligosaccharides enhances Th 1-dependent vaccination responses in mice," Pediatr. Allergy Immunol., vol. 18(4), pp. 304-312, (2007).
Vos et al., "Immune-modulatory effects and potential working mechanisms of orally applied nondigestible carbohydrates," Critical Reviews in Immunology, vol. 27(2), pp. 97-140 (Jan. 2007).
Wada, et al., "Bifidobacterium bifidum lacto-N-biosidase, a critical enzyme for the degradation of human milk oligosaccharides with a type 1 structure," Appl. Environ. Microbiol., vol. 74(13), pp. 3996-4004 (2008).
Walker, A., "Milk and two oligosaccharides," Nat. Rev. Microbial., vol. 7(7), p. 483 (2009).
Wang et al., "Effects of the in vitro fermentation of oligofructose and inulin by bacteria growing in the human large intestine," J. Appl. Bacterial., vol. 75, pp. 373-380 (1993).
Wang, et al., "The role and potential of sialic acid in human nutrition," European Journal of Clinical Nutrition, vol. 57 (11), pp. 1351-1369 (2003).
Ward, Robert E. et al., "In vitro fermentability of human milk oligosaccharides by several strains of bifidobacteria," Molecular Nutrition & Food Research, vol. 51 (11), Nov. 2007, pp. 1398-1405.
Ward et al., "In vitro fermentation of breast milk oliogsaccharides by Bifidobacterium infantis and Lactobacillus gasseri," Appl. Environ. Microbiol., vol. 72, pp. 4497-4499 (2006).
Westerbeek et al., "Design of a randomised controlled trial on immune effects of acidic and neutral oligosaccharides in the nutrition of preterm infants: carrot study," BMC Pediatr, vol. 23, pp. 8-46 (2008).
Westerbeek et al., "The effect of enteral supplementation of a prebiotic mixture of non-human milk galacto-, fructo-, and acidic oligosaccharides on intestinal permeability in preterm infants," Br. J. Nut., vol. 105, pp. 268-274 (2011).
Whorwell, et al., "Efficacy of an Encapsulated Probiotic Bifidobacterium infantis 35624 in Women with Irritable Bowel Syndrome," Am. J. of Gastroenterology, vol. 101, pp. 1581-1590 (2006) [cited in May 4, 2015 OA in U.S. Appl. No. 13/335,341 (05744).
Wilson, M., "The gastrointestinal tract and its indigenous microbiota," Microbial Inhabitants of Humans: their ecology and role in health and disease, Cambridge University Press, pp. 283-287 (2005).
Wong, et al., "Colonic health: fermentation and short chain fatty acids," J. Clin. Gastroenterol., vol. 40(3), pp. 235-243 (2006).
Wu, et al., "Development of an Annotated Library of Neutral Human Milk Oligosaccharides," J. Proteome Res., vol. 9, pp. 4138-4151 (2010).
Xiao et al., "Distribution of in vitro fermentation ability of lacto-N-biose 1, a major building block of human milk oligosaccharides, in bifidobacterial strains," Appl. Environ. Microbiol., vol. 76(1), pp. 54-59 (2010).
Yamada, et al., "Lactotriaose-containing carbosilane dendrimers: Synthesis and lectin-binding activities," Bioorganic & Medicinal Chemistry, vol. 15(4), pp. 1606-1614 (2007).

Yamazaki et al., "Measurement of growth of bifidobacteria on inulofructosaccharides," Let. Appl. Microbiol., vol. 10, pp. 229-232 (1990).
Yau, et al., "Effect of nucleotides on diarrhea and immune responses in healthy term infants in Taiwan,", J. Pediatr. Gastro. Nutr., vol. 36(1), pp. 37-43 (2003).
Yoshida et al., "Role of N-3 polyunsaturated fatty acids and sialic acid in learning performance of rats,", J. of Neurochemistry, vol. 65(Suppl.), p. S173 (1995).
Yu, et al., "Improved extraction of PCT-quality community DNA from digesta and fecal samples," BioTechniques, vol. 36, pp. 808-812 (2004).
Yuhas et al., "Human milk fatty acid composition from nine countries varies most in DNA," Lipids, vol. 41(9), pp. 351-858 (2006).
Ziegler, et al., "Term infants fed formula supplemented with selected blends of prebiotics grow normally and have soft stools similar to those reported for breast-fed infants," J. Pediatr. Gastroenterol. Nutr., vol. 44, pp. 359-364 (2007).
Zivkovic et al., "Microbes and health sackler colloquium: Human mild glycobiome and its impact on the infant gastrointestinal microbiota," Proc. Natl. Acad. Sci., USA (2010).
Amendment from U.S. Appl. No. 14/234,166 dated Jan. 8, 2018.
Amendment from U.S. Appl. No. 14/238,822 dated Jan. 29, 2018.
Office Action in CA 2,822,219 dated Dec. 18, 2017.
Office Action in CA 2,842,672 dated May 29, 2017.
First Office Action in CN 201180068703.2 dated Nov. 4, 2014.
Office Action from Israeli Application No. 230892 dated Jan. 4, 2018.
Office Action in MX/a/2014/002491 dated Nov. 21, 2017.
Exam Report in SG 2014004907 dated Nov. 12, 2017.
Jantscher-Krenn et al., "The human milk oligosaccharide disialyllacto-N-tetraose prevents necrotising enterocolitis in neonatal rats," Gut, Oct. 2012 61(10), 1417-1425.
Jyonouchi et al., "Dietary ribonucleotides increase antigen-specific type 1 T-helper cells in the regional draining lymph nodes in young BALB/cJ mice," Nutrition, vol. 19(1), pp. 41-46 (2003).
Kanamori, et al., "Experience of long-term synbiotic therapy in seven short bowel patients with refractory enterocolitis," J. of Pediatric Surgery, vol. 39 (11), pp. 1686-1692 (2004).
Karimi et al., "Lactobacillus reuteri induced regulatory T cells protect against an allergic airway response in mice," Am. J. Resp. Crit. Care Med., vol. 179(3), pp. 186-193 (2009).
Kashyap, et al., "Growth Nutrient Retention and Metabolic Response of Low-birth-weight Infants fed Supplemented and Unsupplemented Preterm Human Milk," American Journal of Clinical Nutrition, American Society for Nutrition, U.S., vol. 52(2), pp. 254-262, (1990).
Kasson, et al., "Structural basis for influence of viral glycans on ligand binding by influenze hemagglutinin," Biophysical Journal, vol. 95(7), pp. L48-L50 (2008).
Kauth, et al., "Synergistically upregulated IL-10 production in cocultures of monocytes and T cells after stimulation with RSV," International Archives of Allergy and Immunology, vol. 142, pp. 116-126 (2007).
Kay, et al., "Mechanisms of T lymphocyte activation," Immunology Letters, vol. 29, pp. 51-54 (1991).
Khachik et al., "Identification, Quantification, and Relative Concentrations of Carotenoids and their Metabolites in Human Milk and Serum," Analytical Chemistry, American Chemical Society, US, vol. 69(10), pp. 1873-1881 (1997).
Kien, C.L., "Digestion, absorption, and fermentation of carbohydrates in the newborn," Clin. Perinatol., vol. 23(2), pp. 211-228 (1996).
Kitaoka et al., "Novel putative galactose operon involving lacto-N-biose phosphorylase in Bifidobacterium longum," Appl. Environ. Microbiol., vol. 71(6), pp. 3158-3162 (2005).
Kiyohara, et al., "An exo-{alpha}-sialidase from bifidobacteria involved in the degradation of sialyloliogosaccharides in human milk and intestinal glycoconjugates," Glycobiology, vol. 21(4), pp. 437-447 (2011).

(56) References Cited

OTHER PUBLICATIONS

Kiyohara et al., "Prebiotic effect of lacto-N-biose 1 on bifidobacterial growth," Biosci. Biotechnol. Biochem., vol. 73(5), pp. 1175-1179 (2009).
Knol, et al., "Colon microflora in infants fed formula and galacto- and fructo-oligosaccharides: more like breast-fed infants," J. Pediatr. Gastroenterol. Nutr., vol. 40(1), pp. 36-42 (2005).
Kobata, A. , "Structures and application of oligosaccharides in human milk," Proc. Jpn. Acad. Ser. B. Phys. Biol. Sci., vol. 86(7), pp. 731-747 (2010).
Kanamori, et al. "Experience of long-term synbiotic therapy in seven short bowel patients with refractory enterocololitis," Journal of Pediatric Surgery, vol. 39, No. 11 (2004) pp. 1686-1692.
Kulkarni et al., "Influence of dietary nucleotide restriction on bacterial sepsis and phagocytic cell function in mice," Arch. Surg., vol. 121(2), pp. 169-172 (1986).
Kunz, C., "Komplexe Oligosaccharide in der Saeuglingsernaehrung," Monatsschrift Fuer Kinderheilkunde, Springer Verlag, DE, vol. 146(1), pp. 49-56 (1998).
Kunz et al., "Biological functions of oligosaccharides in human milk," Acta paediatr., vol. 82(11), pp. 903-912 (1993).
Kunz et al., "Oligosaccharides in human milk: structural, functional, and metabolic aspects," Annu. Rev. Nutr., vol. 20, pp. 699-722 (2000).
Kunz, et al., "Potential anti-inflammatory and anti-infectious effects of Human Milk Oligosaccharides," from Bioactive Components of Milk, Springer, pp. 455-465 (2008).
Kunze, et al., "Lactobacillus reuteri enhances excitability of colonic AH neurons by inhibiting calcium dependent potassium channel opening," J. Cell Mol. Med., vol. 13(86), pp. 2261-2270 (2009).
Kuntz et al., "Oligosaccharides from human milk induce growth arrest via G2/M by influencing growth-related cell cycle genes in intestinal epithelial cells," Br. J. Nutr., vol. 101, pp. 1306-1315 (2009).
Kuntz, et al., "Oligosaccharides from human milk influence growth-related characteristics of intestinally transformed and non-transformed intestinal cells," Br. J. Nutr., vol. 99, pp. 462-471 (2008).
Kurokawa et al., "Comparative metagenomics revealed commonly enriched gene sets in human gut microbiomes," DNA Res., vol. 14, pp. 169-181 (2007).
Lara-Villoslada, "Oligosaccharides isolated from goat milk reduce intestinal inflammation in a rat model of dextran sodium sulfate-induced colitis," Clin. Nutr, vol. 25(3), pp. 477-488 (2006).
Leach et al., "Total potentially available nucleosides of human milk by stage of lactation," Am J. Clin. Nutr., vol. 61(6), pp. 1224-1230 (1995).
Lee et al., "Genomic insights into bifidobacteria," Microbiol. Mol. Biol. Rev., vol. 74(3), pp. 378-416 (2010).
Leforestier et al., "Effects of galacto-oligosaccharide ingestion on the mucosa-associated mucins and sucrose activity in the small intestine of mice," Eur J. Nutr. (Dec. 2009), 48(8), pp. 457-464.
Leyer, et al. "Probiotic Effects on Cold and Influenza-Like Symptom Incidence and Duration in Children," Pediatrics, vol. 124(2), pp. e172-e179 (2009).
Lin et al. "Necrotizing Enterocolitis: Recent Scientific Advances in Pathophysiology and Prevention," Seminars in Perinatology, WB Saunders, GB, vol. 32(2), pp. 70-82 (Mar. 14, 2008).
LoCascio, et al., "A versatile and scalable strategy for glycoprofiling bifidobacterial consumption of human milk Oligosaccharides," Microb. Biotechnol., vol. 2, pp. 333-342 (2009).
LoCascio et al., "Broad conservation of milk utilization genes in *Bifidobacterium longum* subsp. Infantix as revealed by comparative genomic hybridization," Appl. Environ. Microbiol., vol. 76(22), pp. 7373-7381 (2010).
LoCascio et al., "Glycoprofiling of bifidobacterial consumption of human milk oligosaccharides demonstrates strain specific, preferential consumption of small chain glycans secreted in early human lactation," J. Agric. Food Chem., vol. 55(22), pp. 8914-8919 (2007).

Ma et al., "Live Lactobacillus reuteri is essential for the inhibitory effect of tumour necrosis factor alpha-induced interleukin-8 expression," Infect. Immun., vol. 72, pp. 5308-5314 (2004).
Maaheimo, "Synthesis of a divalent sialyl Lewis X-O-glycan, a potent inhibitor of lymphocyte-endothelium adhesion. Evidence that multvalency enhances the saccharide binding to selectins," European Journal of Biochemistry, vol. 234, pp. 616-625 (1995).
Macfarlane et al., "Bacterial metabolism and health-related effects of galcto-oligosaccharides and other prebiotics," J. Appl. Microbiol., vol. 104(2), pp. 305-344 (2008).
MacIver, et al., "Glucose metabolism in lymphocytes is a regulated process with significant effects on immune cell function and survival," J. Leukoc. Biol., Vol. 84, pp. 949-957 (2008).
Magne et al., "Effects on faecal microbiota of dietary and acidic oligosaccharides in children during partial formula feeding," J. Pediatr. Gastroenterol. Nutr., vol. 46(5), pp. 580-588 (2008).
Malhotra, et al., "Isolation and characterisation of potential respiratory syncytial virus receptor(s) on epithelial cells," Microbes and Infection, vol. 5, pp. 123-133 (2003).
Marcobal, et al, "Consumption of human milk oligosaccharides by gut-related microbes," J. Agric. Food Chem., vol. 58, pp. 5334-5340 (2010).
Mariat, "The Firmicutes/Bacteroidetes ratio of the human microbiota changes with age," BMC Microbiol., vol. 9, p. 123 (2009).
Marlett et al., "American Dietetic Association, Position of the American Dietetic Association: health implications of dietary fiber," J. Am. Diet. Assoc., vol. 102(7), pp. 993-1000 (2002).
Martin-Sosa, et al., "Sialyloligosaccharides in human and bovine milk and in infant formulas: variations with the progression of lactation," J. Dairy Sci., vol. 86, pp. 52-59 (2003).
Martinez-Ferez, et al., "Goats' milk as a natural source of lactose-derived oligosaccharides: Isolation by membrane technology," Intern. Dairy J., vol. 16(2), pp. 173-181 (2006).
Masuko, et al., "Carbohydrate analysis by a phenol-sulfuric acid method in microplate format," Anal. Biochem., vol. 339, pp. 69-72 (2005).
McKeller et al., "Metabolism of fructo-oligosaccharides by *Bifidobacterium* spp.," Appl. Microbiol. Biotechnol., vol. 31, pp. 537-541 (1989).
McVeagh, et al., "Human milk oligosaccharides: only the breast," J. Paediatr. Child Health, vol. 33(4), pp. 281-286 (1997).
Meinzen-Derr, "Role of human milk in extremely low birth weight infants' risk of necrotizing enterocolitis or death," J. Perinatology, vol. 29, pp. 57-62 (2009).
Michalek, et al., "Cutting Edge: Distinct Glycolytic and Lipid Oxidative Metabolic Programs are Essential for Effector and Regulatory CD4+T Cell Subsets," Journal of Immunology, vol. 186, pp. 3299-3303 (2011).
Final Examination Report in SG 201305083-6 dated May 19, 2016.
Search Report and Written Opinion in SG 2014013478 dated Apr. 6, 2015.
Written Opinion in SG 2014013478 dated Dec. 22, 2015.
Search Report and Written Opinion in SG 201400490.7 dated Mar. 16, 2015.
Written Opinion in SG 2014004907 dated Apr. 12, 2016.
Written Opinion in SG 2014004907 dated Nov. 3, 2016.
Written Opinion in SG 2014004907 dated May 29, 2017.
Search Report in TW Application No. 101126368 dated May 2, 2016.
Office Action and Search Report in TW Application No. 100149846 dated Apr. 21, 2015.
Rejection of TW Application No. 100149846 dated Dec. 18, 2015.
Search Report in TW Application No. 100150004 dated Aug. 7, 2015.
Office Action in TW Application No. 100150004 dated Aug. 25, 2015.
Decision in TW Application No. 100150004 dated Jan. 28, 2016.
Office Action and Search Report in TW Application No. 101126368 dated May 4, 2016.
Decision on Rejection in TW Application No. 101126368 dated Dec. 28, 2016.
Office Action in VN Application No. 1-2013-01875 dated Oct. 21, 2013.

(56) References Cited

OTHER PUBLICATIONS

Second Office Action in VN Application No. 1-2013-01875 dated Jan. 8, 2014.
Office Action in VN 1-2013-02056 dated May 25, 2015.
Abbott's Gain with Immunity Ingredients, available at http://www.abbott.com/sg/family/products/children/gain.asp last accessed Mar. 13, 2012.
Abbott's Similac with Immunity Ingredients, available at http://www.abbott.com.sg/family/products/children/similac_follow_on_asp, last accessed Mar. 13, 2012.
Aggett et al., "Nondigestible carbohydrates in the diets of infants and young children: a commentary by the ESPGHAN Committee on Nutrition," J. Pediatr. Gastroenterol. Nutr., vol. 36(3), pp. 329-337 (2003).
Albermann et al., "Synthesis of the milk oligosaccharide 2'-fucosyllactose using recombinant bacterial enzymes," Carbohydrate Research, vol. 334 (2), pp. 97-103 (2001).
Armogida, "Identification and quantification of innate immune system mediators in human breast milk," Allergy and Asthma Proceedings, vol. 25(5), pp. 297-304 (2004).
Arslanoglu et al., "Early dietary intervention with a mixture of prebiotic oligosaccharides reduces the incidence of allergic manifestations and infections during the first two years of life," J. Nutr., vol. 138(6), pp. 1091-1095 (2008).
Arslanoglu, et al., "Early supplementation of prebiotic oligosaccharides protects formula-fed infants against infections luring the first 6 months of life," J. Nutr., vol. 137(11), pp. 2420-2424 (2007).
Asakuma et al., "Sial oligosaccharides of human colostrum: Changes in concentration during the first three days of lactation," Biosci. Biotechnol. Biochem., vol. 71(6), pp. 1447-1451 (2007).
Asakuma et al., "Variation of major neutral oligosaccharides levels in human colostrum", European Journal of Clinical Nutrition, vol. 62, pp. 488-494 Mar. 21, 2007.
Ashida, et al., "Two distinct alpha-L-fucosidases from Bifidobacterium bifidum are essential for the untilization of fucosylated milk oligosaccharides and glycoconjugates," Glybiology, vol. 19(9), pp. 1010-1017 (2009).
Bakker-Zierikzee et al., "Effects of infant formula containing a mixture of glacto- and fructo-oligosaccharides or viable Bifidobacterium animalis on the intestinal microflora during the first 4 months of life," Br. J. Nutr., vol. 94(5), pp. 783-790 (2005).
Bao, et al. "Simultaneous quantification of sialyloliogsaccharides from human milk by capillary electrophoresis," Anal. Biochem., vol. 370(2), pp. 206-214 (2007).
Barbara et al., "Interactions Between Commensal Bacteria and Gut Sensorimotor Function in Health and Disease," American Journal of Gastroenterology, pp. 2560-2568, 2005.
Barker, et al., "The colorimetric determination of lactic acid in biological materials," J. Bio. Chem., vol. 138, pp. 535-554 (1941).
Baarrangou et al., "Functional and comparative genomic analysis of an operon involved in fructooliogosaccharide utilization by Lactobaccillus acidophilus," Proceedings of the National Academy of Sciences of the United States of America, vol. 100(15), pp. 8957-8962 (2003).
Barrat et al., "Supplementation with galactooliogosaccharides and inulin increases bacterial translocation in artificially reared newborn rats," Peditr. Res., vol. 64(1), pp. 34-39 (2008).
Bezokorovainy, A., "Probiotics: determination of survival growth in the gut," Am. J. Clin. Nutr., vol. 73 (2 Suppl.), pp. 399S-405S (2001).
Bode et al., "Human milk-oligosaccharides: prebiotics and beyond," Nutr. Rev., vol. 67, pp. S183-S191 (2009).
Bode et al., "Human milk oligosaccharides prevent Nectrotizing Enterocolitis in neonatal rats," The FASEB Journal, vol. 24, p. 206.3, Apr. 2010.
Bode et al., "Human milk-oligosaccharides reduce platelet-neutrophil complex formation leading to a decrease in neutrophil beta-2 integrin expression," J. Leukocyte Bio., vol. 76, pp. 820-826 (2004).
Dr. Bode presentation, "Human Milk Oligosaccharides, Only the Breast," T. Denny Sanford Pediatrict Symposia, Apr. 24-25, 2009.
Bode et al., "Inhibition of monocyte, lymphocyte and neutrophil adhesion to endothelial cells by human milk oligosaccharides," Thrombosis and Haemostasis, vol. 92(6), pp. 1402-1410 (2004).
Bode, L., "Recent advances on structure, metabolism, and function of human milk oligosaccharides," J. Nutr., vol. 136, pp. 2127-2130 (2006).
Boehm et al., "Oligosaccharides from milk," J. Nutr., vol. 137(3 Suppl. 2), pp. 847S-849S (2007).
Boehm et al., "Prebiotic carbohydrates in human milk and formulas," Acta Paediatr. Suppl., vol. 94(449), pp. 18-21 (2005).
Boehm et al., "Prebiotic concept for infant nutrition," Acta Paediatr. Suppl., vol. 91(441), pp. 64-67 (2003).
Boehm et al., "Prebiotics in infant formulas," J. Clin. Gastroenterol., vol. 38(6 Suppl.), pp. S76-S79 (2004).
Boehm et al., "Supplementation of a bovine mild formula with an oligosaccharide mixture increases counts of faecal bifidobacteria in preterm infants," Arch. Dis. Child Fetal Neonatal Ed., vol. 86(3), pp. F178-F181 (2002).
Bouhnik et al., "Short-chain fructo-oligosaccharide administration dose-dependently increases fecal bificobacteria in healthy humans," J. Nutr., vol. 129, pp. 113-116 (1999).
Bourquin et al., "Vegetable fiber fermentation by human fecal bacteria: cell wall polysaccharide disappearance and short-chain fatty acid production during in vitro fermentation and water-holding capacity of unfermented residues," J. Nutr., vol. 123, pp. 860-869 (1993).
Bruzzese et al., "A formula containing galacto- and fructo-oligosaccharides prevents intestinal and extra-intestinal infections: an observational study," Clin. Nutr., vol. 28(2), pp. 156-161 (2009).
Bryant et al., "Cultural methods and some characteristics of some of the more numerous groups of bacteria in the bovine rumen," J. Dairy Sci., vol. 36, pp. 205-217 (1953).
Miñana, Vitoria, "Oligosacaridos en la leche humana," Acta Pediatr Esp. (2007), 65(3), pp. 129-133 (English abstract provided).
Miniello et al., "Prebiotics in infant milk formulas: new perspectives," Acta Paediatr. Suppl., vol. 91(441), pp. 68-76 (2003).
Miwa, et al., "Cooperation of beta-galactosidase and beta-N-acetylhexosaminidase from bifidobacteria in assimilation of human milk oligosaccharides with type 2 structure," Glycobiology, vol. 20(11), pp. 1402-1409 (2010).
Monaco et al., "The addition of polydextrose and galactooliogssacharide to formula does not affect barrier function or bacterial translocation in neonatal piglets," FASEB Journal, Meeting Abstract Supplement, vol. 23: LB479 (2009).
Moro et al., "Dosage-related bifidogenic effects of galacto- and fructooligosaccharides in formula-fed term infants," J. Pediatr. Gastroenterol. Nutr., vol. 34(3), pp. 291-295 (2002).
Moro et al., "Effects of a new mixture of prebiotics on faecal flora and stools in term infants," Acta Paediatr. Suppl., vol. 91(441), pp. 77-79 (2003).
Moro, et al., "Reproducing the bifidogenic effect of human milk in formula-fed infants: shy and how ?", Acta Paediatr. Suppl., vol. 94(449), pp. 14-17 (2005).
Morrow et al., "Human-Milk Glycans that Inhibit Pathogen Binding Protect Breast-feeding Infants against Infectious Diarrhea", J. of Nutrition, American Society for Nutrition, v. 135, No. 5 (May 1, 2005), pp. 1304-1307.
Morrow et al., "Human milk oligosaccharides are associated with protection against diarrhea in breast-fed infants," J. Pediatr., pp. 297-303 (2004).
Morrow et al., "Novel salivary and genetic biomarkers of risk for NEC or death in premature infants," FASEB, vol. 23 (Meeting Abstract Supplement), LB270 (2009).
Morrow et al., "Secretor phenotype and genotype are novel predictors of severe outcomes in premature infants," FASEB, vol. 24 (Meeting Abstract Supplement), p. 480.6 (2010).
Mountzouris et al., "Intestinal microflora of human infants and current trends for its nutritional modulation," Br. J. Nutr., vol. 87(5), pp. 405-420 (2002).

(56) References Cited

OTHER PUBLICATIONS

Mshvildadze et al., "Probiotics and prevention of necrotizing enterocolitis," Early Human Development, Shannon, IR, vol. 85(10), pp. S71-S74 (Oct. 1, 2009).
Nakhla et al., "Neutral oligosaccharide content of preterm human milk," Br. J. Nutr., vol. 82, pp. 361-367 (1999).
Nakamura et al., "Concentrations of sialyloligosaccharides in bovine colostrum and milk during the prepartum and early lactation," J. Dairy Sci., vol. 86, pp. 1315-1320 (2003).
Nakamura et al., "Molecular ecological analysis of fecal bacterial populations from term infants fed formula supplemented with selected blends of prebiotics," Appl. Environ. Microbiol., vol. 75, pp. 1121-1128 (2009).
Nakano et al., "Sialic acid in human milk," Acta paediatrica taiwanica, vol. 42(1), pp. 11-17 (2001).
Navarro, et al., "Influence of Dietary Nucleotides on Plasma Immunoglobulin Levels and Lymphocyte Subsets of Preterm Infants," Biofactors, vol. 10(1), pp. 67-76 (1999).
Newburg, DS, "Neonatal protection by an innate immune system of human milk consisting of oligosaccharides and glycans," J. Anim. Sci., vol. 87 (13 Suppl.), pp. 26-34 (2009).
Newburg, et al., "Human milk glycans protect infants against enteric pathogens," Annu. Rev. Nutr., vol. 25, pp. 37-58 (2005).
Newburg, et al., "Innate protection conferred by fucosylated oligosaccharides of human milk against diarrhea in breastfed infants," Glycobiology, vol. 14(3), pp. 253-263 (2004).
Newburg, et al., "Oligosaccharides in human milk and bacterial colonization," J. Pediatr. Gasterenterol. Nutr., vol. 30, pp. S8-S17 (2000).
Newburg, et al., "Protection of the neonate by the innate immune system of developing gut and of human milk," Ped. Res., vol. 61(1), pp. 2-8 (2007).
Nicholls et al., "Evolving complexities of influenza virus and its receptors," Trends in Microbiology, vol. 16(4), pp. 149-157 (2008).
Ninonuevo et al., "A strategy for annotating the human milk glycome," J. Agric. Food Chem., vol. 54, pp. 7471-7480 (2006).
Ninonuevo et al., "Mass spectrometric methods for analysis of oligosaccharides in human milk," Nutr. Rev., vol. 67 (Suppl. 2), pp. S216-S226 (2009).
Oliveros et al., "Prebioticos en formulas infantiles," An Pediatr., Monograph 4(1) 20-29 (Apr. 2006) (English translation provided).
Palmer et al., "Development of the human infant intestinal microbiota," Plos Biol., vol. 5, p.e. 177, pp. 1556-1573 (2007).
Parrett, et al., "In vitro fermentation of carbohydrate by breast fed and formula fed infants," Arch. Dis. Childhood, vol. 76, pp. 249-253 (1997).
Petschow et al., "Response of bifidobacterium species to growth promoters in human and cow milk," Pediatr. Res., vol. 29(2), pp. 208-213 (1991).
Pickering et al., "Modulation of the Immune System by Human Milk and Infant Formula Containing Nucleotides," Pediatrics, vol. 101(2), pp. 101(2), pp. 242-249 (1998).
Portelli, et al., "Effect of compounds with antibacterial activities in human milk on respiratory syncytial virus and cytomegalovirus in vitro," J. Med. Microbiol., vol. 47, pp. 1015-1018 (1998).
Probert et al., "Polydextrose, lactitol, and fructo-oligosaccharide fermentation by colonic bacteria in a three-stage continuous culture system," Appl. Environ. Microbiol., vol. 70(8), pp. 4505-4511 (2004).
Procter & Gamble Bifantis news release dated May 12, 2009 (4 pages).
Procter & Gamble "What is Bifantis 7" About Bifantis, Nov. 4, 2010 https://web.archive.org/web/20101104124637/http://www.bifantis.com.
Rinne, et al., "Similar bifidogenic effects of prebiotic-supplemented partially hydrolyzed infant formula and breastfeeding on infant gut microflora," Ferns Immunology and Medical Microbiology, Elsevier Science BV, Amsterdam, NL, vol. 43(1), pp. 59-65 (2005).
Rivero-Urgell et al., "Oligosaccharides: application in infant food," Early Human Dev., vol. 65(Suppl.), pp. S43-S52 (2001).
Robertfroid, M., "Prebiotics: the concepts revisited," J. Nutr., vol. 137, pp. 830S-837S (2007).
Rueda et al., "Influence of dietary compounds on intestinal immunity," Microbiol. Ecol. Health Diseases, vol. 2, pp. 146S-156S (2000).
Rumessen, JJ., "Fructose and related food carbohydrates. Sources, intake, absorption, and clinical implications," Scand. J. Gastroenterol., vol. 27(10), pp. 819-828 (1992).
Russ et al., "Post-weaning effects of milk and milk components on the intestinal mucosa in inflammation," Mutation Research, Elsevier, Amsterdam, vol. 690, Nos. 1-2, Aug. 7, 2010, pp. 64-70.
Rycroft et al. "A comparative in vitro evaluation of the fermentation properties of prebiotic oligosaccharides," J. Appl. Microbiol., vol. 91, pp. 878-887 (2001).
Saedisomeolia et al., "Lycopene enrichment of cultured epithelial cells decreases the inflammation induced by rhinovirus infection and lipopolysaccharide," J. Nutritional Biochemistry, vol. 20, pp. 577-585 (2009).
Salminenen et al., "Microbial-host interactions: selecting the right probiotics and prebiotics for infants," Nestle Nutr. Workshop Ser. Pediatr. Program, vol. 64, pp. 201-213 (2009).
Sangwan, et al., "Galactooliogosaccharides: novel components of designer foods," J. of Food Science, vol. 76(4), pp. R103-R111 (May 2011).
Schaefer et al., "Ammonia saturation constants for predominant species of rumen bacteria." J. Dairy Sci., vol. 63(8), pp. 1248-1263 (1980).
Schaller et al., "Effect of Dietary Ribonucleotides on Infant Immune Status. Part 1: Humoral Responses," Pediatric Research, vol. 56(6), pp. 883-890 (2004).
Schmelzle et al., "Randomized double-blind study of the nutritional efficacy and bifidogenicity of a new infant formula containing partially hydrolyzed protein, a high beta-palmitic acid level, and nondigestible oligosaccharides," J. Pediatr. Gastroenterol. Nutr., vol. 36(3), pp. 343-351 (2003).
Schnabl, et al., "Gangliosides protect bowel in an infant model of necrotizing enterocolitis by suppressing proinflammatory signals," J. Pediatr. Gastroenter. Nutr., vol. 49, pp. 382-392 (2009).
Scholtens et al., "Bifodogenic effects of solid weaning foods with added prebiotic oligosaccharides: a randomised controlled clinical trial," J. Pediatr. Gatroenterol. Nutr.,vol. 42(5), pp. 552-559 (2006).
International Search Report for PCT/US2011/043644 dated Feb. 17, 2012.
International Search Report and Written Opinion for PCT/US2011/067004 dated Jun. 11, 2012.
International Search Report and Written Opinion for PCT/US2011/067008 dated Mar. 29, 2012.
International Preliminary Report on Patentability for PCT/US2011/067012 dated Jul. 2, 2013.
International Search Report and Written Opinion for PCT/US2011/067012 dated May 24, 2012.
International Search Report and Written Opinion for PCT/US2011/067018 dated Mar. 27, 2012.
International Search Report and Written Opinion for PCT/US2011/067022 dated Jun. 11, 2012.
International Search Report and Written Opinion for PCT/US2011/067027 dated Jun. 11, 2012.
Invitation to Pay Additional Fees for PCT/US2011/067027 dated Mar. 27, 2012.
International Search Report and Written Opinion for PCT/US2011/067028 dated Mar. 27, 2012.
Invitation to Pay Additional Fees for PCT/2011/067031 dated May 29, 2012.
International Search Report and Written Opinion for PCT/US2012/047307 dated Nov. 14, 2012.
International Preliminary Report on Patentability for PCT/US2012/047307 dated Jan. 28, 2014.
International Search Report and Written Opinion for PCT/US2012/050569 dated Oct. 29, 2012.
International Preliminary Report on Patentability for PCT/US2012/050569 dated Mar. 4, 2014.
Non final rejection for U.S. Appl. No. 13/334,933 dated Jun. 27, 2014.

(56) References Cited

OTHER PUBLICATIONS

Amendment for U.S. Appl. No. 13/334,933 dated Sep. 29, 2014.
Office Action for U.S. Appl. No. 13/334,933 dated Oct. 27, 2014.
Response with RCE for U.S. Appl. No. 13/334,933 dated Jan. 27, 2015.
Office Action for U.S. Appl. No. 13/334,933 dated Mar. 23, 2015.
Amendment for U.S. Appl. No. 13/334,933 dated Jun. 23, 2015.
Final Office Action in U.S. Appl. No. 13/334,933 dated Aug. 10, 2015.
Amendment with RCE in U.S. Appl. No. 13/334,933 dated Nov. 10, 2015.
Office Action for U.S. Appl. No. 13/334,933 dated Jan. 22, 2016.
Amendment for U.S. Appl. No. 13/334,933 dated Jul. 22, 2016.
Office Action for U.S. Appl. No. 13/335,341 dated Nov. 5, 2014.
Response in U.S. Appl. No. 13/335,341 dated Feb. 3, 2015.
Final Office Action in U.S. Appl. No. 13/335,341 dated May 4, 2015.
Amendment with RCE in U.S. Appl. No. 13/335,341 dated Sep. 4, 2015.
Office Action for U.S. Appl. No. 13/335,341 dated Oct. 7, 2015.
Amendment for U.S. Appl. No. 13/335,341 dated Feb. 8, 2016.
Office Action for U.S. Appl. No. 13/335,341 dated Jun. 1, 2016.
Amendment for U.S. Appl. No. 13/335,341 dated Nov. 1, 2016.
Office Action for U.S. Appl. No. 13/335,341 dated Feb. 16, 2017.
Amendment for U.S. Appl. No. 13/335,341 dated Jun. 16, 2017.
Office Action for U.S. Appl. No. 13/335,341 dated Oct. 3, 2017.
Office Action for U.S. Appl. No. 14/234,166 dated Jun. 28, 2016.
Office Action for U.S. Appl. No. 14/234,166 dated Jan. 6, 2017.
Amendment for U.S. Appl. No. 14/234,166 dated Apr. 6, 2017.
Office Action for U.S. Appl. No. 14/234,166 dated Sep. 8, 2017.
Office Action for U.S. Appl. No. 14/238,822 dated Jun. 8, 2016.
Response for U.S. Appl. No. 14/238,822 dated Aug. 8, 2016.
Office Action for U.S. Appl. No. 14/238,822 dated Sep. 6, 2016.
Amendment in U.S. Appl. No. 14/238,822 dated Dec. 30, 2016.
Final Rejection for U.S. Appl. No. 14/238,822 dated Mar. 1, 2017.
Office Action for U.S. Appl. No. 14/238,822 dated Sep. 29, 2017.
Office Action in CA 2,846,603 dated Feb. 3, 2015.
Office Action in CA 2,846,603 dated Oct. 26, 2015.
Office Action in CA 2,846,603 dated Jun. 7, 2016.
Office Action in CA 2,846,603 dated Feb. 8, 2017.
Office Action for U.S. Appl. No. 14/234,166 dated Mar. 2, 2018.
Amendment for U.S. Appl. No. 13/335,341 dated Mar. 5, 2018.
Decision on Rejection in CN 201280051863.0 dated Feb. 14, 2018.
Substantive Examination Report in PH Jan. 2014-500185 dated Jan. 11, 2018.
Substantive Examination Report in PH Jan. 2013-501291 dated Jan. 26, 2018.
Substantive Examination Report in PH Jan. 2014-500394 dated Jan. 26, 2018.
Office Action in TW Application No. 101126368 dated Mar. 1, 2018.
Lawrence, RA, "Storage of Human Milk and the Influence of Procedures on Immunological Components of Human Milk," Acta Paediatr. Suppl., Aug. 1999, vol. 88, No. 430.
Ruiz-Palacios et al., "Campylobacter jejuni Binds Intestinal H(O) Antigen, and Fucosyloligosaccharides of Human Milk Inhibit Its Binding and Infection" J. Biol. Chem., 2003, 278(16), p. 14112-14120.
Sandin, et al., "Faecal Short Chain Fatty acid Pattern and Allergy in Early Childhood," Acta Paediatrica, vol. 98, No. 5, May 1, 2009, pp. 823-827.
Schanler et al., "Randomized Trial of Donor Human Milk Versus Preterm Formula as Substitutes for Mothers' Own Milk in the Feeding of Extremely Premature Infants," Pediatrics, 2005, 116(2), pp. 400-406.
Schmelzle et al., "Randomized double-blind study of the nutritional efficacy and bifidogenicity of a new infant formula containing partially hydrolyzed protein, a high beta-palmitic acid level, and nondigestible oligosaccharides," J. Pediatr. Gastroenterol. Nutr., vol. 36(3), pp. 343-351.
Shen et al., "High-Performance Capillary Electrophoresis of Sialylated Oligosaccharides of Human Milk," Anal. Biochem., (2000), 279, pp. 37-45.
Walker, A., "Breast Milk as the Gold Standard for Protective Nutrients," J. Pediatrics, 2010, 156, p. S3-S7, available online Jan. 21, 2010.
Wood, Enteric nervous system, serotonin, and the irritable bowel syndrome, Current Opinion in Gastroenterology, Jan. 2001, vol. 17, No. 1, pp. 91-97.
Response to Office Action for U.S. Appl. No. 14/234,166 dated Jun. 4, 2018.
Office Action from U.S. Appl. No. 14/238,822 dated Apr. 12, 2018.
Non Final Office Action for U.S. Appl. No. 13/334,904 dated Jun. 27, 2014.
Amendment in U.S. Appl. No. 13/334,904 dated Sep. 29, 2014.
Final Office Action for U.S. Appl. No. 13/334,904 dated Nov. 18, 2014.
Response with RCE for U.S. Appl. No. 13/334,904 dated Feb. 18, 2015.
Office Action in U.S. Appl. No. 13/334,904 dated Mar. 20, 2015.
Response with RCE for U.S. Appl. No. 13/334,904 dated Jun. 22, 2015.
Final Office Action for U.S. Appl. No. 13/334,904 dated Jul. 24, 2015.
Remarks for Pre-Appeal Review for U.S. Appl. No. 13/334,904 dated Oct. 23, 2015.
Notice of Panel Decision from Pre-Appeal Brief Review in U.S. Appl. No. 13/334,904 dated Nov. 23, 2015.
Office Action in U.S. Appl. No. 13/334,904 dated Dec. 10, 2015.
Amendment in U.S. Appl. No. 13/334,904 dated Jun. 10, 2016.
Final Office Action in U.S. Appl. No. 13/334,904 dated Jul. 11, 2016.
Non-Final Office Action in U.S. Appl. No. 13/334,904 dated Jan. 25, 2017.
Office Action from Canadian Patent Application No. 2,822,497 dated Dec. 11, 2017.
First Office Action for CN Application No. 201180068712.1 dated Sep. 15, 2014.
Second Office Action for CN Application No. 201180068712.1 dated May 29, 2015.
English translation of Third Office Action for CN Application No. 201180068712.1 dated Dec. 8, 2015.
English translation of Fourth Office Action for CN Application No. 201180068712.1 dated Jun. 27, 2016.
Fifth Office Action for CN Application No. 201180068712.1 dated Apr. 1, 2017.
Office Action from Chinese Application No. 201180068712.1 dated Oct. 23, 2017.
Office Action in EP Application No. 11813500.3 dated Aug. 8, 2014.
Office Action in EP Application No. 11813500.3 dated Apr. 20, 2016.
Office Action in EP Application No. 11813500.3 dated Jul. 31, 2017.
Extended Search Report for EP Application No. 18153075.9 dated Apr. 5, 2018.
Exam Report for ID Application No. P00201401703 dated Mar. 14, 2018.
Exam Report Stage II for ID Application No. W00201302799 dated Mar. 13, 2018.
Exam Report Stage II for ID Application No. W00201302800 dated Feb. 27, 2018.
Exam Report Stage I for ID Application No. W00201302694 dated Apr. 16, 2018.
Office Action in MX Application No. MX/A/2013/007681 received Jul. 22, 2014.
Second Office Action in MX Application No. MX/a/2013/007681 dated Nov. 9, 2015.
Third Office Action in MX Application No. MX/a/2013/007681 dated Jun. 26, 2015.
Kamm, "Why the enteric nervous system is important to clinicians", GUT, vol. 47, No. 9004, Dec. 1, 2000, pp. 8iv-9.
Kim,"Short-Chain Fatty Acids in Ulcerative Colitis," Nutrition Reviews, Jan. 1998, pp. 17-24.

(56) References Cited

OTHER PUBLICATIONS

Office Action in MY Application No. PI2013002501 dated Apr. 14, 2017.
Exam Report for NZ Application No. 612,504 Dec. 24, 2013.
Search Report and Written Opinion for SG 201305009-1 dated Nov. 4, 2014.
Written Opinion for SG 201305009-1 dated May 19, 2015.
Examination Report for SG 201305009-1 dated Jan. 12, 2016.
Nezami et al., "Enteric Nervous System in the Small Intestine: Pathophysiology and Clinical Implications," Current Gastroenterology Reports, vol. 12, No. 5, Oct. 20, 2010, pp. 358-365.
Bertino et al., "Effects of Holder Pasteurization on Human Milk Oligosaccharides," International J. Immunopathol. (2008), 21(2), pp. 381-385.
Chu et al., "Role of Se-Dependent Glutathoine Peroxidases in Gastrointestinal Inflammation and Cancer," Free Radical Biol. & Med., 2005, 36(12), p. 1481-1495.
Friel, et al., "Evidence of Oxidative Stress in Full-Term Healthy Infants, " Pediatric Research (2004), vol. 56, pp. 878-882.
Goedhart et al., "The Composition of Human Milk as a Model for the Design of Infant Formulas: Recent Findings and Possible Applications," Nutr. Res. Rev., (1994), 7, pp. 1-23.
Henningsson et al., "Short-Chain Fatty Acid Formatin at Fermentation of Indigestible Carbohydrates," Naringsforskning, vol. 45, No. 1, Dec. 1, 2001, pp. 165-168.
Office Action for U.S. Appl. No. 13/335,341 dated Jun. 26, 2018.
Amendment for U.S. Appl. No. 13/335,341 dated Sep. 26, 2018.
Advisory Action for U.S. Appl. No. 13/335,341 dated Oct. 30, 2018.
Amendment for U.S. Appl. No. 13/335,341 dated Nov. 26, 2018.
Office Action for U.S. Appl. No. 13/335,341 dated Mar. 21, 2019.
Office Action for U.S. Appl. No. 14/234,166 dated Nov. 30, 2018.
Amendment from U.S. Appl. No. 14/238,822 dated Sep. 12, 2018.
Office Action from U.S. Appl. No. 14/238,822 dated Jan. 11, 2019.
Office Action for U.S. Appl. No. 15/791,052 dated Dec. 10, 2018.
Response to Office Action for U.S. Appl. No. 15/791,052 dated Apr. 10, 2019.
Office Action from Canadian Patent Application No. 2,822,497 dated Sep. 26, 2018.
Office Action in CA 2,842,672 dated Aug. 3, 2018.
Office Action in CA 2,822,660 dated Jan. 28, 2019.
Office Action in CA 2,822,219 dated Aug. 7, 2018.
Office Action in CA 2,822,219 dated Mar. 12, 2019.
Reexamination Decision from Chinese Application No. 201180068712.1 dated Oct. 10, 2018.
Office Action in EP Application No. 11813500.3 dated Jan. 8, 2019.
Exam Report from Indian Application No. 5653/DELNP/2013 dated Mar. 15, 2018.
Office Action in MX/a/2014/002491 dated Jul. 30, 2018.
Office Action in MX/a/2013/007692 dated Nov. 7, 2018.
Substantive Examination Adverse Report in MY Application No. PI2013002514 dated Jul. 31, 2018.
Office Action for TW 100149994 dated May 11, 2017.
Office Action for TW 100149994 dated Nov. 28, 2018.
Office Action for VN 1-2013-01948 dated May 25, 2015.
Office Action in VN 1-2013-02056 dated Nov. 19, 2018.
Anonymous, "Guidelines for the Evaluation of Probiotics in Food", Joint FAO/WHO Working Group Report on Drafting Guidelines for the Evaluation of Probiotics in Food, Food and Agriculture Organization of the United Nations and the World Health Organization, London, Ontario, Canada, Apr. 30 and May 1, 2002.
Buhner et al., "Activation of Human Enteric Neurons by Supernatants of Colonic Biopsy Specimens from Patients with Irritable Bowel Syndrome," Gastroentrology 2009, vol. 137, pp. 1425-1434.
Coppa et al., "Human Milk Oligosaccharides Inhibit the Adhesion to Caco-2 Cells of Diarrheal Pathogens: *Escherichia coli* Vibrio cholerae, and *Salmonella fyris*," Pediatric Research, vol. 59, No. 3, 2006, pp. 377-382.
Saugstad, "Oxidative Stress in the Newborn—a 30-Year Perspective," Biol Neonate 2005, Vo. 88, pp. 228-236.
Wood, "Enteric Neuroimmunophysiology and Pathophysiology" Gastroenterology 2004, vol. 127, No. 2, pp. 635-657.
"Practical Inflammation Manual", pp. 2 to 7, with English Translation.
Amendment for U.S. Appl. No. 14/234,166 dated Apr. 30, 2019.
Response to Office Action from U.S. Appl. No. 14/238,822 dated May 13, 2019.
Office Action in CA 2,842,672 dated Apr. 8, 2019.
English translation of First Office Action in CN 201610935257.5 dated Apr. 9, 2019.
Office action in MX/A/2013/007692 dated Apr. 11, 2019.
Office Action from Canadian Patent Application No. 2,822,497 dated Apr. 29, 2019.
Office Action in MX/a/2014/002491dated Mar. 14, 2019.
Office Action for U.S. Appl. No. 14/234,166 dated Aug. 19, 2019.
Amendment for U.S. Appl. No. 13/335,341 dated Jul. 22, 2019.
Office Action from U.S. Appl. No. 14/238,822 dated May 31, 2019.
Office Action for U.S. Appl. No. 15/791,052 dated Jul. 17, 2019.
Decision on Rejection in CN 201711012480.3 dated Jul. 18, 2019.
Substantive Examination Adverse Report in MY Application No. PI2017000647 dated May 21, 2019.
Avery "Molecular Targets of Oxidative Stress," Biochem J., 2011, vol. 424, pp. 201-210.
Nittynen, et al., "Galacto-oligosaccharides and Bowel Functions," Scandinavian Journal of Food and Nutrition 2007, 51 (2) pp. 62-66.
Van Dokkum et al., "Effect of Nondigestible Oligosaccharides on Large-Bowel Functions, Blood Lipid Concentrations and Glucose Absorption in Young Healthy Male Subjects," European Journal of Clinical Nutrition, No. 53, 1999, pp. 1-7.

\* cited by examiner

FIG. 2

Table 1. Composition of microbiological medium used in the *in vitro* experiment.

| Component | Concentration in medium |
|---|---|
| | mL/L |
| Solution A[1] | 330.0 |
| Solution B[2] | 330.0 |
| Trace mineral solution[3] | 10.0 |
| Water-soluble vitamin solution[4] | 20.0 |
| Folate:biotin solution[5] | 5.0 |
| Riboflavin solution[6] | 5.0 |
| Hemin solution[7] | 2.5 |
| Resazurin[8] | 1.0 |
| Distilled $H_2O$ | 296.1 |
| | g/L |
| $Na_2CO_3$ | 4.0 |
| Cysteine $HCl-H_2O$ | 0.5 |
| Trypticase | 0.5 |
| Yeast extract | 0.5 |

[1] Composition (g/L): NaCl, 5.4; $KH_2PO_4$, 2.7; $CaCl_2-H_2O$, 0.16; $MgCl_2-6H_2O$, 0.12; $MnCl_2-4H_2O$, 0.06; $CoCl_2-6H_2O$, 0.06; $(NH_4)_2SO_4$, 5.4.
[2] Composition (g/L): $K_2HPO_4$, 2.7.
[3] Composition (mg/L): ethylenediaminetetraacetic acid (disodium salt), 500; $FeSO_4-7H_2O$, 200; $ZnSO_4-7H_2O$, 10; $MnCl_2-4H_2O$, 3; $H_3PO_4$, 30; $CoCl_2-6H_2O$, 20; $CuCl_2-2H_2O$, 1; $NiCl_2-6H_2O$, 2; $Na_2MoO_4-2H_2O$, 3.
[4] Composition (mg/L): thiamin-HCl, 100; d-pantothenic acid, 100; niacin, 100; pyridoxine, 100; p-aminobenzoic acid, 5; vitamin $B_{12}$, 0.25.
[5] Composition (mg/L): folic acid, 10; d-biotin, 2; $NH_4HCO_3$, 100.
[6] Composition: riboflavin, 10 mg/mL in 5 mmol/L of Hepes.
[7] Composition: hemin, 500 mg/mL in 10 mmol/L of NaOH.
[8] Composition: resazurin, 1 g/L in distilled $H_2O$.

Time by substrate effects on pH change from baseline

Time, hr a,b Points not sharing a common superscript letter within each time differ (P<0.05)

Total short-chain fatty acid (SCFA) production change from baseline as affected by substrate and time *in vitro*.

Time, hr a,b Points not sharing a common superscript letter within each time differ (P<0.05)

METHODS FOR DECREASING THE INCIDENCE OF NECROTIZING ENTEROCOLITIS IN INFANTS, TODDLERS, OR CHILDREN USING HUMAN MILK OLIGOSACCHARIDES

CROSS REFERENCE TO RELATED APPLICATIONS

This application is a divisional application of U.S. application Ser. No. 13/334,933, filed on Dec. 22, 2011, which claims the benefit of U.S. Provisional Application No. 61/428,863 filed on Dec. 31, 2010; and U.S. Provisional Application No. 61/428,868 filed on Dec. 31, 2010, which disclosures are incorporated by reference in their entirety.

FIELD OF THE DISCLOSURE

The present disclosure relates to human milk oligosaccharides (HMOs) for improving gastrointestinal function and tolerance in infants, toddlers, and children. More particularly, the present disclosure relates to human milk fortifiers, preterm and term infant formulas, and pediatric formulas comprising HMOs that can stimulate enteric nerve cells in the gastrointestinal tract, thereby treating and/or preventing numerous gastrointestinal-related conditions and diseases.

BACKGROUND OF THE DISCLOSURE

During postnatal development, a newborn's intestine experiences a process of maturation that ends with the production of gastrointestinal epithelium that functions as a selective barrier (i.e., gut barrier). The gastrointestinal epithelium permits the absorption of nutrients, electrolytes and water, while preventing exposure to dietary and microbial antigens, including food allergens. Specifically, this barrier limits the passage of antigens to the systemic circulation, thereby preventing infection, inflammatory reactions, and other gastrointestinal diseases and disorders that may occur during infancy and later in life. For very young infants, and particularly, preterm infants, who have an immature immune system and intestinal tract, development of suboptimal intestinal flora may result in infection, diarrhea, allergies, and food intolerance.

Barrier formation and maintenance has been found to be affected by the diet. Breast milk contains components that not only act as pathogen receptor analogues, but also activate immune factors by infant intestinal epithelial cells and/or associated immune cell populations to enhance development and maturation of the infant's gastrointestinal and immune systems.

Not all infants, however, are in a position to receive human breast milk. It would therefore be desirable to provide nutritional compositions, and synthetic infant formulas in particular, that can produce nutritional benefits including improved gastrointestinal growth, development, and maturation. It would additionally be beneficial if the nutritional compositions could enhance immunity against microbial infections and other gastrointestinal diseases, conditions, and disorders.

SUMMARY OF THE DISCLOSURE

The present disclosure is directed to nutritional compositions, including synthetic infant formulas, synthetic pediatric formulas, and synthetic child formulas including at least one HMO alone or in combination with other components such as prebiotic oligosaccharides and/or probiotics, for improving gut function and immunity in an infant, toddler, child, or adult, along with related methods of use. More particularly, the nutritional compositions can improve growth and maturation of the gut barrier, thereby treating and/or preventing formula intolerance or other gastrointestinal diseases and/or disorders resulting from a loss of dysfunction of the gut barrier.

One embodiment is directed to a method of reducing the incidence of necrotizing enterocolitis in an infant, toddler, or child in need thereof. The method comprises administering to the infant, toddler, or child a composition comprising human milk oligosaccharides in a total amount of from about 0.001 mg/mL to about 20 mg/mL.

Another embodiment is directed to a method of reducing the incidence of necrotizing enterocolitis in an infant, toddler, or child in need thereof. The method comprises administering to the infant, toddler, or child a nutritional composition comprising 6'-sialyllactose, 2'-fucosyllactose, and lacto-N-neotetraose.

Another embodiment is directed to a synthetic formula for improving the feeding intolerance of an infant, toddler, or child in need thereof. The synthetic formula comprises from about 0.2 mg/mL to about 20 mg/mL of an oligosaccharide blend, wherein the oligosaccharide blend comprises a first oligosaccharide selected from the group consisting of a fructooligosaccharide, a galactooligosaccharide, lacto-N-neotetraose, 2'-fucosyllactose, and combinations thereof a second oligosaccharide selected from the group consisting of 3'-sialyllactose, 6'-sialyllactose, and combinations thereof and a third oligosaccharide selected from the group consisting of inulin, a gum, polydextrose, and combinations thereof.

Another embodiment is directed to a synthetic formula for improving the feeding intolerance of an infant, toddler, or child in need thereof. The synthetic formula comprises from about 0.2 mg/mL to about 20 mg/mL of an oligosaccharide blend, wherein the oligosaccharide blend comprises a first oligosaccharide selected from the group consisting of a fructooligosaccharide, a galactooligosaccharide, lacto-N-neotetraose, 2'-fucosyllactose, and combinations thereof and a second oligosaccharide selected from the group consisting of 3'-sialyllactose, 6'-sialyllactose, and combinations thereof.

Another embodiment is directed to a method of improving the feeding tolerance of an infant, toddler, or child in need thereof. The method comprises administering to the infant, toddler, or child a nutritional composition comprising from about 0.2 mg/mL to about 20 mg/mL of an oligosaccharide blend, wherein the oligosaccharide blend comprises a first oligosaccharide selected from the group consisting of a fructooligosaccharide, a galactooligosaccharide, lacto-N-neotetraose, 2'-fucosyllactose, and combinations thereof; a second oligosaccharide selected from the group consisting of 3'-sialyllactose, 6'-sialyllactose, and combinations thereof; and a third oligosaccharide selected from the group consisting of inulin, a gum, polydextrose, and combinations thereof.

Another embodiment is directed to a method of improving the feeding tolerance of an infant, toddler, or child in need thereof. The method comprises administering to the infant, toddler, or child a synthetic pediatric formula comprising from about 0.2 mg/mL to about 20 mg/mL of an oligosaccharide blend, wherein the oligosaccharide blend comprises a first oligosaccharide selected from the group consisting of a fructooligosaccharide, a galactooligosaccharide, lacto-N- neotetraose, 2'-fucosyllactose, and combinations thereof; a second oligosaccharide selected from the group consisting of 3'-sialyllactose, 6'-sialyllactose, and combinations thereof; and a third oligosaccharide selected from the group consisting of inulin, a gum, polydextrose, and combinations thereof.

It has been discovered that HMOs that are delivered to the gut tissue stimulate the gut-brain-immune axis, and improve the immune system and enteric nervous system. Specifically, it has been found that 2'-fucosyllactose stimulates enteric nerve cells in the gastrointestinal tract such that gut function may be improved and gastrointestinal issues minimized.

Additionally, it has been found that the digestive tolerance of an infant, toddler, child, or adult can be significantly increased by administering to the infant, toddler, child or adult a select blend of carbohydrates including HMOs. Specifically, the carbohydrate blend includes a combination of fast, medium, and slowly digested carbohydrates including specific HMOs such as lacto-N-neotetraose, 2'-fucosyllactose, 3'-fucosyllactose, 3'-sialyllactose and/or 6'-sailyllactose.

Moreover, it has been found that intestinal barrier integrity of an infant, toddler, child, or adult can be significantly improved by administering to the infant, toddler, child, or adult a synbiotic composition including HMOs. Specifically, the synbiotic combination includes a probiotic, at least one of a galactooligosaccharide and a fructooligosaccharide (such as a short chain fructooligosaccharide) and at least one HMO. The synbiotic composition promotes the colonization of beneficial intestinal microbiota in order to discourage the growth of harmful bacteria.

Although the nutritional compositions and methods are primarily discussed herein in relation to preterm infants and infants in general, it should be understood that many of the benefits discussed herein may be provided to toddlers, children, and adults administered combinations of the HMOs alone, or with other components as described herein, such as prebiotic oligosaccharides and/or probiotics, for example. Particularly, in some embodiments, the incidence of gastrointestinal diseases and disorders that generally affect adults, such as Crohn's disease, irritable bowel syndrome and the like, can be reduced with the use of the nutritional compositions of the present disclosure including HMOs.

BRIEF DESCRIPTION OF THE DRAWINGS

FIG. 2 is a table setting forth the microbiological medium used in the in vitro experiment of Example 36.

DETAILED DESCRIPTION OF THE DISCLOSURE

Figure 1:
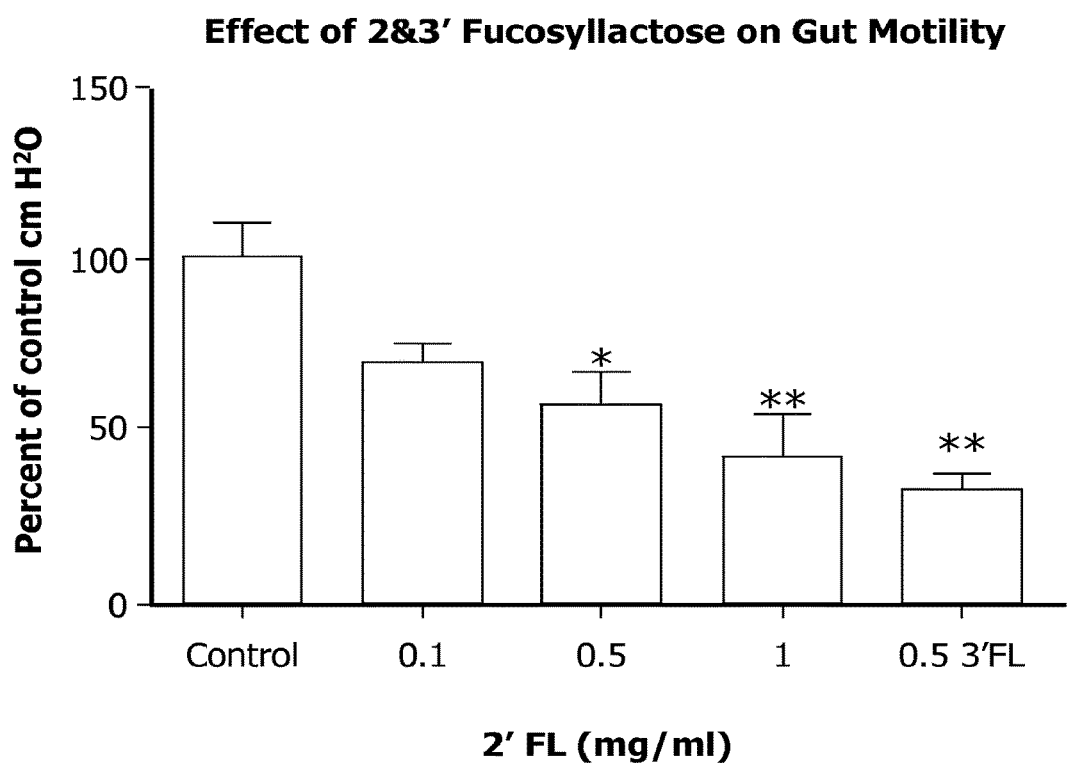
FIG. 1 is a graph depicting the effect of 2'FL and 3'FL on gut motility as measured in Example 35.

The nutritional compositions and methods described herein utilize HMOs alone or in combination with at least one other prebiotic oligosaccharide and/or a probiotic for controlling and reducing a number of diseases, disorders and conditions related to the gut-brain-immune system. These and other features of the nutritional compositions and methods, as well as some of the many optional variations and additions, are described in detail hereafter.

The terms "retort packaging" and "retort sterilizing" are used interchangeably herein, and unless otherwise specified, refer to the common practice of filling a container, most typically a metal can or other similar package, with a nutritional liquid and then subjecting the liquid-filled package to the necessary heat sterilization step, to form a sterilized, retort packaged, nutritional liquid product.

The term "aseptic packaging" as used herein, unless otherwise specified, refers to the manufacture of a packaged product without reliance upon the above-described retort packaging step, wherein the nutritional liquid and package are sterilized separately prior to filling, and then are combined under sterilized or aseptic processing conditions to form a sterilized, aseptically packaged, nutritional liquid product.

The terms "fat" and "oil" as used herein, unless otherwise specified, are used interchangeably to refer to lipid materials derived or processed from plants or animals. These terms also include synthetic lipid materials so long as such synthetic materials are suitable for oral administration to humans.

The term "human milk oligosaccharide" or "HMO", unless otherwise specified, refers generally to a number of complex carbohydrates found in human breast milk that can be in acidic or neutral form, and to precursors thereof. Exemplary non-limiting human milk oligosaccharides include 3'-sialyllactose, 6'-sialyllactose, 3'-fueosyllactose, 2'-fueosyllactose, and lacto-N-neo-tetraose. Exemplary human milk oligosaccharide precursors includes sialic acid and/or fucose.

The term "shelf stable" as used herein, unless otherwise specified, refers to a nutritional product that remains commercially stable after being packaged and then stored at 18-24° C. for at least 3 months, including from about 6 months to about 24 months, and also including from about 12 months to about 18 months.

The terms "nutritional formulation" or "nutritional composition" as used herein, are used interchangeably and, unless otherwise specified, refer to synthetic formulas including nutritional liquids, nutritional powders, nutritional solids, nutritional semi-solids, nutritional semi-liquids, nutritional supplements, and any other nutritional food product as known in the art. The nutritional powders may be reconstituted to form a nutritional liquid, all of which comprise one or more of fat, protein and carbohydrate and are suitable for oral consumption by a human. The terms "nutritional formulation" or "nutritional composition" do not include human breast milk.

The term "nutritional liquid" as used herein, unless otherwise specified, refers to nutritional compositions in ready-to-drink liquid form, concentrated form, and nutritional liquids made by reconstituting the nutritional powders described herein prior to use.

The term "nutritional powder" as used herein, unless otherwise specified, refers to nutritional compositions in flowable or scoopable form that can be reconstituted with water or another aqueous liquid prior to consumption and includes both spraydried and drymixed/dryblended powders.

The term "nutritional semi-solid," as used herein, unless otherwise specified, refers to nutritional products that are intermediate in properties, such as rigidity, between solids and liquids. Some semi-solids examples include puddings, gelatins, and doughs.

The term "nutritional semi-liquid," as used herein, unless otherwise specified, refers to nutritional products that are intermediate in properties, such as flow properties, between liquids and solids. Some semi-liquids examples include thick shakes and liquid gels.

The term "infant" as used herein, unless otherwise specified, refers to a person 12 months or younger. The term "preterm infant" as used herein, refers to a person born prior to 36 weeks of gestation.

The term "toddler" as used herein, unless otherwise specified, refers to a person greater than one year of age up to three years of age.

The term "child" as used herein, unless otherwise specified, refers to a person greater than three years of age up to twelve years of age.

The term "newborn" as used herein, unless otherwise specified, refers to a person from birth up to four weeks of age.

The terms "infant formula" or "synthetic infant formula" as used herein, unless otherwise specified, are used interchangeably and refer to liquid, semiliquid, solid, and semi-solid human milk replacements or substitutes that are suitable for consumption by an infant. The synthetic formulas include components that are of semi-purified or purified origin. As used herein, unless otherwise specified, the terms "semi-purified" or "purified" refer to a material that has been prepared by purification of a natural material or by synthesis. The terms "infant formula" or "synthetic infant formula" do not include human breast milk.

The term "synthetic pediatric formula" as used herein, unless otherwise specified, refers to liquid, semi-liquid, solid, and semi-solid human milk replacements or substitutes that are suitable for consumption by an infant or toddler up to the age of 36 months (3 years). The synthetic formulas include components that are of semi-purified or purified origin. As used herein, unless otherwise specified, the terms "semi-purified" or "purified" refer to a material that has been prepared by purification of a natural material or by synthesis. The term "synthetic pediatric nutritional formula" does not include human breast milk.

The term "synthetic child formula" as used herein, unless otherwise specified, refers to liquid, semi-liquid, solid, and semi-solid human milk replacements or substitutes that are suitable for consumption by a child up to the age of 12 years. The synthetic formulas include components that are of semi-purified or purified origin. As used herein, unless otherwise specified, the terms "semi-purified" or "purified" refer to a material that has been prepared by purification of a natural material or by synthesis. The term "synthetic child nutritional formula" does not include human breast milk.

The term "preterm infant formula" as used herein, unless otherwise specified, refers to liquid and solid nutritional products suitable for consumption by a preterm infant.

The term "human milk fortifier" as used herein, unless otherwise specified, refers to liquid and solid nutritional products suitable for mixing with breast milk or preterm infant formula or infant formula for consumption by a preterm or term infant.

The terms "susceptible" and "at risk" as used herein, unless otherwise specified, mean having little resistance to a certain condition or disease, including being genetically predisposed, having a family history of, and/or having symptoms of the condition or disease.

The term "cognition" as used herein, unless otherwise specified, refers to an individual's ability for learning, memory acquisition, and memory recall.

The terms "growth of a virus" or "growth of bacteria" as used herein, unless otherwise specified, refer to the production, proliferation, or replication of a virus or bacteria.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The nutritional compositions and methods may comprise, consist of, or consist essentially of the essential elements of the compositions and methods as described herein, as well as any additional or optional element described herein or otherwise useful in nutritional composition applications.

Product Form

The nutritional compositions of the present disclosure may be formulated and administered in any known or otherwise suitable oral product form. Any solid, semi-solid, liquid, semi-liquid, or powder product form, including combinations or variations thereof, are suitable for use herein, provided that such forms allow for safe and effective oral delivery to the individual of the essential ingredients and any optional ingredients, as also defined herein.

The nutritional compositions of the present disclosure are desirably formulated as dietary product forms, which are defined herein as those embodiments comprising the ingredients of the present disclosure in a product form that then contains at least one of fat, protein, and carbohydrate, and preferably also contains vitamins, minerals, or combinations thereof. The nutritional compositions will comprise at least one HMO, and many times at least two or more HMOs, desirably in combination with at least one of protein, fat, vitamins, and minerals, to produce a nutritional combination.

The nutritional composition may be formulated with sufficient kinds and amounts of nutrients to provide a sole, primary, or supplemental source of nutrition, or to provide a specialized nutritional composition for use in individuals afflicted with specific diseases, disorders, or conditions or with a targeted nutritional benefit as described below.

Specific non-limiting examples of product forms suitable for use with the HMO-containing compositions as disclosed herein include, for example, liquid and powdered dietary supplements, liquid and powdered human milk fortifiers, liquid and powdered preterm infant formulas, liquid and powdered infant formulas, liquid and powdered elemental and semi-elemental formulas, liquid and powdered pediatric formulas, liquid and powdered toddler formulas, liquid and powdered follow-on formulas, liquid, powdered and solid adult nutritional formulas suitable for use with individuals suffering from food intolerance, allergies, immune disorders, and other gastrointestinal diseases, conditions, and/or disorders.

Nutritional Liquids

Nutritional liquids include both concentrated and ready-to-feed nutritional liquids. These nutritional liquids are most typically formulated as suspensions or emulsions, although other liquid forms are within the scope of the present disclosure.

Nutritional emulsions suitable for use may be aqueous emulsions comprising proteins, fats, and carbohydrates. These emulsions are generally flowable or drinkable liquids at from about 1° C. to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional emulsions may be and typically are shelf stable. The nutritional emulsions typically contain up to about 95% by weight of water, including from about 50% to about 95%, also including from about 60% to about 90%, and also including from about 70% to about 85%, by weight of water. The nutritional emulsions may have a variety of product densities, but most typically have a density greater than about 1.03 g/mL, including greater than about 1.04 g/mL, including greater than about 1.055 g/mL, including from about 1.06 g/mL to about 1.12 g/mL, and also including from about 1.085 g/mL to about 1.10 g/mL.

The nutritional emulsions may have a caloric density tailored to the nutritional needs of the ultimate user, although in most instances the emulsions comprise generally at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the emulsion may have a caloric density of from about 50-100 kcal/liter to about 660 kcal/liter, including from about 150 kcal/liter to about 500 kcal/liter. In some specific embodiments, the emulsion may have a caloric density of 25, or 50, or 75, or 100 kcal/liter.

The nutritional emulsion may have a pH ranging from about 3.5 to about 8, but are most advantageously in a range of from about 4.5 to about 7.5, including from about 5.5 to about 7.3, including from about 6.2 to about 7.2.

Although the serving size for the nutritional emulsion can vary depending upon a number of variables, a typical serving size is generally at least about 1 mL, or even at least about 2 mL, or even at least about 5 mL, or even at least about 10 mL, or even at least about 25 mL, including ranges from about 2 mL toabout 300 mL, including from about 4 mL to about 250 mL, and including from about 10 mL to about 240 mL.

Nutritional Solids

The nutritional solids may be in any solid form, but are typically in the form of flowable or substantially flowable particulate compositions, or at least particulate compositions. Particularly suitable nutritional solid product forms include spray dried, agglomerated and/or dryblended powder compositions. The compositions can easily be scooped and measured with a spoon or similar other device, and can easily be reconstituted by the intended user with a suitable aqueous liquid, typically water, to form a nutritional composition for immediate oral or enteral use. In this context, "immediate" use generally means within about 48 hours, most typically within about 24 hours, preferably right after reconstitution.

The nutritional powders may be reconstituted with water prior to use to a caloric density tailored to the nutritional needs of the ultimate user, although in most instances the powders are reconstituted with water to form compositions comprising at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the reconstituted powder may have a caloric density of from about 50-100 kcal/liter to about 660 kcal/liter, including from about 150 kcal/liter to about 500 kcal/liter. In some specific embodiments, the emulsion may have a caloric density of 25, or 50, or 75, or 100 kcal/liter.

Human Milk Oligosaccharides (HMOs)

The nutritional compositions of the present disclosure include at least one HMO, and in many embodiments, a combination of two or more HMOs. Oligosaccharides are one of the main components of human breast milk, which contains, on average, 10 grams per liter of neutral oligosaccharides and 1 gram perliter of acidic oligosaccharides. The compositional structure of HMOs is very complex and more than 200 different oligosaccharide-like structures are known.

The HMO or HMOs may be included in the nutritional compositions alone, or in some embodiments, in combination with other components (e.g., prebiotic oligosaccharides, probiotics, etc.) as described herein. In many embodiments, HMOs are included in the nutritional compositions with multiple additional components. The HMO or HMOs may be isolated or enriched from milk(s) secreted by mammals including, but not limited to: human, bovine, ovine, porcine, or caprine species. The HMOs may also be produced via microbial fermentation, enzymatic processes, chemical synthesis, or combinations thereof.

Suitable HMOs for use in the nutritional compositions may include neutral oligosaccharides, acidic oligosaccharides, n-acetylglucosylated oligosaccharides, and HMO precursors. Specific non-limiting examples of HMOs that may be included individually or in combination in the compositions of the present disclosure include: sialic acid (i.e., free sialic acid, lipid-bound sialic acid, protein-bound sialic acid); D-glucose (Glc); D-galactose (Gal); N-acetylglucosamine (GleNAc); L-fucose (Fuc); fucosyl oligosaccharides (i.e., Lacto-N-fucopentaose I; Lacto-N-fucopentaose II; 2'-Fucosyllactose; 3'-Fucosyllactose; Lacto-N-fucopentaose III; Lacto-N-difucohexaose I; and Lactodifucotetraose); non-fucosylated, non-sialylated oligosaccharides (i.e., Lacto-N-tetraose and Lacto-N-neotetraose); sialyl oligosaccharides (i.e., 3'-Sialyl-3-fucosyllactose; Disialomonofucosyllacto-N-neohexaose; Monofucosylmonosialyllacto-N-octaose (sialyl Lea); Sialyllacto-N-fucohexaose II; Disialyllacto-N-fucopentaose II; Monofucosyldisialyllacto-N-tetraose); and sialyl fucosyl oligosaccharides (i.e., 2'-Sialyllactose; 2-Sialyllactosamine; 3'-Sialyllactose; 3'-Sialyllactosamine; 6'-Sialyllactose; 6'-Sialyllactosamine; Sialyllacto-N-neotetraose c; Monosialyllacto-N-hexaose; Disialyllacto-N-hexaose I; Monosialyllacto-N-neohexaose I; Monosialyllacto-N-neohexaose II; Disialyllacto-N-neohexaose; Disialyllacto-N-tetraose; Disialyllacto-N-hexaose II; Sialyllacto-N-tetraose a; Disialyllacto-N-hexaose I; and Sialyllacto-N-tetraose b). Also useful are variants in which the glucose (Glc) at the reducing end is replaced by N-acetylglucosamine (e.g., 2'-fucosyl-N-acetylglucosamine (2'-FLNac) is such a variant to 2'-fucosyllactose). These HMOs are described more fully in U.S. Patent Application No. 2009/0098240, which is herein incorporated by reference in its entirety. Other suitable examples of HMOs that may be included in the compositions of the present disclosure include lacto-N-fucopentaose V, lacto-N-hexaose, para-lacto-N-hexaose, lacto-N-neohexaose, para-lacto-N-neohexaose, monofucosyllacto-N-hexaose II, isomeric fucosylated lacto-N-hexaose (1), isomeric fucosylated lacto-N-hexaose (3), isomeric fucosylated lacto-N-hexaose (2), difucosyl-para-lacto-N-neohexaose, difucosyl-para-lacto-N-hexaose, difucosyllacto-N-hexaose, lacto-N-neoocataose, para-lacto-N-octanose, iso-lacto-N-octaose, lacto-N-octaose, monofucosyllacto-neoocataose, monofucosyllacto-N-ocataose, difucosyllacto-N-octaose I, difucosyllacto-N-octaose II, difucosyllacto-N-neoocataose II, difucosyllacto-N-neoocataose I, lacto-N-decaose, trifucosyllacto-N-neooctaose, trifucosyllacto-N-octaose, trifucosyl-iso-lacto-N-octaose, lacto-N-difuco-hexaose II, sialyl-lacto-N-tetraose a, sialyl-lacto-N-tetraose b, sialyl-lacto-N-tetraose c, sialyl-fucosyl-lacto-N-tetraose I, sialyl-fucosyl-lacto-N-tetraose II, and disialyl-lacto-N-tetraose, and combinations thereof Particularly suitable nutritional compositions include at least one of the following HMOs or HMO precursors: sialic acid (SA); 2'-Sialyllactose (2'SL); 3'-Sialyllactose (3'SL); 6'-Sialyllactose (6'SL); 2'-Fucosyllactose (2'FL); 3'-Fucosyllactose (3'FL); and Lacto-N-tetraose and Lacto-N-neotetraose (LNnT), and in particular, combinations of 2'FL with at least one of 6'SL and 3'SL; and combinations of LNnT with at least one of 6'SL and 3'FL.

Other exemplary combinations include: SA, 3'SL, 6'SL; 3'FL, 2'FL, and LNnT; 3'SL, 6'SL, 3'FL, 2'FL, and LNnT; SA, 6'SL, 3'FL, 2'FL, and LNnT; SA, 3'SL, 3'FL, 2'FL, and LNnT; SA, 3'SL, 6'SL, 2'FL, and LNnT; SA, 3'SL, 6'SL, 3'FL, and LNnT; SA, 3'SL, 6'SL, 3'FL, and 2'FL; SA and 3'SL; SA and 6'SL; SA and 2'FL; SA and LNnT; SA, 3'SL, and 6'SL; SA, 3'SL and 3'FL; SA, 3'SL and 2'FL; SA, 3'SL and LNnT; SA, 6'SL and 3'FL; SA, 6'SL, and 2'FL; SA, 6'SL, and LNnT; SA, 3'FL, and 2'FL; SA, 3'FL, and LNnT; SA, 2'FL, and LNnT; SA, 3'SL, 6'SL, and 3'FL; SA, 3'SL, 6'SL and 2'FL; SA, 3'SL, 6'SL, and LNnT; SA, 3'SL, 3'FL, and 2'FL; SA, 3'SL, 3'FL, and LNnT; SA, 3'SL, 2'FL, and LNnT; SA, 6'SL, 3'FL, and 2'FL; SA, 6'SL, 2'FL, and LNnT; SA, 6'SL, 3'FL, and LNnT; SA, 3'FL, 2'FL, and LNnT; SA, 6'SL, 2'FL, and LNnT; SA, 3'SL, 3'FL, 2'FL, and LNnT; SA, 6'SL, 3'FL, 2'FL, and LNnT; SA, 3'SL, 6'SL, 3'FL, and LNnT; SA, 3'SL, 3'FL, 2'FL, and LNnT; SA, 3'SL, 6'SL, 2'FL, and LNnT; 3'SL, 6'SL, 3'FL, and 2'FL; 3'SL, 6'SL, 2'FL, and LNnT; 3'SL, 3'FL, 2'FL, and LNnT; 3'SL, 6'SL, 3'FL, and LNnT; 3'SL, 6'SL, and 3'FL; 3'SL, 3'FL, and 2'FL; 3'SL, 2'FL, and LNnT; 3'SL, 6'SL, and 2'FL; 3'SL, 6'SL, and LNnT; 3'SL and 3'FL; 3'SL and 2'FL; 3'SL and LNnT; 6'SL and 3'FL; 6'SL and 2'FL; 6'SL and LNnT; 6'SL, 3'FL, and LNnT; 6'SL, 3'FL, 2'FL, and LNnT; 3'FL, 2'FL, and LNnT; 3'FL and LNnT; and 2'FL and LNnT.

The HMOs are present in the nutritional compositions in total amounts of HMO in the composition (mg of HMO per mL of composition) of at least about 0.001 mg/mL, including at least about 0.01 mg/mL, including from about 0.001 mg/mL to about 20 mg/mL, including from about 0.01 mg/mL to about 20 mg/mL, including from about 0.001 mg/mL to about 15 mg/mL, including from about 0.01 mg/mL to about 15 mg/mL, including from about 0.001 mg/mL to about 10 mg/mL, including from about 0.01 mg/mL to about 10 mg/mL, including from about 0.001 mg/mL to about 5 mg/mL, including from about 0.01 mg/mL to about 5 mg/mL, and including from about 0.001 mg/mL to about 1 mg/mL of total HMO in the nutritional composition, including from about 0.001 mg/mL to about 0.23 mg/mL, and including from about 0.01 mg/mL to about 0.23 mg/mL. Typically, the amount of HMO in the nutritional composition will depend on the specific HMO or HMOs present and the amounts of other components in the nutritional compositions.

In one specific embodiment when the nutritional composition is a nutritional powder, the total concentration of HMOs in the nutritional powder is from about 0.0005% to about 5%, including from about 0.01% to about 1% (by weight of the nutritional powder).

In another specific embodiment, when the nutritional composition is a ready-to-feed nutritional liquid, the total concentration of HMOs in the ready-to-feed nutritional liquid is from about 0.0001% to about 0.50%, including from about 0.001% to about 0.15%, including from about 0.01% to about 0.10%, and further including from about 0.01% to about 0.03% (by weight of the ready-to-feed nutritional liquid).

In another specific embodiment, when the nutritional composition is a concentrated nutritional liquid, the total concentration of HMOs in the concentrated liquid is from about 0.0002% to about 0.60%, including from about 0.002% to about 0.30%, including from about 0.02% to about 0.20%, and further including from about 0.02% to about 0.06% (by weight of the concentrated nutritional liquid).

In one specific embodiment, the nutritional composition includes a neutral human milk oligosaccharide in an amount of from about 0.001 mg/mL to about 20 mg/mL, including from 0.01 mg/mL to about 20 mg/mL, including from about 0.001 mg/mL to less than 2 mg/mL, and including from about 0.01 mg/mL to less than 2 mg/mL.

In one specific embodiment of the present disclosure, a nutritional composition includes 2'FL. The 2'FL may be the only HMO included in the nutritional composition, or other additional HMOs may also be included in the nutritional composition (e.g., the 2'FL may be combined with 3'SL and/or 6'SL in some specific embodiments). In one embodiment, the 2'FL is included in the nutritional composition in an amount of from about 0.001 mg/mL to about 20 mg/mL, including from about 0.01 mg/mL to about 20 mg/mL, including from about 0.001 mg/mL to less than 2 mg/mL, and including from about 0.01 mg/mL to less than 2 mg/mL. In another embodiment, the 2'FL is included in the nutritional composition in an amount of from about 0.001 mg/mL to about 20 mg/mL, including from about 0.01 mg/mL to about 20 mg/mL, including from greater than 2.5 mg/mL to about 20 mg/mL, including from greater than 2.5 mg/mL to about 15 mg/mL, and including from greater than 2.5 mg/mL to about 10 mg/mL.

In one specific embodiment, the nutritional composition includes 6'SL, alone or in combination with other HMOs, in an amount of from about 0.001 mg/mL to about 20 mg/mL, including from about 0.01 mg/mL to about 20 mg/mL, including from about 0.001 mg/mL to less than 0.25 mg/mL, and including from about 0.01 mg/mL to less than 0.25 mg/mL. In another embodiment, the nutritional composition includes 6'SL, alone or in combination with other HMOs, in an amount of from about 0.001 mg/mL to about 20 mg/mL, including from about 0.01 mg/mL to about 20 mg/mL, including from greater than 0.4 mg/mL to about 20 mg/mL, including from greater than 0.4 mg/mL to about 15 mg/mL, and including from greater than 0.4 mg/mL to about 10 mg/mL.

In one embodiment, when the nutritional composition includes 6'SL, the total amount of HMOs in the nutritional composition includes at least about 88% (by total weight HMOs) 6'SL, including from about 88% (by total weight HMOs) to about 96% (by total weight HMOs), including from about 88% (by total weight HMOs) to about 100% (by total weight HMOs), and including about 100% (by total weight HMOs) 6'SL.

In another embodiment, the nutritional composition includes 3'SL, alone or in combination with other HMOs, in an amount of from about 0.001 mg/mL to about 20 mg/mL, including from about 0.01 mg/mL to about 20 mg/mL, including from about 0.001 mg/mL to less than 0.15 mg/mL, including from about 0.01 mg/mL to less than 0.15 mg/mL, including from greater than 0.25 mg/mL to about 20 mg/mL, including from greater than 0.25 mg/mL to about 15 mg/mL, and including from greater than 0.25 mg/mL to about 10 mg/mL.

In one embodiment, when the nutritional composition includes 3'SL, the total amount of HMOs in the nutritional composition includes at least about 85% (by total weight HMOs) 3'SL, including from about 85% (by total weight HMOs) to about 88% (by total weight HMOs), including from about 88% (by total weight HMOs) to about 100% (by total weight HMOs), and including about 100% (by total weight HMOs) 3'SL.

In one specific embodiment, the nutritional composition includes LNnT, alone or in combination with other HMOs, in an amount of from about 0.001 mg/mL to about 20 mg/mL, including from about 0.01 mg/mL to about 20 mg/mL, including from about 0.001 mg/mL to less than 0.2 mg/mL, including from about 0.01 mg/mL to less than 0.2 mg/mL, including from greater than 0.32 mg/mL to about 20 mg/mL, including from greater than 0.32 mg/mL to about 15 mg/mL, and including from greater than 0.32 mg/mL to about 10 mg/mL.

Additional Prebiotic Oligosaccharides

The nutritional compositions of the present disclosure may, in addition to the HMOs described above, comprise an additional source or sources of prebiotic oligosaccharides (the total amount of oligosaccharides being referred to herein as an "oligosaccharide blend" of the nutritional composition). Suitable additional sources of prebiotic oligosaccharides for use in the nutritional compositions include any prebiotic oligosaccharide that is suitable for use in an oral nutritional composition and is compatible with the essential elements and features of such compositions. In some embodiments, the nutritional composition includes a combination of one or more HMOs and one or more additional prebiotic oligosaccharides such that the composition provides a synergistic benefit to the end user, such as a synergistic benefit in improving feeding intolerance in infants.

In some embodiments, the combinations of HMO or HMOs with the additional prebiotic oligosaccharides to provide the synergistic effect include HMOs and additional prebiotic oligosaccharides that ferment at a rapid rate ("rapidly-fermenting oligosaccharides"), oligosaccharides that ferment at a moderate rate ("medium-fermenting oligosaccharides"), and/or oligosaccharides that ferment at a slow rate ("slowly-fermenting oligosaccharides"). Some preferred embodiments provide a nutritional composition that includes at least one HMO in combination with a rapidly-fermenting oligosaccharide, a medium-fermenting oligosaccharide, and/or a slowly-fermenting oligosaccharide.

Non-limiting examples of suitable additional prebiotic oligosaccharides for use in the nutritional compositions described herein include prebiotic oligosaccharides that have a degree of polymerization (DP) of at least 2 monose units, which are not or only partially digested in the intestine by the action of acids or digestive enzymes present in the human upper digestive tract (small intestine and stomach), but which are fermentable by the human intestinal flora. The term "monose units" refers to units having a closed ring structure, preferably hexose, e.g., the pyranose or furanose forms. Particularly preferred oligosaccharides for use in combination with the HMO or HMOs in the nutritional compositions of the present disclosure include galactooligosaccharides (GOS), fructooligosaccharides (FOS), short chain fructooligosaccharides, inulin, polydextrose (PDX), pectin hydrolysate, and gum fiber. In one specific embodiment, the gum fiber is gum arabic.

The oligosaccharide blend is present in the nutritional compositions in a total amount of at least about 0.001 mg/mL, including at least about 0.01 mg/mL, including at least about 0.1 mg/mL, including at least about 1 mg/mL, including from about 0.001 mg/mL to about 20 mg/mL, including from about 1 mg/mL to about 20 mg/mL, including from about 1 mg/mL to about 15 mg/mL, including from about 1 mg/mL to about 10 mg/mL, including from about 1 mg/mL to about 5 mg/mL, and including from about 2 mg/mL to about 20 mg/mL. In one embodiment, the oligosaccharide blend is present in the nutritional composition in a total amount of from about 1 mg/mL to about 4 mg/mL.

Typically, when used as an oligosaccharide blend, the nutritional compositions, in addition to the HMO or HMOs, include at least one rapidly-fermented oligosaccharide, at least one medium-fermented oligosaccharide, and, optionally, at least one slowly-fermented oligosaccharide to provide a nutritional composition that is tolerated well by preterm and term infants (i.e., reduced gassiness and/or stool frequency). Rapidly-fermented oligosaccharides generally have a fermentation rate of greater than 4,000 µg/g of dry matter/hour; medium-fermented oligosaccharides generally have a fermentation rate of from 1,500 µg/g of dry matter/hour to 4,000 µg/g of dry matter/hour; and slowly-fermented oligosaccharides generally have a fermentation rate of less than 1,500 µg/g of dry matter/hour.

By way of specific example, rapidly-fermented oligosaccharides include FOS, GOS (about 9,304 µg/g of dry matter/hour), LNnT (about 4,488 µg/g of dry matter/hour), 2'FL (about 4,872 µg/g of dry matter/hour), and combinations thereof. Medium-fermented oligosaccharides include 6'SL (about 1,809 µg/g of dry matter/hour), 3'SL, 2'FL, 3'FL, LNnT and combinations thereof. Slowly-fermented oligosaccharides include longer chain carbohydrates such as inulin (about 1,435 µg/g of dry matter/hour), gum fibers (e.g., gum arabic (about 785 µg/g of dry matter/hour)), and combinations thereof.

When used in an oligosaccharide blend, the rapidly-fermented oligosaccharides can be included in the nutritional compositions in amounts of from about 0.05 mg/mL to about 20 mg/mL, including from about 0.5 mg/mL to about 15 mg/mL, including from about 0.5 mg/mL to about 10 mg/mL, including from about 1 mg/mL to about 15 mg/mL, including from about 1 mg/mL to about 10 mg/mL, including from about 2 mg/mL to about 8 mg/mL, and also including from about 3 mg/mL to about 5 mg/mL. The medium-fermented oligosaccharides can be included in the nutritional compositions in amounts of from about 0.05 mg/mL to about 20 mg/mL, including from about 0.05 mg/mL to about 15 mg/mL, including from about 0.05 mg/mL to about 10 mg/mL, including from about 0.05 mg/mL to about 5 mg/mL, including from about 0.05 mg/mL to about 2.5 mg/mL, including from about 0.05 mg/mL to about 1 mg/mL, including from about 0.05 mg/mL to about 0.5 mg/mL, and including from about 0.05 mg/mL to about 0.25 mg/mL. The slowly-fermented oligosaccharides can be included in the nutritional compositions in amounts of from about 0.05 mg/mL to about 20 mg/mL, including from about 0.05 mg/mL to about 15 mg/mL, including from about 0.05 mg/mL to about 10 mg/mL, including from about 0.05 mg/mL to about 5 mg/mL, and also including from about 0.05 mg/mL to about 2.5 mg/mL.

In one specific embodiment, the nutritional composition includes an oligosaccharide blend including LNnT, 6'SL and inulin in a total amount of oligosaccharide blend of from about 0.05 mg/mL to about 20 mg/mL.

In another specific embodiment, the nutritional composition includes an oligosaccharide blend including 2'FL, 6'SL and inulin in a total amount of oligosaccharide blend of from about 0.001 mg/mL to about 20 mg/mL, including from about 0.01 mg/mL to about 20 mg/mL.

Other exemplary combinations include: FOS, GOS, 2'FL, LNnT, 3'SL, and 6'SL; FOS, GOS, 2'FL, 3'SL, and 6'SL; FOS, GOS, LNnT, 3'SL, and 6'SL; FOS, 2'FL, LNnT, 3'SL, and 6'SL; GOS, 2'FL, LNnT, 3'SL, and 6'SL; FOS, GOS, 3'SL, and 6'SL; FOS, 2'FL, 3'SL, and 6'SL; FOS, LNnT, 3'SL, and 6'SL; GOS, 2'FL, 3'SL, and 6'SL; GOS, LNnT, 3'SL, and 6'SL; 2'FL, LNnT, 3'SL, and 6'SL; FOS, 3'SL, and 6'SL; GOS, 3'SL, and 6'SL; 2'FL, 3'SL, and 6'SL; LNnT, 3'SL, and 6'SL; FOS, GOS, 2'FL, LNnT, and 3'SL; FOS, GOS, 2'FL, and 3'SL; FOS, GOS, LNnT, and 3'SL; FOS, 2'FL, LNnT, and 3'SL; GOS, 2'FL, LNnT, and 3'SL; FOS, GOS, and 3'SL; FOS, 2'FL, and 3'SL; FOS, LNnT, and 3'SL; GOS, 2'FL, and 3'SL; GOS, LNnT, and 3'SL; 2'FL, LNnT, and 3'SL; FOS and 3'SL; GOS and 3'SL; 2'FL and 3'SL; LNnT and 3'SL; FOS, GOS, 2'FL, LNnT, and 6'SL; FOS, GOS, 2'FL, and 6'SL; FOS, GOS, LNnT, and 6'SL; FOS, 2'FL, LNnT, and 6'SL; GOS, 2'FL, LNnT, and 6'SL; FOS, GOS, and 6'SL; FOS, 2'FL, and 6'SL; FOS, LNnT, and 6'SL; GOS, 2'FL, and 6'SL; GOS, LNnT, and 6'SL; 2'FL, LNnT, and 6'SL; FOS and 6'SL; GOS and 6'SL; 2'FL and 6'SL; and LNnT and 6'SL.

Further exemplary combinations include: FOS, GOS, 2'FL, LNnT, 3'SL, 6'SL, inulin, a gum, and polydextrose; FOS, GOS, 2'FL, 3'SL, 6'SL, inulin, a gum, and polydextrose; FOS, GOS, LNnT, 3'SL, 6'SL, inulin, a gum, and polydextrose; FOS, 2'FL, LNnT, 3'SL, 6'SL, inulin, a gum, and polydextrose; GOS, 2'FL, LNnT, 3'SL, 6'SL, inulin, a gum, and polydextrose; FOS, GOS, 3'SL, 6'SL, inulin, a gum, and polydextrose; FOS, 2'FL, 3'SL, 6'SL, inulin, a gum, and polydextrose; FOS, LNnT, 3'SL, 6'SL, inulin, a gum, and polydextrose; GOS, 2'FL, 3'SL, 6'SL, inulin, a gum, and polydextrose; GOS, LNnT, 3'SL, 6'SL, inulin, a gum, and polydextrose; 2'FL, LNnT, 3'SL, 6'SL, inulin, a gum, and polydextrose; FOS, 3'SL, 6'SL, inulin, a gum, and polydextrose; GOS, 3'SL, 6'SL, inulin, a gum, and polydextrose; 2'FL, 3'SL, 6'SL, inulin, a gum, and polydextrose; LNnT, 3'SL, 6'SL, inulin, a gum, and polydextrose; FOS, GOS, 2'FL, LNnT, 3'SL, inulin, a gum, and polydextrose; FOS, GOS, 2'FL, 3'SL, inulin, a gum, and polydextrose; FOS, GOS, LNnT, 3'SL, inulin, a gum, and polydextrose; FOS, 2'FL, LNnT, 3'SL, inulin, a gum, and polydextrose; GOS, 2'FL, LNnT, 3'SL, inulin, a gum, and polydextrose; FOS, GOS, 3'SL, inulin, a gum, and polydextrose; FOS, 2'FL, 3'SL, inulin, a gum, and polydextrose; FOS, LNnT, 3'SL, inulin, a gum, and polydextrose; GOS, 2'FL, 3'SL, inulin, a gum, and polydextrose; GOS, LNnT, 3'SL, inulin, a gum, and polydextrose; 2'FL, LNnT, 3'SL, inulin, a gum, and polydextrose; FOS, 3'SL, inulin, a gum, and polydextrose; GOS, 3'SL, inulin, a gum, and polydextrose; 2'FL, 3'SL, inulin, a gum, and polydextrose; LNnT, 3'SL, inulin, a gum, and polydextrose; FOS, GOS, 2'FL, LNnT, 6'SL, inulin, a gum, and polydextrose; FOS, GOS, 2'FL, 6'SL, inulin, a gum, and polydextrose; FOS, GOS, LNnT, 6'SL, inulin, a gum, and polydextrose; FOS, 2'FL, LNnT, 6'SL, inulin, a gum, and polydextrose; GOS, 2'FL, LNnT, 6'SL, inulin, a gum, and polydextrose; FOS, GOS, 6'SL, inulin, a gum, and polydextrose; FOS, 2'FL, 6'SL, inulin, a gum, and polydextrose; FOS, LNnT, 6'SL, inulin, a gum, and polydextrose; GOS, 2'FL, 6'SL, inulin, a gum, and polydextrose; GOS, LNnT, 6'SL, inulin, a gum, and polydextrose; 2'FL, LNnT, 6'SL, inulin, a gum, and polydextrose; FOS, 6'SL, inulin, a gum, and polydextrose; GOS, 6'SL, inulin, a gum, and polydextrose; 2'FL, 6'SL, inulin, a gum, and polydextrose; LNnT, 6'SL, inulin, a gum, and polydextrose; FOS, GOS, 2'FL, LNnT, 3'SL, 6'SL, inulin, and a gum; FOS, GOS, 2'FL, 3'SL, 6'SL, inulin, and a gum; FOS, GOS, LNnT, 3'SL, 6'SL, inulin, and a gum; FOS, 2'FL, LNnT, 3'SL, 6'SL, inulin, and a gum; GOS, 2'FL, LNnT, 3'SL, 6'SL, inulin, and a gum; FOS, GOS, 3'SL, 6'SL, inulin, and a gum; FOS, 2'FL, 3'SL, 6'SL, inulin, and a gum; FOS, LNnT, 3'SL, 6'SL, inulin, and a gum; GOS, 2'FL, 3'SL, 6'SL, inulin, and a gum; GOS, LNnT, 3'SL, 6'SL, inulin, and a gum; 2'FL, LNnT, 3'SL, 6'SL, inulin, and a gum; FOS, 3'SL, 6'SL, inulin, and a gum; GOS, 3'SL, 6'SL, inulin, and a gum; 2'FL, 3'SL, 6'SL, inulin, and a gum; LNnT, 3'SL, 6'SL, inulin, and a gum; FOS, GOS, 2'FL, LNnT, 3'SL, inulin, and a gum; FOS, GOS, 2'FL, 3'SL, inulin, and a gum; FOS, GOS, LNnT, 3'SL, inulin, and a gum; FOS, 2'FL, LNnT, 3'SL, inulin, and a gum; GOS, 2'FL, LNnT, 3'SL, inulin, and a gum; FOS, GOS, 3'SL, inulin, and a gum; FOS, 2'FL, 3'SL, inulin, and a gum; FOS, LNnT, 3'SL, inulin, and a gum; GOS, 2'FL, 3'SL, inulin, and a gum; GOS, LNnT, 3'SL, inulin, and a gum; 2'FL, LNnT, 3'SL, inulin, and a gum; FOS, 3'SL, inulin, and a gum; GOS, 3'SL, inulin, and a gum; 2'FL, 3'SL, inulin, and a gum; LNnT, 3'SL, inulin, and a gum; FOS, GOS, 2'FL, LNnT, 6'SL, inulin, and a gum; FOS, GOS, 2'FL, 6'SL, inulin, and a gum; FOS, GOS, LNnT, 6'SL, inulin, and a gum; FOS, 2'FL, LNnT, 6'SL, inulin, and a gum; GOS, 2'FL, LNnT, 6'SL, inulin, and a gum; FOS, GOS, 6'SL, inulin, and a gum; FOS, 2'FL, 6'SL, inulin, and a gum; FOS, LNnT, 6'SL, inulin, and a gum; GOS, 2'FL, 6'SL, inulin, and a gum; GOS, LNnT, 6'SL, inulin, and a gum; 2'FL, LNnT, 6'SL, inulin, and a gum; FOS, 6'SL, inulin, and a gum; GOS, 6'SL, inulin, and a gum; 2'FL, 6'SL, inulin, and a gum; LNnT, 6'SL, inulin, and a gum; FOS, GOS, 2'FL, LNnT, 3'SL, 6'SL, inulin, and polydextrose; FOS, GOS, 2'FL, 3'SL, 6'SL, inulin, and polydextrose; FOS, GOS, LNnT, 3'SL, 6'SL, inulin, and polydextrose; FOS, 2'FL, LNnT, 3'SL, 6'SL, inulin, and polydextrose; GOS, 2'FL, LNnT, 3'SL, 6'SL, inulin, and polydextrose; FOS, GOS, 3'SL, 6'SL, inulin, and polydextrose; FOS, 2'FL, 3'SL, 6'SL, inulin, and polydextrose; FOS, LNnT, 3'SL, 6'SL, inulin, and polydextrose; GOS, 2'FL, 3'SL, 6'SL, inulin, and polydextrose; GOS, LNnT, 3'SL, 6'SL, inulin, and polydextrose; 2'FL, LNnT, 3'SL, 6'SL, inulin, and polydextrose; FOS, 3'SL, 6'SL, inulin, and polydextrose; GOS, 3'SL, 6'SL, inulin, and polydextrose; 2'FL, 3'SL, 6'SL, inulin, and polydextrose; LNnT, 3'SL, 6'SL, inulin, and polydextrose; FOS, GOS, 2'FL, LNnT, 3'SL, inulin, and polydextrose; FOS, GOS, 2'FL, 3'SL, inulin, and polydextrose; FOS, GOS, LNnT, 3'SL, inulin, and polydextrose; FOS, 2'FL, LNnT, 3'SL, inulin, and polydextrose; GOS, 2'FL, LNnT, 3'SL, inulin, and polydextrose; FOS, GOS, 3'SL, inulin, and polydextrose; FOS, 2'FL, 3'SL, inulin, and polydextrose; FOS, LNnT, 3'SL, inulin, and polydextrose; GOS, 2'FL, 3'SL, inulin, and polydextrose; GOS, LNnT, 3'SL, inulin, and polydextrose; 2'FL, LNnT, 3'SL, inulin, and polydextrose; FOS, 3'SL, inulin, and polydextrose; GOS, 3'SL, inulin, and polydextrose; 2'FL, 3'SL, inulin, and polydextrose; LNnT, 3'SL, inulin, and polydextrose; FOS, GOS, 2'FL, LNnT, 6'SL, inulin, and polydextrose; FOS, GOS, 2'FL, 6'SL, inulin, and polydextrose; FOS, GOS, LNnT, 6'SL, inulin, and polydextrose; FOS, 2'FL, LNnT, 6'SL, inulin, and polydextrose; GOS, 2'FL, LNnT, 6'SL, inulin, and polydextrose; FOS, GOS, 6'SL, inulin, and polydextrose; FOS, 2'FL, 6'SL, inulin, and polydextrose; FOS, LNnT, 6'SL, inulin, and polydextrose; GOS, 2'FL, 6'SL, inulin, and polydextrose; GOS, LNnT, 6'SL, inulin, and polydextrose; 2'FL, LNnT, 6'SL, inulin, and polydextrose; FOS, 6'SL, inulin, and polydextrose; GOS, 6'SL, inulin, and polydextrose; 2'FL, 6'SL, inulin, and polydextrose; LNnT, 6'SL, inulin, and polydextrose; FOS, GOS, 2'FL, LNnT, 3'SL, 6'SL, a gum, and polydextrose; FOS, GOS, 2'FL, 3'SL, 6'SL, a gum, and polydextrose; FOS, GOS, LNnT, 3'SL, 6'SL, a gum, and polydextrose; FOS, 2'FL, LNnT, 3'SL, 6'SL, a gum, and polydextrose; GOS, 2'FL, LNnT, 3'SL, 6'SL, a gum, and polydextrose; FOS, GOS, 3'SL, 6'SL, a gum, and polydextrose; FOS, 2'FL, 3'SL, 6'SL, a gum, and polydextrose; FOS, LNnT, 3'SL, 6'SL, a gum, and polydextrose; GOS, 2'FL, 3'SL, 6'SL, a gum, and polydextrose; GOS, LNnT, 3'SL, 6'SL, a gum, and polydextrose; 2'FL, LNnT, 3'SL, 6'SL, a gum, and polydextrose; FOS, 3'SL, 6'SL, a gum, and polydextrose; GOS, 3'SL, 6'SL, a gum, and polydextrose; 2'FL, 3'SL, 6'SL, a gum, and polydextrose; LNnT, 3'SL, 6'SL, a gum, and polydextrose; FOS, GOS, 2'FL, LNnT, 3'SL, a gum, and polydextrose; FOS, GOS, 2'FL, 3'SL, a gum, and polydextrose; FOS, GOS, LNnT, 3'SL, a gum, and polydextrose; FOS, 2'FL, LNnT, 3'SL, a gum, and polydextrose; GOS, 2'FL, LNnT, 3'SL, a gum, and polydextrose; FOS, GOS, 3'SL, a gum, and polydextrose; FOS, 2'FL, 3'SL, a gum, and polydextrose; FOS, LNnT, 3'SL, a gum, and polydextrose; GOS, 2'FL, 3'SL, a gum, and polydextrose; GOS, LNnT, 3'SL, a gum, and polydextrose; 2'FL, LNnT, 3'SL, a gum, and polydextrose; FOS, 3'SL, a gum, and polydextrose; GOS, 3'SL, a gum, and polydextrose; 2'FL, 3'SL, a gum, and polydextrose; LNnT, 3'SL, a gum, and polydextrose; FOS, GOS, 2'FL, LNnT, 6'SL, a gum, and polydextrose; FOS, GOS, 2'FL, 6'SL, a gum, and polydextrose; FOS, GOS, LNnT, 6'SL, a gum, and polydextrose; FOS, 2'FL, LNnT, 6'SL, a gum, and polydextrose; GOS, 2'FL, LNnT, 6'SL, a gum, and polydextrose; FOS, GOS, 6'SL, a gum, and polydextrose; FOS, 2'FL, 6'SL, a gum, and polydextrose; FOS, LNnT, 6'SL, a gum, and polydextrose; GOS, 2'FL, 6'SL, a gum, and polydextrose; GOS, LNnT, 6'SL, a gum, and polydextrose; 2'FL, LNnT, 6'SL, a gum, and polydextrose; FOS, 6'SL, a gum, and polydextrose; GOS, 6'SL, a gum, and polydextrose; 2'FL, 6'SL, a gum, and polydextrose; LNnT, 6'SL, a gum, and polydextrose; FOS, GOS, 2'FL, LNnT, 3'SL, 6'SL, and inulin; FOS, GOS, 2'FL, 3'SL, 6'SL, and inulin; FOS, GOS, LNnT, 3'SL, 6'SL, and inulin; FOS, 2'FL, LNnT, 3'SL, 6'SL, and inulin; GOS, 2'FL, LNnT, 3'SL, 6'SL, and inulin; FOS, GOS, 3'SL, 6'SL, and inulin; FOS, 2'FL, 3'SL, 6'SL, and inulin; FOS, LNnT, 3'SL, 6'SL, and inulin; GOS, 2'FL, 3'SL, 6'SL, and inulin; GOS, LNnT, 3'SL, 6'SL, and inulin; 2'FL, LNnT, 3'SL, 6'SL, and inulin; FOS, 3'SL, 6'SL, and inulin; GOS, 3'SL, 6'SL, and inulin; 2'FL, 3'SL, 6'SL, and inulin; LNnT, 3'SL, 6'SL, and inulin; FOS, GOS, 2'FL, LNnT, 3'SL, and inulin; FOS, GOS, 2'FL, 3'SL, and inulin; FOS, GOS, LNnT, 3'SL, and inulin; FOS, 2'FL, LNnT, 3'SL, and inulin; GOS, 2'FL, LNnT, 3'SL, and inulin; FOS, GOS, 3'SL, and inulin; FOS, 2'FL, 3'SL, and inulin; FOS, LNnT, 3'SL, and inulin; GOS, 2'FL, 3'SL, and inulin; GOS, LNnT, 3'SL, and inulin; 2'FL, LNnT, 3'SL, and inulin; FOS, 3'SL, and inulin; GOS, 3'SL, and inulin; 2'FL, 3'SL, and inulin; LNnT, 3'SL, and inulin; FOS, GOS, 2'FL, LNnT, 6'SL, and inulin; FOS, GOS, 2'FL, 6'SL, and inulin; FOS, GOS, LNnT, 6'SL, and inulin; FOS, 2'FL, LNnT, 6'SL, and inulin; GOS, 2'FL, LNnT, 6'SL, and inulin; FOS, GOS, 6'SL, and inulin; FOS, 2'FL, 6'SL, and inulin; FOS, LNnT, 6'SL, and inulin; GOS, 2'FL, 6'SL, and inulin; GOS, LNnT, 6'SL, and inulin; 2'FL, LNnT, 6'SL, and inulin; FOS, 6'SL, and inulin; GOS, 6'SL, and inulin; FOS, GOS, 2'FL, LNnT, 3'SL, 6'SL, and polydextrose; FOS, GOS, 2'FL, 3'SL, 6'SL, and polydextrose; FOS, GOS, LNnT, 3'SL, 6'SL, and polydextrose; FOS, 2'FL, LNnT, 3'SL, 6'SL, and polydextrose; GOS, 2'FL, LNnT, 3'SL, 6'SL, and polydextrose; FOS, GOS, 3'SL, 6'SL, and polydextrose; FOS, 2'FL, 3'SL, 6'SL, and polydextrose; FOS, LNnT, 3'SL, 6'SL, and polydextrose; GOS, 2'FL, 3'SL, 6'SL, and polydextrose; GOS, LNnT, 3'SL, 6'SL, and polydextrose; 2'FL, LNnT, 3'SL, 6'SL, and polydextrose; FOS, 3'SL, 6'SL, and polydextrose; GOS, 3'SL, 6'SL, and polydextrose; 2'FL, 3'SL, 6'SL, and polydextrose; LNnT, 3'SL, 6'SL, and polydextrose; FOS, GOS, 2'FL, LNnT, 3'SL, and polydextrose; FOS, GOS, 2'FL, 3'SL, and polydextrose; FOS, GOS, LNnT, 3'SL, and polydextrose; FOS, 2'FL, LNnT, 3'SL, and polydextrose; GOS, 2'FL, LNnT, 3'SL, and polydextrose; FOS, GOS, 3'SL, and polydextrose; FOS, 2'FL, 3'SL, and polydextrose; FOS, LNnT, 3'SL, and polydextrose; GOS, 2'FL, 3'SL, and polydextrose; GOS, LNnT, 3'SL, and polydextrose; 2'FL, LNnT, 3'SL, and polydextrose; FOS, 3'SL, and polydextrose; GOS, 3'SL, and polydextrose; 2'FL, 3'SL, and polydextrose; LNnT, 3'SL, and polydextrose; FOS, GOS, 2'FL, LNnT, 6'SL, and polydextrose; FOS, GOS, 2'FL, 6'SL, and polydextrose; FOS, GOS, LNnT, 6'SL, and polydextrose; FOS, 2'FL, LNnT, 6'SL, and polydextrose; GOS, 2'FL, LNnT, 6'SL, and polydextrose; FOS, GOS, 6'SL, and polydextrose; FOS, 2'FL, 6'SL, and polydextrose; FOS, LNnT, 6'SL, and polydextrose; GOS, 2'FL, 6'SL, and polydextrose; GOS, LNnT, 6'SL, and polydextrose; 2'FL, LNnT, 6'SL, and polydextrose; FOS, 6'SL, and polydextrose; GOS, 6'SL, and polydextrose; 2'FL, 6'SL, and polydextrose; LNnT, 6'SL, and polydextrose; FOS, GOS, 2'FL, LNnT, 3'SL, 6'SL, and a gum; FOS, GOS, 2'FL, 3'SL, 6'SL, and a gum; FOS, GOS, LNnT, 3'SL, 6'SL, and a gum; FOS, 2'FL, LNnT, 3'SL, 6'SL, and a gum; GOS, 2'FL, LNnT, 3'SL, 6'SL, and a gum; FOS, GOS, 3'SL, 6'SL, and a gum; FOS, 2'FL, 3'SL, 6'SL, and a gum; FOS, LNnT, 3'SL, 6'SL, and a gum; GOS, 2'FL, 3'SL, 6'SL, and a gum; GOS, LNnT, 3'SL 6'SL, and a gum; 2'FL, LNnT, 3'SL, 6'SL, and a gum; FOS, 3'SL, 6'SL, and a gum; GOS, 3'SL, 6'SL, and a gum; 2'FL, 3'SL, 6'SL, and a gum; LNnT, 3'SL, 6'SL, and a gum; FOS, GOS, 2'FL, LNnT, 3'SL, and a gum; FOS, GOS, 2'FL, 3'SL, and a gum; FOS, GOS, LNnT, 3'SL, and a gum; FOS, 2'FL, LNnT, 3'SL, and a gum; GOS, 2'FL, LNnT, 3'SL, and a gum; FOS, GOS, 3'SL, and a gum; FOS, 2'FL, 3'SL, and a gum; FOS, LNnT, 3'SL, and a gum; GOS, 2'FL, 3'SL, and a gum; GOS, LNnT, 3'SL, and agum; 2'FL, LNnT, 3'SL, and a gum; FOS, 3'SL, and a gum; GOS, 3'SL, and a gum; 2'FL, 3'SL, and a gum; LNnT, 3'SL, and a gum; FOS, GOS, 2'FL, LNnT, 6'SL, and a gum; FOS, GOS, 2'FL, 6'SL, and a gum; FOS, GOS, LNnT, 6'SL, and a gum; FOS, 2'FL, LNnT, 6'SL, and a gum; GOS, 2'FL, LNnT, 6'SL, and a gum; FOS, GOS, 6'SL, and a gum; FOS, 2'FL, 6'SL, and a gum; FOS, LNnT, 6'SL, and a gum; GOS, 2'FL, 6'SL, and a gum; GOS, LNnT, 6'SL, and a gum; 2'FL, LNnT, 6'SL, and a gum; FOS, 6'SL, and a gum; GOS, 6'SL, and a gum; 2'FL, 6'SL, and a gum; and LNnT, 6'SL, and a gum.

Probiotics

The nutritional compositions of the present disclosure may, in addition to HMOs (and, optionally, other prebiotic oligosaccharides as described above), comprise one or more probiotics. In some embodiments, the nutritional composition includes a combination of HMOs and probiotics such that the composition provides a synergistic benefit to the end user in promoting the growth of microbiota in the gastrointestinal tract of infants.

Probiotics are live microorganisms thought to be healthy for the host organism. Lactic acid bacteria (LAB) and bifidobacteria are the most common types of microbes used as probiotics. Probiotics maintain the microbial ecology of the gut and show physiological, immuno-modulatory and antimicrobial effects, such that the use of probiotics has been found to prevent and treat gastrointestinal diseases and/or disorders, pathogen-induced diarrhea and toxin-producing bacteria, urogenital infections, and atopic diseases.

In order for microbes to exhibit beneficial probiotic effects in vivo, the organisms should survive for extended time periods in the gastrointestinal tract. Therefore, it is important that probiotic strains be selected that possess qualities that prevent their rapid removal by gut contraction. Effective probiotic strains are able to survive gastric conditions and colonize the intestine, at least temporarily, by adhering to the intestinal epithelium.

Non-limiting examples of probiotic strains for use in the nutritional compositions herein include the genus *Lactobacillus* including *L. acidophilus, L. amylovorus, L. brevis, L. bulgaricus, L. casei* spp. *casei, L. casei* spp. *rhamnosus, L. crispatus, L. delbrueckii* ssp. *lactis, L. fermentum, L. helveticus, L. johnsonii, L. paracasei, L. pentosus, L. plantarum, L. reuteri*, and *L. sake*; the genus *Bifidobacterium* including: *B. animalis, B. bifidum, B. breve, B. infantis*, and *B. longum*; the genus *Pediococcus* including: *P. acidilactici*; the genus *Propionibacterium* including: *P. acidipropionici, P. freudenreichii, P. jensenii*, and *P. theonii*; and the genus *Streptococcus* including: *S. cremoris, S. lactis*, and *S. thermophilus*. Particularly preferred probiotics include probiotics of human infant origin such as *B. infantis* M-63, *B. infantis* ATCC 15697, *B. infantis* 35624, *B. infantis* CHCC2228, *B. infantis* BB-02, *B. infantis* DSM20088, and *B. infantis* R0033.

The probiotic is present in the nutritional compositions in a total amount of at least about $10^3$ CFU/g, including from about $10^3$ CFU/g to about $10^{12}$ CFU/g, and including from about $10^6$ CFU/g to about $10^7$ CFU/g.

In some embodiments, the nutritional composition includes a probiotic in combination with a first oligosaccharide including fructooligosaccharide and/or a galactooligosaccharide further in combination with a second oligosaccharide including at least one HMO such as 2'FL, 3'FL, 3'SL, 6'SL, and/or LNnT. In these embodiments, the first oligosaccharide and the second oligosaccharide are present in the compositions in a weight ratio of first oligosaccharide: second oligosaccharide of about 10:1, or even from about 11:1 to about 8:1.

Macronutrients

The nutritional compositions including the HMO or HMOs may be formulated to include at least one of protein, fat, and carbohydrate. In many embodiments, the nutritional compositions will include the HMO or HMOs with protein, carbohydrate and fat.

Although total concentrations or amounts of the fat, protein, and carbohydrates may vary depending upon the product type (i.e., human milk fortifier, preterm infant formula, infant formula, toddler formula, pediatric formula, follow-on formula, adult nutritional, etc.), product form (i.e., nutritional solid, powder, ready-to-feed liquid, or concentrated liquid), and targeted dietary needs of the intended user, such concentrations or amounts most typically fall within one of the following embodied ranges, inclusive of any other essential fat, protein, and/or carbohydrate ingredients as described herein.

For the liquid preterm and term infant formulas, carbohydrate concentrations (including both HMOs and any other carbohydrate/oligosaccharide sources) most typically range from about 5% to about 40%, including from about 7% to about 30%, including from about 10% to about 25%, by weight of the preterm or term infant formula; fat concentrations most typically range from about 1% to about 30%, including from about 2% to about 15%, and also including from about 3% to about 10%, by weight of the preterm or term infant formula; and protein concentrations most typically range from about 0.5% to about 30%, including from about 1% to about 15%, and also including from about 2% to about 10%, by weight of the preterm or term infant formula.

For the liquid human milk fortifiers, carbohydrate concentrations (including both HMOs and any other carbohydrate/oligosaccharide sources) most typically range from about 10% to about 75%, including from about 10% to about 50%, including from about 20% to about 40%, by weight of the human milk fortifier; fat concentrations most typically range from about 10% to about 40%, including from about 15% to about 37%, and also including from about 18% to about 30%, by weight of the human milk fortifier; and protein concentrations most typically range from about 5% to about 40%, including from about 10% to about 30%, and also including from about 15% to about 25%, by weight of the human milk fortifier.

For the adult nutritional liquids, carbohydrate concentrations (including both HMOs and any other carbohydrate/oligosaccharide sources) most typically range from about 5% to about 40%, including from about 7% to about 30%, including from about 10% to about 25%, by weight of the adult nutritional; fat concentrations most typically range from about 2% to about 30%, including from about 3% to about 15%, and also including from about 5% to about 10%, by weight of the adult nutritional; and protein concentrations most typically range from about 0.5% to about 30%, including from about 1% to about 15%, and also including from about 2% to about 10%, by weight of the adult nutritional.

The amount of carbohydrates, fats, and/or proteins in any of the liquid nutritional compositions described herein may also be characterized in addition to, or in the alternative, as a percentage of total calories in the liquid nutritional composition as set forth in the following table. These macronutrients for liquid nutritional compositions of the present disclosure are most typically formulated within any of the caloric ranges (embodiments A-F) described in the following table (each numerical value is preceded by the term "about").

| Nutrient % Total | Embodiment A | Embodiment B | Embodiment C |
|---|---|---|---|
| Carbohydrate | 0-98 | 2-96 | 10-75 |
| Protein | 0-98 | 2-96 | 5-70 |
| Fat | 0-98 | 2-96 | 20-85 |
| | Embodiment D | Embodiment E | Embodiment F |
| Carbohydrate | 30-50 | 25-50 | 25-50 |
| Protein | 15-35 | 10-30 | 5-30 |
| Fat | 35-55 | 1-20 | 2-20 |

In one specific example, liquid infant formulas (both ready-to-feed and concentrated liquids) include those embodiments in which the protein component may comprise from about 7.5% to about 25% of the caloric content of the formula; the carbohydrate component (including both HMOs and any other carbohydrate/oligosaccharide sources) may comprise from about 35% to about 50% of the total caloric content of the infant formula; and the fat component may comprise from about 30% to about 60% of the total caloric content of the infant formula. These ranges are provided as examples only, and are not intended to be limiting. Additional suitable ranges are noted in the following table (each numerical value is preceded by the term "about").

| Nutrient % Total | Embodiment G | Embodiment H | Embodiment I |
| --- | --- | --- | --- |
| Carbohydrates: | 20-85 | 30-60 | 35-55 |
| Fat: | 5-70 | 20-60 | 25-50 |
| Protein: | 2-75 | 5-50 | 7-40 |

When the nutritional composition is a powdered preterm or term infant formula, the protein component is present in an amount of from about 5% to about 35%, including from about 8% to about 12%, and including from about 10% to about 12% by weight of the preterm or term infant formula; the fat component is present in an amount of from about 10% to about 35%, including from about 25% to about 30%, and including from about 26% to about 28% by weight of the preterm or term infant formula; and the carbohydrate component (including both HMOs and any other carbohydrate/oligosaccharide sources) is present in an amount of from about 30% to about 85%, including from about 45% to about 60%, including from about 50% to about 55% by weight of the preterm or term infant formula.

For powdered human milk fortifiers, the protein component is present in an amount of from about 1% to about 55%, including from about 10% to about 50%, and including from about 10% to about 30% by weight of the human milk fortifier; the fat component is present in an amount of from about 1% to about 30%, including from about 1% to about 25%, and including from about 1% to about 20% by weight of the human milk fortifier; and the carbohydrate component (including both HMOs and any other carbohydrate/oligosaccharide sources) is present in an amount of from about 15% to about 75%, including from about 15% to about 60%, including from about 20% to about 50% by weight of the human milk fortifier.

For powdered adult nutritionals, the protein component is present in an amount of from about 10% to about 90%, including from about 30% to about 80%, and including from about 40% to about 75% by weight of the adult nutritional; the fat component is present in an amount of from about 0.5% to about 20%, including from about 1% to about 10%, and including from about 2% to about 5% by weight of the adult nutritional; and the carbohydrate component (including both HMOs and any other carbohydrate/oligosaccharide sources) is present in an amount of from about 5% to about 40%, including from about 7% to about 30%, including from about 10% to about 25% by weight of the adult nutritional.

The total amount or concentration of fat, carbohydrate, and protein, in the powdered nutritional compositions of the present disclosure can vary considerably depending upon the selected composition and dietary or medical needs of the intended user. Additional suitable examples of macronutrient concentrations are set forth below. In this context, the total amount or concentration refers to all fat, carbohydrate, and protein sources in the powdered composition. For powdered nutritional compositions, such total amounts or concentrations are most typically and preferably formulated within any of the embodied ranges described in the following table (each numerical value is preceded by the term "about").

| Nutrient % Total | Embodiment J | Embodiment K | Embodiment L |
| --- | --- | --- | --- |
| Carbohydrate | 1-85 | 30-60 | 35-55 |
| Fat | 5-70 | 20-60 | 25-50 |
| Protein | 2-75 | 5-50 | 7-40 |

The nutritional compositions of the present disclosure may optionally comprise any source or sources of fat. Suitable sources of fat for use herein include any fat or fat source that is suitable for use in an oral nutritional composition and is compatible with the essential elements and features of such composition. For example, in one specific embodiment, the fat is derived from long chain polyunsaturated fatty acids (LCPUFAs).

Exemplary LCPUFAs for use in the nutritional compositions include, for example, w-3 LCPUFAs and w-6 LCPUFAs. Specific LCPUFAs include docosahexaenoic acid (DHA), eicosapentaenoic acid (EPA), docosapentaenoic acid (DPA), arachidonic acid (ARA), linoleic acid, linolenic acid (alpha linolenic acid) and gamma-linolenic acid derived from oil sources such as plant oils, marine plankton, fungal oils, and fish oils. In one particular embodiment, the LCPUFAs are derived from fish oils such as menhaden, salmon, anchovy, cod, halibut, tuna, or herring oil. Particularly preferred LCPUFAs for use in the nutritional compositions with the HMOs include DHA, ARA, EPA, DPA, and combinations thereof.

In order to reduce potential side effects of high dosages of LCPUFAs in the nutritional compositions, the content of LCPUFAs preferably does not exceed 3% by weight of the total fat content, including below 2% by weight of the total fat content, and including below 1% by weight of the total fat content in the nutritional composition.

The LCPUFA may be provided as free fatty acids, in triglyceride form, in diglyceride form, in monoglyceride form, in phospholipid form, in esterfied form or as a mixture of one or more of the above, preferably in triglyceride form. In another specific embodiment, the fat is derived from short chain fatty acids.

Additional non-limiting examples of suitable fats or sources thereof for use in the nutritional compositions described herein include coconut oil, fractionated coconut oil, soybean oil, corn oil, olive oil, safflower oil, high oleic safflower oil, oleic acids (EMERSOL 6313 OLEIC ACID, Cognis Oleochemicals, Malaysia), MCT oil (medium chain triglycerides), sunflower oil, high oleic sunflower oil, palm and palm kernel oils, palm olein, canola oil, marine oils, fish oils, fungal oils, algae oils, cottonseed oils, and combinations thereof.

Protein

The nutritional compositions of the present disclosure may optionally further comprise protein. Any protein source that is suitable for use in oral nutritional compositions and is compatible with the essential elements and features of such compositions is suitable for use in the nutritional compositions.

Non-limiting examples of suitable proteins or sources thereof for use in the nutritional compositions include hydrolyzed, partially hydrolyzed or non-hydrolyzed proteins or protein sources, which may be derived from any known or otherwise suitable source such as milk (e.g., casein, whey), animal (e.g., meat, fish), cereal (e.g., rice, corn), vegetable (e.g., soy) or combinations thereof. Non-limiting examples of such proteins include milk protein isolates, milk protein concentrates asdescribed herein, casein protein isolates, extensively hydrolyzed casein, whey protein, sodium or calcium caseinates, whole cow milk, partially or completely defatted milk, soy protein isolates, soy protein concentrates, and so forth. In one specific embodiment, the nutritional compositions include a protein source derived from milk proteins of human and/or bovine origin.

In one embodiment, the protein source is a hydrolyzed protein hydrolysate. In this context, the terms "hydrolyzed protein" or "protein hydrolysates" are used interchangeably herein and include extensively hydrolyzed proteins, wherein the degree of hydrolysis is most often at least about 20%, including from about 20% to about 80%, and also including from about 30% to about 80%, even more preferably from about 40% to about 60%. The degree of hydrolysis is the extent to which peptide bonds are broken by a hydrolysis method. The degree of protein hydrolysis for purposes of characterizing the extensively hydrolyzed protein component of these embodiments is easily determined by one of ordinary skill in the formulation arts by quantifying the amino nitrogen to total nitrogen ratio (AN/TN) of the protein component of the selected liquid formulation. The amino nitrogen component is quantified by USP titration methods for determining amino nitrogen content, while the total nitrogen component is determined by the Tecator Kjeldahl method, all of which are well known methods to one of ordinary skill in the analytical chemistry art.

Suitable hydrolyzed proteins may include soy protein hydrolysate, casein protein hydrolysate, whey protein hydrolysate, rice protein hydrolysate, potato protein hydrolysate, fish protein hydrolysate, egg albumen hydrolysate, gelatin protein hydrolysate, combinations of animal and vegetable protein hydrolysates, and combinations thereof Particularly preferred protein hydrolysates include whey protein hydrolysate and hydrolyzed sodium caseinate.

When used in the nutritional compositions, the protein source may include at least about 20% (by weight total protein) protein hydrolysate, including from about 30% to 100% (by weight total protein) protein hydrolysate, and including from about 40% to about 80% (by weight total protein) protein hydrolysate, and including about 50% (by weight total protein) protein hydrolysate. In one particularembodiment, the nutritional composition includes 100% (by weight total protein) protein hydrolysate.

Carbohydrate

The nutritional compositions of the present disclosure may further optionally comprise any carbohydrates that are suitable for use in an oral nutritional composition and are compatible with the essential elements and features of such compositions.

Non-limiting examples of suitable carbohydrates or sources thereof for use in the nutritional compositions described herein may include maltodextrin, hydrolyzed or modified starch or cornstarch, glucose polymers, corn syrup, corn syrup solids, rice-derived carbohydrates, pea-derived carbohydrates, potato-derived carbohydrates, tapioca, sucrose, glucose, fructose, lactose, high fructose corn syrup, honey, sugar alcohols (e.g., maltitol, erythritol, sorbitol), artificial sweeteners (e.g., sucralose, acesulfame potassium, stevia) and combinations thereof A particularly desirable carbohydrate is a low dextrose equivalent (DE) maltodextrin.

Other Optional Ingredients

The nutritional compositions of the present disclosure may further comprise other optional components that may modify the physical, chemical, aesthetic or processing characteristics of the compositions or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include preservatives, emulsifying agents, buffers, pharmaceutical actives, anti-inflammatory agents, additional nutrients as described herein, colorants, flavors, thickening agents and stabilizers, emulsifying agents, lubricants, and so forth.

The nutritional compositions may further comprise a sweetening agent, preferably including at least one sugar alcohol such as maltitol, erythritol, sorbitol, xylitol, mannitol, isolmalt, and lactitol, and also preferably including at least one artificial or high potency sweetener such as acesulfame K, aspartame, sucralose, saccharin, stevia, and tagatose. These sweetening agents, especially as a combination of a sugar alcohol and an artificial sweetener, are especially useful in formulating liquid beverage embodiments of the present disclosure having a desirable favor profile. These sweetener combinations are especially effective in masking undesirable flavors sometimes associated with the addition of vegetable proteins to a liquid beverage. Optional sugar alcohol concentrations in the nutritional composition may range from at least 0.01%, including from 0.1% to about 10%, and also including from about 1% to about 6%, by weight of the nutritional composition. Optional artificial sweetener concentrations may range from about 0.01%, including from about 0.05% to about 5%, also including from about 0.1% to about 1.0%, by weight of the nutritional composition.

A flowing agent or anti-caking agent may be included in the nutritional compositions as described herein to retard clumping or caking of the powder over time and to make a powder embodiment flow easily from its container. Any known flowing or anti-caking agents that are known or otherwise suitable for use in a nutritional powder or product form are suitable for use herein, non-limiting examples of which include tricalcium phosphate, silicates, and combinations thereof. The concentration of the flowing agent or anti-caking agent in the nutritional composition varies depending upon the product form, the other selected ingredients, the desired flow properties, and so forth, but most typically range from about 0.1% to about 4%, including from about 0.5% to about 2%, by weight of the nutritional composition.

A stabilizer may also be included in the nutritional compositions. Any stabilizer that is known or otherwise suitable for use in a nutritional composition is also suitable for use herein, some non-limiting examples of which include gums such as xanthan gum. The stabilizer may represent from about 0.1% to about 5.0%, including from about 0.5% to about 3%, including from about 0.7% to about 1.5%, by weight of the nutritional composition.

Additionally, the nutritional compositions may comprise one or more antioxidants to provide nutritional support, as well as to reduce oxidative stress. Any antioxidants suitable for oral administration may be included for use in the nutritional compositions of the present disclosure, including, for example, vitamin A, vitamin E, vitamin C, retinol, tocopherol, and carotenoids.

In one specific embodiment, the antioxidants for use in the nutritional compositions include carotenoids such as lutein, zeaxanthin, lycopene, beta-carotene, and combinations thereof, and particularly, combinations of the carotenoids lutein, lycopene, and beta-carotene. Nutritional compositions containing these combinations, as selected and defined herein, can be used to modulate inflammation and/or levels of C-reactive protein in preterm and term infants.

The nutritional compositions may further comprise any of a variety of other vitamins or related nutrients, non-limiting examples of which include vitamin D, vitamin K, thiamine, riboflavin, pyridoxine, vitamin B12, niacin, folic acid, pantothenic acid, biotin, choline, inositol, salts and derivatives thereof, and combinations thereof.

The nutritional compositions may further comprise any of a variety of other additional minerals, non-limiting examples of which include calcium, phosphorus, magnesium, iron, zinc, manganese, copper, sodium, potassium, molybdenum, chromium, chloride, and combinations thereof.

The nutritional compositions of the present disclosure may additionally comprise nucleotides and/or nucleotide precursors selected from the group consisting of nucleoside, purine base, pyrimidine base, ribose and deoxyribose to further improve intestinal barrier integrity and/or maturation. The nucleotide may be in monophosphate, diphosphate, or triphosphate form. The nucleotide may be a ribonucleotide or a deoxyribonucleotide. The nucleotides may be monomeric, dimeric, or polymeric (including RNA and DNA). The nucleotide may be present in the nutritional composition as a free acid or in the form of a salt, preferably a monosodium salt.

Suitable nucleotides and/or nucleosides for use in the nutritional compositions include one or more of cytidine 5'-monophosphate, uridine 5'-monophosphate, adenosine 5'-monophosphate, guanosine 5'-1-monophosphate, and/or inosine 5'-monophosphate, more preferably cytidine 5'-monophosphate, uridine 5'-monophosphate, adenosine 5'-monophosphate, guanosine 5'-monophosphate, and inosine 5'-monophosphate.

Methods of Manufacture

The nutritional compositions of the present disclosure may be prepared by any known or otherwise effective manufacturing technique for preparing the selected product solid or liquid form. Many such techniques are known for any given product form such as nutritional liquids or powders and can easily be applied by one of ordinary skill in the art to the nutritional compositions described herein.

The nutritional compositions of the present disclosure can therefore be prepared by any of a variety of known or otherwise effective formulation or manufacturing methods. In one suitable manufacturing process, for example, at least three separate slurries are prepared, including a protein-in-fat (PIF) slurry, a carbohydrate-mineral (CHO-MN) slurry, and a protein-in-water (PIW) slurry. The PIF slurry is formed by heating and mixing the oil (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MIN slurry is formed by adding with heated agitation to water: minerals (e.g., potassium citrate, dipotassium phosphate, sodium citrate, etc.), trace and ultra trace minerals (TM/UTM premix), thickening or suspending agents (e.g. avicel, gellan, carrageenan). The resulting CHO-MIN slurry is held for 10 minutes with continued heat and agitation before adding additional minerals (e.g., potassium chloride, magnesium carbonate, potassium iodide, etc.), and/or carbohydrates (e.g., HMOs, fructooligosaccharide, sucrose, corn syrup, etc.). The PIW slurry is then formed by mixing with heat and agitation the remaining protein, if any.

The resulting slurries are then blended together with heated agitation and the pH adjusted to 6.6-7.0, after which the composition is subjected to high-temperature short-time (HTST) processing during which the composition is heat treated, emulsified and homogenized, and then allowed to cool. Water soluble vitamins and ascorbic acid are added, the pH is adjusted to the desired range if necessary, flavors are added, and water is added to achieve the desired total solid level. The composition is then aseptically packaged to form an aseptically packaged nutritional emulsion. This emulsion can then be further diluted, heat-treated, and packaged to form a ready-to-feed or concentrated liquid, or it can be heat-treated and subsequently processed and packaged as a reconstitutable powder, e.g., spray dried, drymixed, agglomerated.

The nutritional solid, such as a spray dried nutritional powder or drymixed nutritional powder, may be prepared by any collection of known or otherwise effective techniques, suitable for making and formulating a nutritional powder.

For example, when the nutritional powder is a spray dried nutritional powder, the spray drying step may likewise include any spray drying technique that is known for or otherwise suitable for use in the production of nutritional powders. Many different spray drying methods and techniques are known for use in the nutrition field, all of which are suitable for use in the manufacture of the spray dried nutritional powders herein.

One method of preparing the spray dried nutritional powder comprises forming and homogenizing an aqueous slurry or liquid comprising predigested fat, and optionally protein, carbohydrate, and other sources of fat, and then spray drying the slurry or liquid to produce a spray dried nutritional powder. The method may further comprise the step of spray drying, drymixing, or otherwise adding additional nutritional ingredients, including any one or more of the ingredients described herein, to the spray dried nutritional powder.

Other suitable methods for making nutritional compositions are described, for example, in U.S. Pat. No. 6,365,218 (Borschel, et al.), U.S. Pat. No. 6,589,576 (Borschel, et al.), U.S. Pat. No. 6,306,908 (Carlson, et al.), U.S. Patent Application No. 20030118703 A1 (Nguyen, et al.), which descriptions are incorporated herein by reference to the extent that they are consistent herewith.

Methods of Use

The nutritional compositions as described herein can be used to address one or more of the diseases, disorders, or conditions discussed herein, or can be used to provide one or more of the benefits described herein, to preterm infants, infants, toddlers, children, and adults, including pregnant women. The preterm infant, infant, toddler, child, adult and pregnant women utilizing the nutritional compositions described herein may actually have or be afflicted with the disease or condition described, or may be susceptible to, or at risk of, getting the disease or condition (that is, may not actually yet have the disease or condition, but is at elevated risk as compared to the general population for getting it due to certain conditions, family history, etc.) Whether the preterm infant, infant, toddler, child, adult, and pregnant women actually have the disease or condition, or is at risk or susceptible to the disease or condition, the preterm infant, infant, toddler, child, adult, and pregnant women are classified herein as "in need of assistance in dealing with and combating the disease or condition. For example, the preterm infant, infant, toddler, child, adult and pregnant women may actually have respiratory inflammation or may be at risk of getting respiratory inflammation (susceptible to getting respiratory inflammation) due to family history or other medical conditions, for example. Whether the preterm infant, infant, toddler, child, adult, and pregnant women actually has the disease or condition, or is only at risk or susceptible to getting the disease or condition, it is within the scope of the present disclosure to assist the preterm infant, infant, toddler, child, adult and pregnant women with the nutritional compositions described herein.

Based on the foregoing, because some of the method embodiments of the present disclosure are directed to specific subsets or subclasses of identified individuals (that is, the subset or subclass of individuals "in need" of assistance in addressing one or more specific diseases or specific conditions noted herein), not all preterm infants, infants, toddlers, children, adults and pregnant women will fall within the subset or subclass of preterm infants, infants, toddlers, children, adults, and pregnant women as described herein for certain diseases or conditions.

The nutritional compositions as described herein comprise HMOs, alone or in combination with one or more additional components, to provide a nutritional source for improving at least the intestinal/gut function. Specifically, the nutritional compositions can stimulate enteric nerve cells in the gastrointestinal tract of an individual to improve intestinal/gut barrier integrity; improve feeding tolerance (e.g., reduced diarrhea, loose stools, gas, and bloating); reduce colic in infants; protect against necrotizing enterocolitis and other disorders of prematurity; address gastrointestinal diseases and disorders associated with the enteric nervous system; address gastrointestinal diseases and disorders of gut contractility and inflammation; correct effects of gut dysbiosis; and affect long-term modulation of allergic tolerance.

More particularly, in some embodiments, the nutritional compositions may be administered to an individual having, susceptible to, or at risk of, gastrointestinal diseases and disorders associated with the enteric nervous system and/or associated with gut contractility and inflammation, which may include, for example, irritable bowel syndrome, colitis (e.g., necrotizing enterocolitis, Crohn's disease, ischemic colitis, cryptosporidium enterocolitis, pseudomembranous colitis, cytomegalovirus, ulcerative colitis), food intolerance, and food allergies.

Along with improved growth and maturation of an individual's immune system as described above, the use of the nutritional compositions of the present disclosure may also function to enhance the individual's ability to resist microbial infection and to promote the growth of beneficial microbiota in the gastrointestinal tract of an infant, toddler, child, or adult.

Further, when used in combination with LCPUFAs and/or antioxidants, and particularly, with carotenoids, the HMOs can reduce oxidative stress, which is a metabolic condition in which there is an increased production and accumulation of oxidized biomolecules such as lipid peroxides and their catabolites, protein carbonyls, and oxidatively damaged DNA. The outcomes of oxidative stress range from unwanted changes in metabolism to inflammation and cell and tissue death. Accordingly, by reducing the incidence of unregulated inflammation and oxidation in the infant, damage to the tissue lining and cell death is reduced, further reducing the incidence of inflammatory diseases, such as necrotizing enterocolitis (NEC).

Additionally, the nutritional compositions of the present disclosure may also be used to improve cognition in individuals, particularly in individuals susceptible to, or at risk of, neurodegenerative diseases, which may include, for example, Alzheimer's disease, Huntington's disease, Parkinson's disease, and schizophrenia, or in individuals suffering from conditions caused by impaired cognitive development or neurodevelopmental conditions, such as attention deficit hyperactivity disorder and autism.

EXAMPLES

The following examples illustrate specific embodiments and/or features of the nutritional compositions and methods of the present disclosure. The examples are given solely for the purpose of illustration and are not to be construed as limitations of the present disclosure, as many variations thereof are possible without departing from the spirit and scope of the disclosure. All exemplified amounts are weight percentages based upon the total weight of the composition, unless otherwise specified.

The exemplified compositions are shelf stable nutritional compositions prepared in accordance with the manufacturing methods described herein, such that each exemplified composition, unless otherwise specified, includes an aseptically processed embodiment and a retort packaged embodiment.

The nutritional liquid embodiments are aqueous oil-in-water emulsions that are packaged in 240 mL plastic containers and remain physically stable for 12-18 months after composition/packaging at storage temperatures ranging from 1-25° C.

Examples 1-5

Examples 1-5 illustrate ready-to-feed nutritional emulsions of the present disclosure, the ingredients of which are listed in the table below. All ingredient amounts are listed as kilogram per 1000 kilogram batch of product, unless otherwise specified.

| Ingredient | Ex. 1 | Ex. 2 | Ex. 3 | Ex. 4 | Ex. 5 |
|---|---|---|---|---|---|
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| 2' fucosyllactose (2'FL) | 0.1896 | 0.1801 | 0.1706 | 0.1991 | 0.2086 |
| Galactooligosaccharides (GOS) | 8.630 | 8.630 | 8.630 | 8.630 | 8.630 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 445.28 g | 445.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |

-continued

| Ingredient | Ex. 1 | Ex. 2 | Ex. 3 | Ex. 4 | Ex. 5 |
|---|---|---|---|---|---|
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, $D_3$, E, $K_1$ premix | 47.40 g | 47.40 g | 47.40 g | 47.40 g | 47.40 g |
| Citric acid | 29.77 g | 29.77 g | 29.77 g | 29.77 g | 29.77 g |
| Probiotic | 1.0 | 1.0 | 1.0 | 1.0 | 1.0 |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 6-10

Examples 6-10 illustrate ready-to-feed nutritional emulsions of the present disclosure, the ingredients of which are listed in the table below. All ingredient amounts are listed as kilogram per 1000 kilogram batch of product, unless otherwise specified.

Examples 11-15

Examples 11-15 illustrate concentrated liquid emulsions of the present disclosure, the ingredients of which are listed in the table below. All ingredient amounts are listed as kilogram per 1000 kilogram batch of product, unless otherwise specified.

| Ingredient | Ex. 6 | Ex. 7 | Ex. 8 | Ex. 9 | Ex. 10 |
|---|---|---|---|---|---|
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| 2'-fucosyllactose (2'FL) | 0.0948 | 0.09005 | 0.0853 | 0.0995 | 0.1043 |
| Lacto-N-neotetraose (LNnT) | 0.0948 | 0.09005 | 0.0853 | 0.0995 | 0.1043 |
| Galactooligosaccharides (GOS) | 8.630 | 8.630 | 8.630 | 8.630 | 8.630 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, $D_3$, E, $K_1$ premix | 47.40 g | 47.40 g | 47.40 g | 47.40 g | 47.40 g |
| Citric acid | 29.77 g | 29.77 g | 29.77 g | 29.77 g | 29.77 g |
| Probiotic | 1.0 | 0.95 | 0.90 | 1.05 | 1.10 |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

| Ingredient | Ex. 11 | Ex. 12 | Ex. 13 | Ex. 14 | Ex. 15 |
| --- | --- | --- | --- | --- | --- |
| Water | Q.S. | Q.S. | Q.S. | Q.S. | Q.S. |
| Condensed Skim Milk | 166.6 | 166.6 | 166.6 | 166.6 | 166.6 |
| Lactose | 106.1 | 106.1 | 106.1 | 106.1 | 106.1 |
| High oleic safflower oil | 27.16 | 27.16 | 27.16 | 27.16 | 27.16 |
| Soybean oil | 20.42 | 20.42 | 20.42 | 20.42 | 20.42 |
| Coconut oil | 19.48 | 19.48 | 19.48 | 19.48 | 19.48 |
| 2' fucosyllactose (2'FL) | 0.1896 | 0.1188 | 0.0853 | 0.2414 | 0.2560 |
| Galactooligosaccharides (GOS) | 16.71 | 16.71 | 16.71 | 16.71 | 16.71 |
| Whey protein concentrate | 12.20 | 12.20 | 12.20 | 12.20 | 12.20 |
| Potassium citrate | 894.5 g | 894.5 g | 894.5 g | 894.5 g | 894.5 g |
| Calcium carbonate | 1.072 | 1.072 | 1.072 | 1.072 | 1.072 |
| Monoglycerides | 690.0 g | 690.0 g | 690.0 g | 690.0 g | 690.0 g |
| Soy lecithin | 690.0 g | 690.0 g | 690.0 g | 690.0 g | 690.0 g |
| ARA oil | 684.2 g | 684.2 g | 684.2 g | 684.2 g | 684.2 g |
| Nucleotide/chloride premix | 568.9 g | 568.9 g | 568.9 g | 568.9 g | 568.9 g |
| Potassium chloride | 480.8 g | 480.8 g | 480.8 g | 480.8 g | 480.8 g |
| Ascorbic acid | 958.6 g | 958.6 g | 958.6 g | 958.6 g | 958.6 g |
| Vitamin mineral premix | 276.9 g | 276.9 g | 276.9 g | 276.9 g | 276.9 g |
| DHA oil | 256.1 g | 256.1 g | 256.1 g | 256.1 g | 256.1 g |
| Carrageenan | 200.0 g | 200.0 g | 200.0 g | 200.0 g | 200.0 g |
| Magnesium chloride | 174.7 g | 174.7 g | 174.7 g | 174.7 g | 174.7 g |
| Ferrous sulfate | 112.7 g | 112.7 g | 112.7 g | 112.7 g | 112.7g |
| Choline chloride | 104.8 g | 104.8 g | 104.8 g | 104.8 g | 104.8 g |
| Vitamin A, $D_3$, E, $K_1$ premix | 86.90 g | 86.90 g | 86.90 g | 86.90 g | 86.90 g |
| Citric acid | 64.55 g | 64.55 g | 64.55 g | 64.55 g | 64.55 g |
| Mixed carotenoid premix | 45.63 g | 45.63 g | 45.63 g | 45.63 g | 45.63 g |
| Sodium chloride | AN | AN | AN | AN | AN |
| L-carnitine | 6.371 g | 6.371 g | 6.371 g | 6.371 g | 6.371 g |
| Riboflavin | 2.921 g | 2.921 g | 2.921 g | 2.921 g | 2.921 g |
| Vitamin A Palmitate | 1.504 g | 1.504 g | 1.504 g | 1.504 g | 1.504 g |
| Potassium hydroxide | 659.8 g | 659.8 g | 659.8 g | 659.8 g | 659.8 g |
| Tricalcium phosphate | AN | AN | AN | AN | AN |
| Potassium phosphate | AN | AN | AN | AN | AN |

AN = as needed

Examples 16-20

Examples 16-20 illustrate spray dried nutritional powders of the present disclosure, the ingredients of which are listed in the table below. All ingredient amounts are listed as kilogram per 1000 kilogram batch of product, unless otherwise specified.

| Ingredient | Ex. 16 | Ex. 17 | Ex. 18 | Ex. 19 | Ex. 20 |
| --- | --- | --- | --- | --- | --- |
| Nonfat dry milk | 456.9 | 456.9 | 456.9 | 456.9 | 456.9 |
| Lactose | 259.0 | 259.0 | 259.0 | 259.0 | 259.0 |
| High oleic sunflower oil | 93.9 | 93.9 | 93.9 | 93.9 | 93.9 |
| Soy oil | 70.4 | 70.4 | 70.4 | 70.4 | 70.4 |
| Coconut oil | 67.1 | 67.1 | 67.1 | 67.1 | 67.1 |
| 2' fucosyllactose (2'FL) | 0.7584 | 0.7204 | 0.6824 | 0.7964 | 0.8344 |
| Galactooligosaccharide (GOS) | 53.5 | 53.5 | 53.5 | 53.5 | 53.5 |
| Probiotic | 1.0 | 0.95 | 0.90 | 1.05 | 1.10 |
| Flavoring agent | 6.2 | 6.2 | 6.2 | 6.2 | 6.2 |
| Calcium carbonate | 4.8 | 4.8 | 4.8 | 4.8 | 4.8 |
| Potassium citrate | 4.7 | 4.7 | 4.7 | 4.7 | 4.7 |
| Oligofructose (FOS) | 2.9 | 2.9 | 2.9 | 2.9 | 2.9 |
| Ascorbic acid | 2.0 | 2.0 | 2.0 | 2.0 | 2.0 |
| Nucleotide/Choline Premix | 1.8 | 1.8 | 1.8 | 1.8 | 1.8 |
| ARA oil | 1.8 | 1.8 | 1.8 | 1.8 | 1.8 |
| Vitamin/Trace Mineral Premix | 1.5 | 1.5 | 1.5 | 1.5 | 1.5 |
| Sodium chloride | 1.3 | 1.3 | 1.3 | 1.3 | 1.3 |
| Lecithin | 1.2 | 1.2 | 1.2 | 1.2 | 1.2 |
| Sodium citrate | 982.2 g | 982.2 g | 982.2 g | 982.2 g | 982.2 g |
| DHA oil | 882.1 g | 882.1 g | 882.1 g | 882.1 g | 882.1 g |
| Magnesium chloride | 477.4 g | 477.4 g | 477.4 g | 477.4 g | 477.4 g |
| Vitamin A, D3, E, K1 Premix | 314.7 g | 314.7 g | 314.7 g | 314.7 g | 314.7 g |
| Ascorbyl Palmitate | 278.8 g | 278.8 g | 278.8 g | 278.8 g | 278.8 g |
| Antioxidant | 137.3 g | 137.3 g | 137.3 g | 137.3 g | 137.3 g |
| Tocopheryl acetate | 32.0 g | 32.0 g | 32.0 g | 32.0 g | 32.0 g |
| Beta-carotene 30% | 11.0 g | 11.0 g | 11.0 g | 11.0 g | 11.0 g |
| Potassium iodide | 2.5 g | 2.5 g | 2.5 g | 2.5 g | 2.5 g |
| Riboflavin | 2.0 g | 2.0 g | 2.0 g | 2.0 g | 2.0 g |
| Magnesium sulfate | 499.5 mg | 499.5 mg | 499.5 mg | 499.5 mg | 499.5 mg |

-continued

| Ingredient | Ex. 16 | Ex. 17 | Ex. 18 | Ex. 19 | Ex. 20 |
|---|---|---|---|---|---|
| Potassium phosphate dibasic | AN | AN | AN | AN | AN |
| Potassium chloride | AN | AN | AN | AN | AN |
| Tricalcium phosphate | AN | AN | AN | AN | AN |
| Potassium hydroxide | AN | AN | AN | AN | AN |
| Calcium hydroxide | AN | AN | AN | AN | AN |
| Sodium hydroxide | AN | AN | AN | AN | AN |
| Water | Q.S. | Q.S. | Q.S. | Q.S. | Q.S. |

AN = as needed

Examples 21-25

Examples 21-25 illustrate spray dried nutritional powders of the present disclosure, the ingredients of which are listed in the table below. All ingredient amounts are listed as kilogram per 1000 kilogram batch of product, unless otherwise specified.

| Ingredient | Ex. 21 | Ex. 22 | Ex. 23 | Ex. 24 | Ex. 25 |
|---|---|---|---|---|---|
| Water | Q.S. | Q.S. | Q.S. | Q.S. | Q.S. |
| Corn syrup | 308.9 | 308.9 | 308.9 | 308.9 | 308.9 |
| Maltodextrin | 297.1 | 297.1 | 297.1 | 297.1 | 297.1 |
| Sucrose | 112.4 | 112.4 | 112.4 | 112.4 | 112.4 |
| High Oleic sunflower oil | 84.9 | 84.9 | 84.9 | 84.9 | 84.9 |
| Sodium caseinate | 73.0 | 73.0 | 73.0 | 73.0 | 73.0 |
| Calcium caseinate | 50.2 | 50.2 | 50.2 | 50.2 | 50.2 |
| 2' fucosyllactose (2'FL) | 0.7584 | 0.7204 | 0.6824 | 0.7964 | 0.8344 |
| Inulin oligofructose | 47.0 | 47.0 | 47.0 | 47.0 | 47.0 |
| Soy oil | 38.3 | 38.3 | 38.3 | 38.3 | 38.3 |
| Isolated soy protein | 35.9 | 35.9 | 35.9 | 35.9 | 35.9 |
| Milk protein isolate | 16.3 | 16.3 | 16.3 | 16.3 | 16.3 |
| Canola oil | 13.7 | 13.7 | 13.7 | 13.7 | 13.7 |
| Sodium citrate | 9.8 | 9.8 | 9.8 | 9.8 | 9.8 |
| Potassium citrate | 9.7 | 9.7 | 9.7 | 9.7 | 9.7 |
| Tricalcium phosphate | 9.0 | 9.0 | 9.0 | 9.0 | 9.0 |
| Flavoring agent | 7.3 | 7.3 | 7.3 | 7.3 | 7.3 |
| Magnesium chloride | 6.2 | 6.2 | 6.2 | 6.2 | 6.2 |
| Potassium chloride | 5.5 | 5.5 | 5.5 | 5.5 | 5.5 |
| Choline chloride | 1.7 | 1.7 | 1.7 | 1.7 | 1.7 |
| Vitamin premix | 950.0 g | 950.0 g | 950.0 g | 950.0 g | 950.0 g |
| Ascorbic acid | 755.0 g | 755.0 g | 755.0 g | 755.0 g | 755.0 g |
| Vitamin/trace mineral premix | 465.0 g | 465.0 g | 465.0 g | 465.0 g | 465.0 g |
| Potassium hydroxide | 215.9 g | 215.9 g | 215.9 g | 215.9 g | 215.9 g |
| Potassium phosphate dibasic | 185.8 g | 185.8 g | 185.8 g | 185.8 g | 185.8 g |
| Ascorbyl palmitate | 164.7 g | 164.7 g | 164.7 g | 164.7 g | 164.7 g |
| Antioxidant | 82.3 g | 82.3 g | 82.3 g | 82.3 g | 82.3 g |
| Vitamin A, D3, E, K1 premix | 82.3 g | 82.3 g | 82.3 g | 82.3 g | 82.3 g |
| Vitamin A palmitate | 16.5 g | 16.5 g | 16.5 g | 16.5 g | 16.5 g |
| Ferrous sulfate | 12.0 g | 12.0 g | 12.0 g | 12.0 g | 12.0 g |
| Beta carotene 30% | 5.5 g | 5.5 g | 5.5 g | 5.5 g | 5.5 g |
| Vitamin D3 oil | 1.0 g | 1.0 g | 1.0 g | 1.0 g | 1.0 g |
| Potassium iodide | 800.0 mg | 800.0 mg | 800.0 mg | 800.0 mg | 800.0 mg |
| Citric acid | AN | AN | AN | AN | AN |
| Potassium hydroxide 40% | AN | AN | AN | AN | AN |
| Maltodextrin | AN | AN | AN | AN | AN |
| Magnesium sulfate | AN | AN | AN | AN | AN |
| Sodium chloride | AN | AN | AN | AN | AN |
| Calcium carbonate | AN | AN | AN | AN | AN |

AN = as needed

Examples 26-30

Examples 26-30 illustrate ready-to-feed nutritional emulsions of the present disclosure, the ingredients of which are listed in the table below. All ingredient amounts are listed as kilogram per 1000 kilogram batch of product, unless otherwise specified.

| Ingredient | Ex. 26 | Ex. 27 | Ex. 28 | Ex. 29 | Ex. 30 |
| --- | --- | --- | --- | --- | --- |
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| 2' fucosyllactose (2'FL) | 0.0948 | 0.09005 | 0.0853 | 0.0995 | 0.1043 |
| 6'-sialyllactose (6'SL) | 0.0948 | 0.09005 | 0.0853 | 0.0995 | 0.1043 |
| Galactooligosaccharides (GOS) | 8.630 | 8.630 | 8.630 | 8.630 | 8.630 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, $D_3$, E, $K_1$ premix | 47.40 g | 47.40 g | 47.40 g | 47.40 g | 47.40 g |
| Citric acid | 29.77 g | 29.77 g | 29.77 g | 29.77 g | 29.77 g |
| Probiotic | 1.0 | 0.95 | 0.90 | 1.05 | 1.10 |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 31-34

Examples 31-34 illustrate concentrated liquid human milk fortifiers of the present disclosure, the ingredients of which are listed in the table below. All ingredient amounts are listed as kilogram per 1000 kilogram batch of product, unless otherwise specified.

| Ingredient (Per 1000 Kg) | Ex. 31 | Ex. 32 | Ex. 33 | Ex. 34 |
| --- | --- | --- | --- | --- |
| Water | Q.S. | Q.S. | Q.S. | Q.S. |
| Casein Hydrolysate | 108 | 108 | 125 | 150 |
| Maltodextrin | 104 | 104 | 104 | 104 |
| MCT Oil | 17.3 | 17.3 | 17.3 | 17.3 |
| Tricalcium Phosphate | 16.0 | 16.0 | 16.0 | 16.0 |
| Soy Oil | 10.4 | 10.4 | 10.4 | 10.4 |
| 6' sialyllactose (6'SL) | 0.0948 | 0.09005 | 0.0853 | 0.0995 |
| Lacto-N-neotetraose | 0.0948 | 0.09005 | 0.0853 | 0.0995 |
| Galactooligosaccharides (GOS) | 6.7704 | 6.7704 | 6.7704 | 6.7704 |
| Gum Arabic | 12.0 | 10.0 | 15.0 | 2.031 |
| Starch | 12.0 | 10.0 | 35.0 | 6.0 |
| Coconut Oil | 6.3 | 6.3 | 6.3 | 6.3 |
| Potassium Citrate | 6.9 | 6.9 | 6.9 | 6.9 |
| Ascorbic Acid | 2.9 | 2.9 | 2.9 | 2.9 |
| Magnesium Chloride | 4.0 | 4.0 | 4.0 | 4.0 |
| ARA oil | 2.6 | 2.6 | 2.6 | 2.6 |
| Leucine | 1.8 | 1.8 | 1.8 | 1.8 |
| DHA oil | 2.1 | 2.1 | 2.1 | 2.1 |
| Potassium Chloride | 1.1 | 1.1 | 1.1 | 1.1 |
| Tyrosine | 1.4 | 1.4 | 1.4 | 1.4 |
| Monoglycerides | 800 g | 800 g | 800 g | 800 g |
| Mixed Carotenoid | 551 g | 551 g | 551 g | 551 g |
| M-Inositol | 529 g | 529 g | 529 g | 529 g |
| Sodium Chloride | 861 g | 861 g | 861 g | 861 g |
| L-Carnitine | 221 g | 221 g | 221 g | 221 g |
| Tryptophan | 331 g | 331 g | 331 g | 331 g |
| Zinc Sulfate | 309 g | 309 g | 309 g | 309 g |
| Niacinamide | 320 g | 320 g | 320 g | 320 g |

-continued

| Ingredient (Per 1000 Kg) | Ex. 31 | Ex. 32 | Ex. 33 | Ex. 34 |
|---|---|---|---|---|
| Tocopheryl Acetate | 364 g | 364 g | 364 g | 364 g |
| Gellan Gum | 200 g | 300 g | 400 g | 600 g |
| Ferrous Sulfate | 106 g | 106 g | 106 g | 106 g |
| Choline Chloride | 353 g | 353 g | 353 g | 353 g |
| Calcium Pantothenate | 132 g | 132 g | 132 g | 132 g |
| Vitamin A Palmitate | 77 g | 77 g | 77 g | 77 g |
| Riboflavin | 33 g | 33 g | 33 g | 33 g |
| Vitamin D3 | 13 g | 13 g | 13 g | 13 g |
| Copper Sulfate | 18 g | 18 g | 18 g | 18 g |
| Pyridoxine Hydrochloride | 20 g | 20 g | 20 g | 20 g |
| Thiamin Hydrochloride | 24 g | 24 g | 24 g | 24 g |
| Folic Acid | 3.3 g | 3.3 g | 3.3 g | 3.3 g |
| Biotin | 2.5 g | 2.5 g | 2.5 g | 2.5 g |
| Manganese Sulfate | 1.8 g | 1.8 g | 1.8 g | 1.8 g |
| Phylloquinone | 880 mg | 880 mg | 880 mg | 880 mg |
| Sodium Selenate | 90 mg | 90 mg | 90 mg | 90 mg |
| Cyanocobalamin | 88 mg | 88 mg | 88 mg | 88 mg |
| Potassium Hydroxide | Q.S. | Q.S. | Q.S. | Q.S. |

Example 35

In this Example, the effect of 2'-fucosyllactose (2'FL) or 3'-fucosyllactose (3'FL) on stimulating enteric nerve cells in the gastrointestinal tract of rodents is analyzed.

Specifically, a peristalsis model using luminally perfused mouse colon is used to test the stimulation effect of 2'FL or 3'FL on enteric nerve cells. Colon muscle is perfused with 2'FL or 3'FL, at concentrations of 1 mg/mL, 0.5 mg/mL, and 0.1 mg/mL, for 15 minutes. The frequency and amplitude of contractions of the muscle is analyzed. The results are shown in FIG. 1.

As shown in the results, there is a direct stimulation of nerve cells by 2'FL or 3'FL without involving gut microbiota and/or their metabolites. Specifically, the frequency and amplitude of contraction are reduced consistently and in a dose response fashion. The results indicate that 3'FL is more effective than 2'FL.

Example 36

In this Example, the fermentation rates of various non-digestible carbohydrates are measured.

Inclusion/exclusion criteria for choosing eight infant participants include: the infant was full term at birth with a gestational age of 38 to 42 weeks; the infant was at or above the fifth percentile for weight at birth; the infant has no maternal medical history of diabetes, tuberculosis, or perinatal infection with proven adverse effects on the fetus; was a vaginal birth; was at least 2 months of age at study entry, but not older than 4 months of age; has no known cardiac, respiratory, gastrointestinal, or other systemic disease such as urinary tract infection or otitis media; is free of history of blood group incompatibility serious enough to result in hematological problems; and is not receiving any medications (except for supplemental vitamins) and has never received antibiotics. The eight infants are allowed to consume their normal diet of breast milk or infant formula. Four infants are exclusively breast fed and four infants are exclusively formula fed one of four commercially available infant formulas.

On the day of the in vitro experiments, a fecal sample is collected in the diaper and prepped within 15 minutes of defecation. For prepping, the sample is placed in a container with tepid water and analyzed. Fecal samples are diluted 1:10 (wt/vol) in anaerobic dilution solution by blending for 15 seconds in a Waring blender under a stream of $CO_2$. Blended, diluted feces are filtered through four layers of cheesecloth and sealed in 125-mL serum bottles under $CO_2$. Inoculum is stored at 37° C. until inoculation of in vitro tubes.

Oligosaccharide substrates suitable for growing the bacterium include galactooligosaccharides (GOS) 95 (GOS; Inalco Pharmaceuticals, San Luis Obispo, Calif.), a-(2-6')-N-Acetylneuraminyl-lactose sodium salt (6'SL; Inalco Pharmaceuticals, San Luis Obispo, Calif.); 2'-a-L-Fucopyranosyl-D-Lactose (2'FL; Inalco Pharmaceuticals, San Luis Obispo, Calif.); LNnT; Orafti® HP inulin (HP inulin) (BENEO-Orafti, Belgium); and gum arabic (Fisher Scientific, Pittsburgh, Pa.). In vitro fermentation model Approximately 80 mg of each substrate is weighed in triplicate for each pull time into 16-mL Balch tubes that are used in a model that simulates large bowel fermentation. An aliquot (7.2 mL) of medium (Table 1; FIG. 2) is aseptically transferred into the Balch tubes, capped with butyl rubber stoppers, and sealed with aluminum caps. Tubes containing HP inulin and gum arabic are stored at 4° C. for approximately 12 h to enable hydration of the substrates before initiating fermentation. These tubes are placed in a 37° C. water bath approximately 30 min before inoculation. Due to the cost of the substrates and difficulty in obtaining samples from infants, tubes containing GOS, 6'SL, 2'FL, and LNnT are hydrated upon obtaining a fecal sample and placed in a 37° C. water bath until inoculation.

Sample and blank tubes are aseptically inoculated with 0.8 ml of diluted feces. Tubes are incubated at 37° C. with periodic mixing every 2 h for up to 12 h. At 0, 3, 6, and 12 h after inoculation, tubes are removed from the 37° C. incubator and processed immediately for analyses. The pH of tube contents is measured with a standard pH meter. A 3-ml subsample of fluid is collected and used for short-chain fatty acid and lactate analyses. A 2-mL sub sample is taken and frozen at −80° C. for bacterial analysis. Short-chain fatty acid (SCFA) analyses The 3-mL aliquot of fluid removed from the sample tubes for SCFA analysis is immediately added to 0.75 mL of 25% metaphosphoric acid. Concentrations of acetate, propionate, and butyrate are determined using a Hewlett-Packard 5890A series II gas chromatograph and a glass column (180 cm×4 mm i.d.) packed with 10% SP-1200/1% $H_3PO_4$ on 80/100+ mesh Chromosorb WAW (Supelco Inc., Bellefonte, Pa.). Oven temperature, detector temperature, and injector temperature are 125, 175, and 180° C., respectively. SCFA concentration values are corrected for blank tube production of SCFA and 0 h concentrations for each substrate. Total SCFA are calculated as the total amount of acetate, propionate, and butyrate.

Data is analyzed as a split-split-plot in a completely randomized block design using the Mixed procedure of SAS (SAS Inst., Inc., Cary, N.C.). Block is defined as the diet of the baby (breast milk or formula). Fixed effects tested include diet, substrate, and time, and the interactions are investigated if significant. Infant and period are included as random effects in the model. Means are separated using a protected LSD with a Tukey adjustment to control for experiment-wise error. Least square means are reported along with the pooled SEM for all response criteria. A probability of $P<0.05$ is accepted as statistically significant.

Results and Discussion

Figure 3:
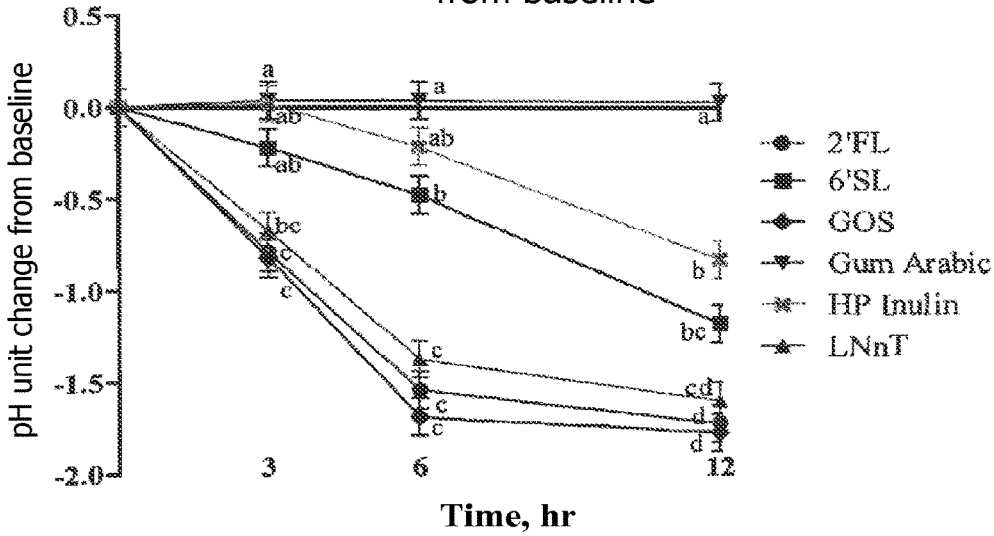
FIG. 3 is a graph depicting the change in pH over time as affected by the various oligosaccharide substrates as tested in Example 36.

The pH change from baseline decreases ($P<0.0001$) over time for all substrates except gum arabic (FIG. 3). At 3, 6, and 12 h after inoculation, pH change from baseline is smallest ($P<0.0001$) with the gum arabic substrate, and greatest in the LNnT, 2'FL, and GOS substrates. A decrease in pH is an indicator of fermentation, and these data are reflective of SCFA production.

Figure 4:
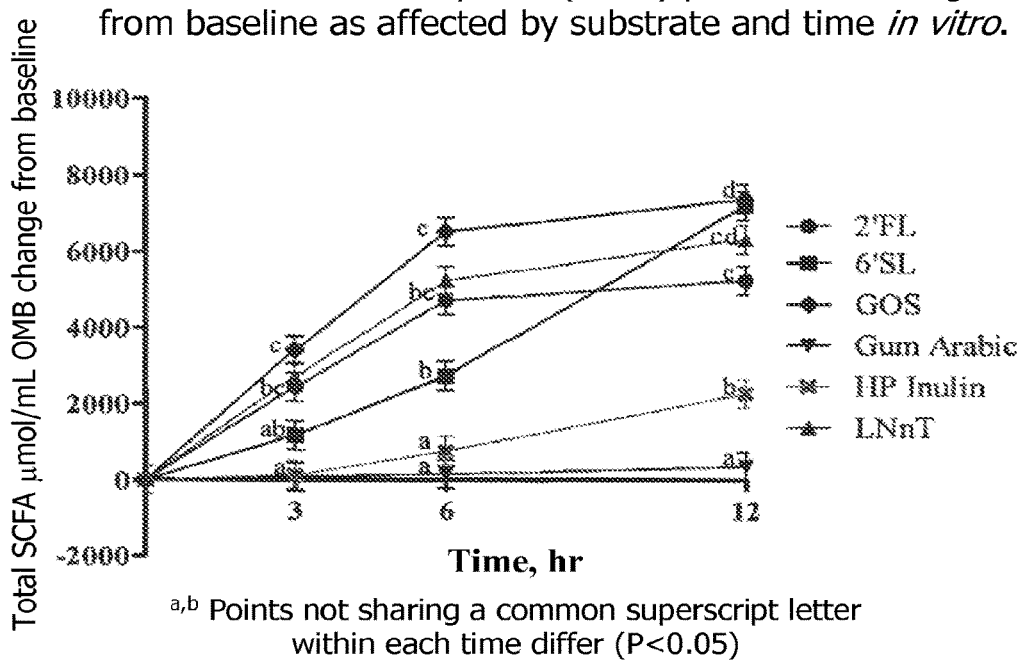
FIG. 4 is a graph depicting change in short chain fatty acid production over time as affected by the various oligosaccharide substrates as tested in Example 36.

Total SCFA production differs among substrates (FIG. 4) at 3, 6, and 12 h of fermentation ($P<0.0001$). Gum arabic produces the least amount of SCFA and does not change over time. After 3 and 6 h of fermentation, total SCFA production is lower ($P<0.05$) with HP inulin compared to all other substrates and is lower ($P<0.05$) with 6'SL compared to GOS. By 12 h of fermentation, total SCFA production remains lower ($P<0.05$) with HP inulin relative to 2'FL, 6'SL, GOS, and LNnT substrates. Also, after 12 h of fermentation, total SCFA production is greater ($P<0.05$) for the 6'SL and GOS substrates compared to 2'FL.

Example 37

In this Example, probiotic fermentation parameters are determined for purified HMOs, HMO precursors, and other prebiotic oligosaccharides.

Bacterial Cultures

All bifidobacteria strains are initially inoculated from frozen stocks, grown in deMan Rogosa Sharpe (MRS) broth (Difco, Detroit, Mich.) supplemented with 0.5 g/L L-cysteine/HCl and incubated at 37° C. for 24 h in an anaerobic chamber (90% $N_2$, 5% $CO_2$ and 5% $H_2$). Subsequently, the cultures are passed twice on a semi-synthetic MRS medium (sMRS)+0.5 g/L L-cysteine/HCl which is supplemented with 1% (w/v) filter-sterilized glucose as the sole carbohydrate source. After the 2nd pass, cultures are prepared to use as inoculums for growth assays described below. All bacterial strains for use in this Example are listed in the table below.

TABLE

| | Microorganisms | | | |
|---|---|---|---|---|
| Culture Collection Number | | Genus | Species | Strain |
| 1 | MJM29 | Bifidobacterium | adolescentis | ATCC 15703 |
| 2 | MJM30 | Bilidobacterium | infantis | S12; ATCC 15697 |
| 3 | MJM32 | Bifidobacterium | animalis subsp. lactis | DSM 10140 |
| 4 | MJM33 | Bifidobacterium | Animalis subsp. Animalis | ATCC 25527 |
| 5 | MJM34 | Bifidobacterium | Bifidum | ATCC 29521 |
| 6 | MJM35 | Bifidobacterium | Breve | ATCC 15700 |
| 7 | MJM37 | Bifidobacterium | Bifidum | ATCC 11617 |
| 8 | MJM88 | Bifidobacterium | Lactis | Bf-6 (Cargill) |
| 9 | MJM92 | Bifidobacterium | Longum | BB536 (Morinaga) |
| 10 | MJM93 | Bifidobacterium | Infantis | M-63 (Morinaga) |
| 11 | MJM94 | Bifidobacterium | Breve | M-16V (Morinaga) |
| 12 | MJM95 | Bifidobacterium | Lactis | Bb12; (Chr. Hansen) |

Bacterial Growth Assays

After the 2nd pass in sMRS+glucose+cysteine, the cultures are washed once with 10 mL of sterile sMRS+cysteine (no carbohydrate), resuspended in 10 ml of sterile sMRS+cysteine (no carbohydrate) and then used as a 1% inoculum. Carbohydrates for use in this Example are shown in the table below. The carbohydrates are sterilized with a 0.22 micron filter and used at a 1% final concentration. Cell growth is performed in 250 uL of sMRS+cysteine covered with 50 uL of mineral oil in a Bioscreen 100-well Honeycomb plate. Cell growth is monitored by measuring optical density at 600 nm (OD600) using a Bioscreen C Automated Microbiology Growth Curve Analysis System. The plate reader is operated in discontinuous mode, with absorbance readings performed in 30-minute intervals, and preceded by 30-second shaking intervals at maximum speed. Controls consist of inoculated medium lacking carbohydrate. Due to space limitations on the microtitre plate, the carbohydrates are divided into three separate groups: plate A (HMO precursors: glucose, galactose, lactose, NAG, fucose, fructose and sialic acid), plate B (Prebiotics: glucose, Purimune™ GOS, purified Purimune™ GOS, Vivinal® GOS, purified Vivinal® GOS, scFOS and PDX), and plate C (HMOs: glucose, 6'-SL, 3'-SL, 2'-FL, 3'-FL and LNnT). All three plates include a positive control (glucose) and negative control (no carbohydrate).

TABLE

| Carbohydrates | |
|---|---|
| Carbohydrate | Source |
| Dextrose (D-Glucose) | Fisher Scientific |
| D(+)-Galatose | ACROS-ORGANICS |
| a-Lactose | Fisher Scientific |
| L-(−) Fucose | SIGMA |
| D-Fructose | ALDRICH |
| Sialic acid (N-acetylneuraminic acid) | CALBIOCHEM |
| NAG (N-acetyl-D-glucosamine) | SIGMA |
| GOS (Purimune ™ Galactooligiosaccharide) | GTC Nutrition |
| Purified GOS (Purimune ™ Galactooligosaccharide) | GTC Nutrition |
| Vivinal ® GOS (Galactooligosaccharide) | Friesland Foods |
| Purified Vivinal ® GOS (Galactooligosaccharide) | Friesland Foods |
| scFOS (Short-Chain Fructooligosaccharide) | Nutraflora ® P-95 (GTC Nutrition) |

TABLE-continued

Carbohydrates

| Carbohydrate | Source |
| --- | --- |
| PDX (Litesse ® Polydextrose) | DANISCO |
| 6'SL (6'-sialyllactose) | V-labs; SL 306 Lot#HGDX 21-163-1 |
| 3'SL (3'-sialyllactose) | V-labs; SL 302 Lot#HGDX 76-161-1 |
| 2'FL (2'-fucosyllactose) | V-labs; Lot#DX103 |
| 3'FL (3'-fucosyllactose) | V-labs; Lot#DX807 |
| LNnT (Lacto-N-Neotetraose) | Abbott Nutrition |

Bacterial Growth Curves

The OD600 data for each carbohydrate is corrected by subtracting the OD600 of the basal media (sMRS)+cysteine from the sample plate for each probiotic. Maximum OD is determined by inspection of the corrected growth data. OD is determined by subtracting the initial corrected OD (time point 0) from the maximum corrected OD. Samples are grown in biologically independent triplicates and the resulting growth kinetic data are expressed as the mean of these replicates.

For the growth curve plots, OD600 vs. time is first plotted for the bacteria grown on medium lacking carbohydrate (sMRS). For all other carbohydrates, the OD600 data is corrected by subtracting the OD600 of sMRS.

Purification of GOS

Purified GOS is obtained by purification of Purimune™ GOS (GTC Nutrition) and Vivinal® GOS (Friesland Foods Domo). Stock solutions of 1.5 g/100 mL are applied to a XK column (XK 50/100 column, 5.0×100 cm, GE healthcare) packed with Sephadex G25 medium (Sigma). The column is eluted with pure distilled water at a rate of 8 ml/min and is collected in 12-mL fractions by a Gilson FC 203B fraction collector.

Detection of carbohydrate in every 2-3 fractions is performed using the phenol—sulfuric acid assay. Briefly, 50 μL of sample (2 μL of fraction and 48 μL of distilled water in a well) is added to 150 nl of concentrated sulfuric acid rapidly in a 96-well microtitre plate Immediately thereafter, 30 nl of 5% phenol is added and the plate is kept in a static water bath for 30 minutes at 80° C. After cooling to room temperature for 5 minutes, it is wiped dry and absorbance at 490 nm is measured by a SpectraMax Plus384 Spectrophotometer. Based on carbohydrate analysis, fractions containing minimal di- and monosaccharides are pooled and freeze dried (Freeze dry system/Freezezone 4.5/LABCONCO) for bacterial fermentation experiments. In addition, freeze dried GOS is pooled from multiple runs in order to generate enough purified GOS for growth experiments (5 runs with Purimune™ GOS and 3 runs with Vivinal® GOS).

Results & Discussion

GOS Purification

GOS is produced by the transgalactosylation of lactose and has been used as a prebiotic supplement in pediatric nutrition. Due to issues with GOS synthesis, commercial GOS products are a mixture of many different carbohydrates which may include mono- and disaccharides. In order to test the fermentation parameters of GOS and not the mono- and disaccharides which would not normally reach the colon, a purified GOS fraction, essentially free of mono- and disaccharides is obtained. Glucose (monosaccharide), lactose (disaccharide) and raffinose (trisaccharide) are used as standards. Consistent with information from the suppliers, Purimune™ GOS has less mono- and disaccharides than Vivinal® GOS. For example, the Purimune™ GOS peaks before the raffinose peak suggesting that Purimune™ GOS consists primarily of trisaccharides or larger. For Vivinal® GOS, the peak is observed at a similar fraction number as lactose. Since lactose begins to appear in fraction 55, fractions 30 through 55 are used as the purified GOS from both suppliers.

HMO Precursor Fermentation

Figure 5A:
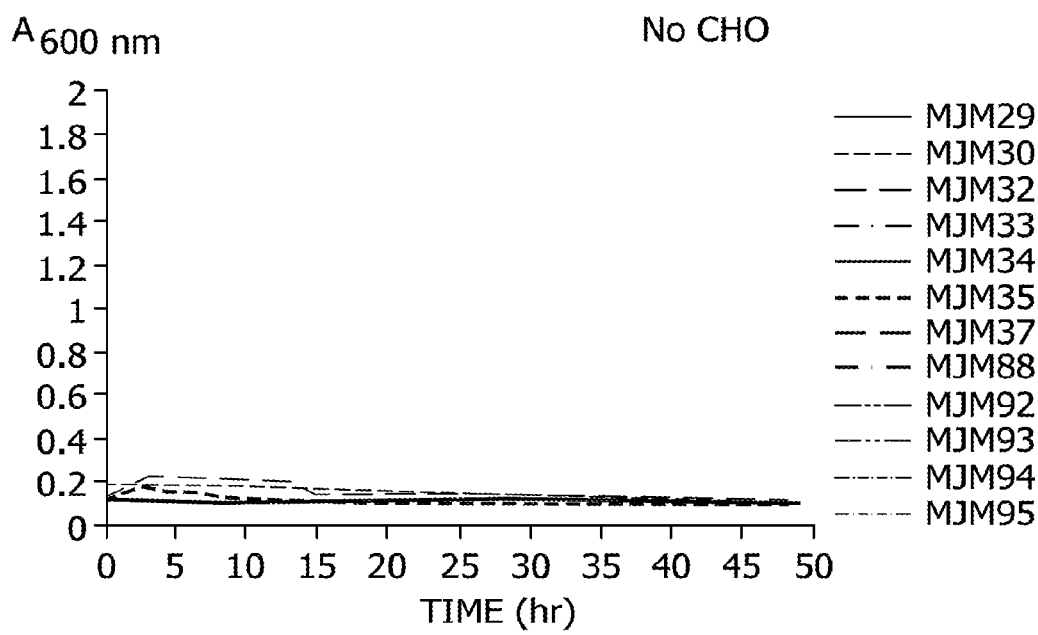
FIG. 5A depicts growth curves of various *Bifidobacterium* spp. as evaluated in Example 37.
Figure 5B:
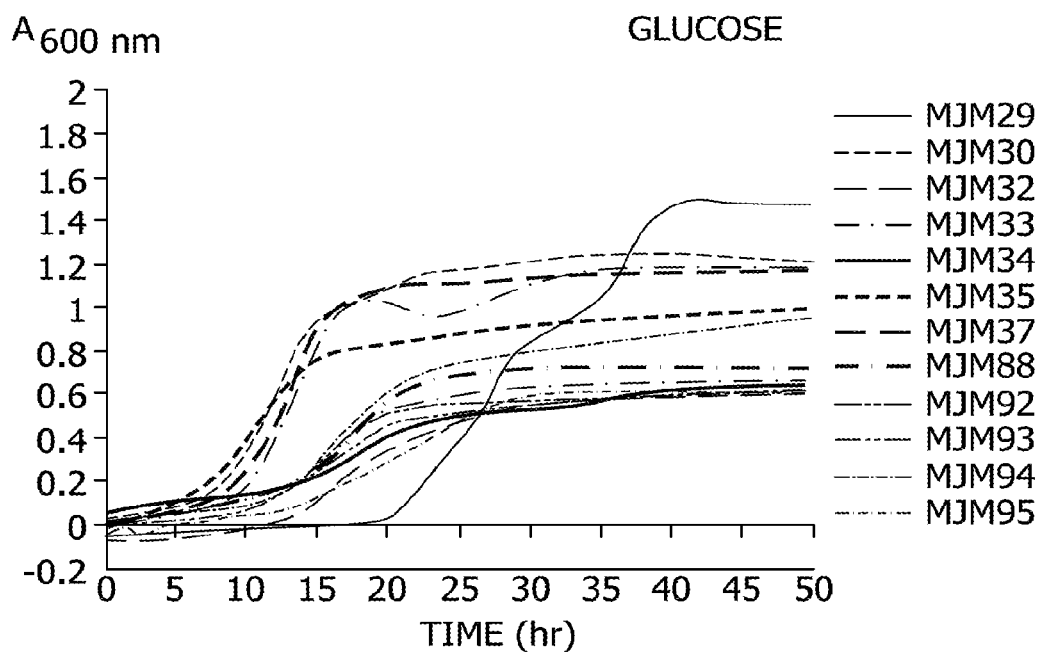
FIG. 5B depicts growth curves of various *Bifidobacterium* spp. as evaluated in Example 37.
Figure 5C:
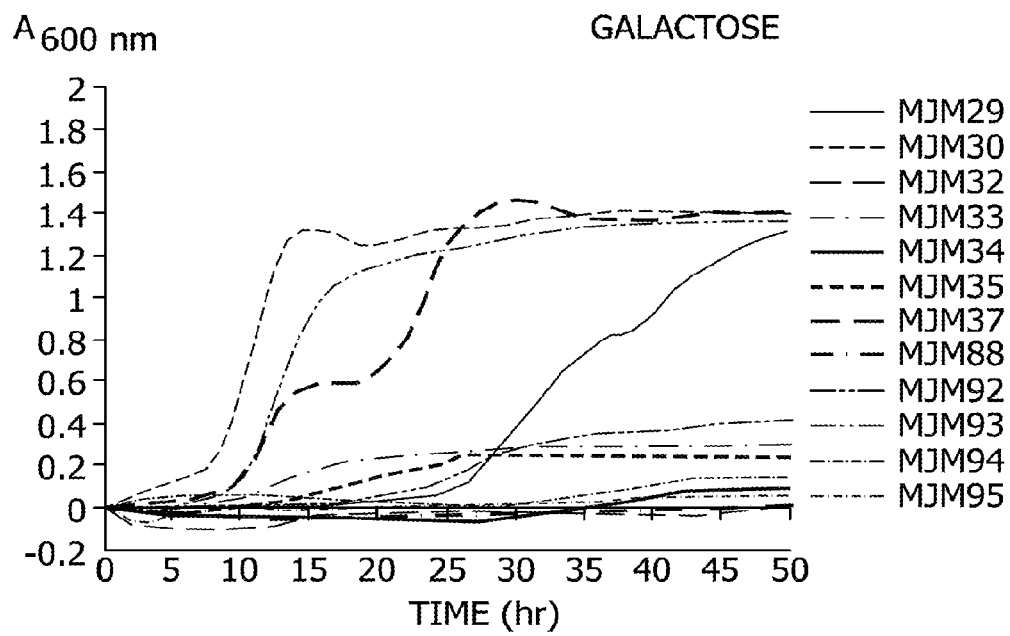
FIG. 5C depicts growth curves of various *Bifidobacterium* spp. as evaluated in Example 37.
Figure 5D:
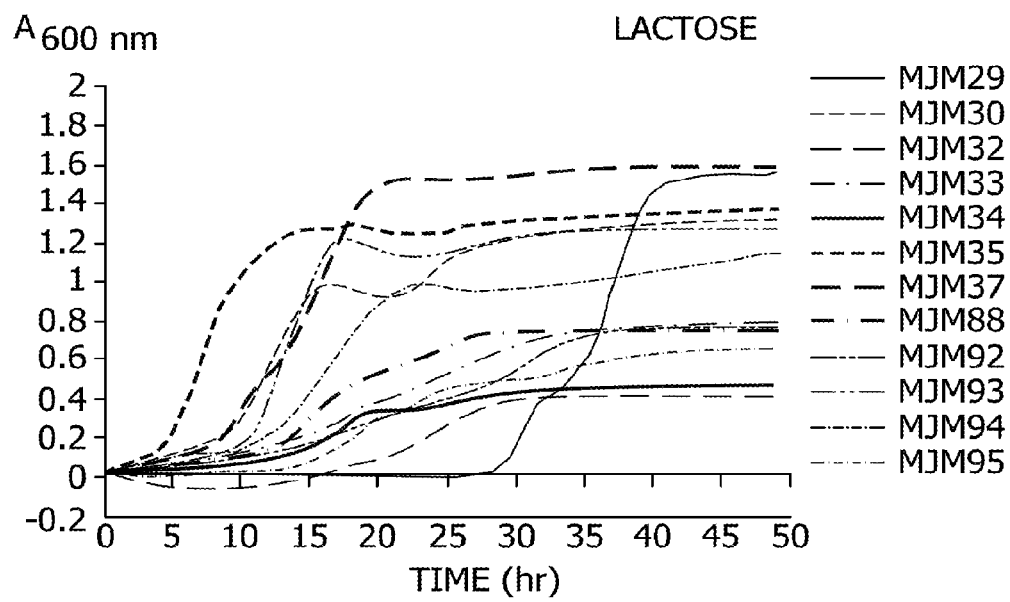
FIG. 5D depicts growth curves of various *Bifidobacterium* spp. as evaluated in Example 37.
Figure 5E:
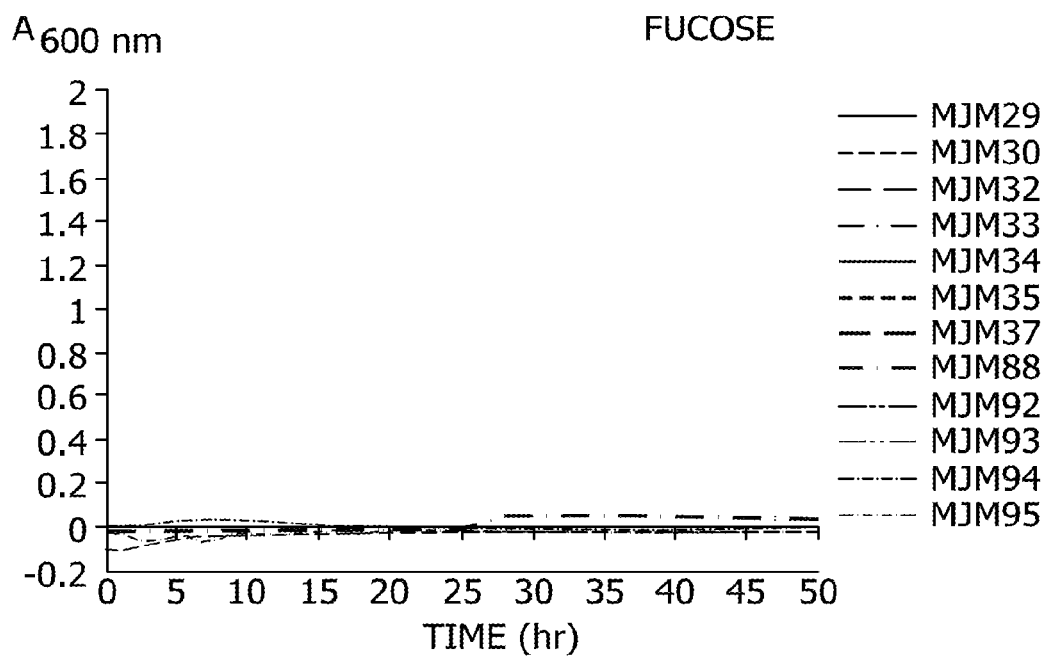
FIG. 5E depicts growth curves of various *Bifidobacterium* spp. as evaluated in Example 37.
Figure 5F:
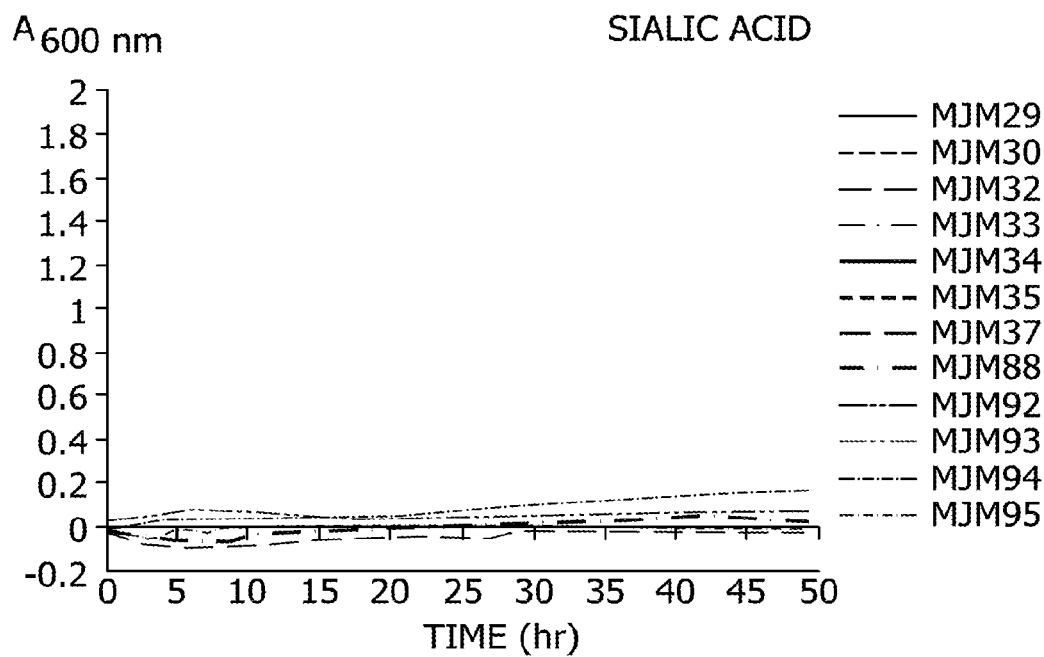
FIG. 5F depicts growth curves of various *Bifidobacterium* spp. as evaluated in Example 37.
Figure 5G:
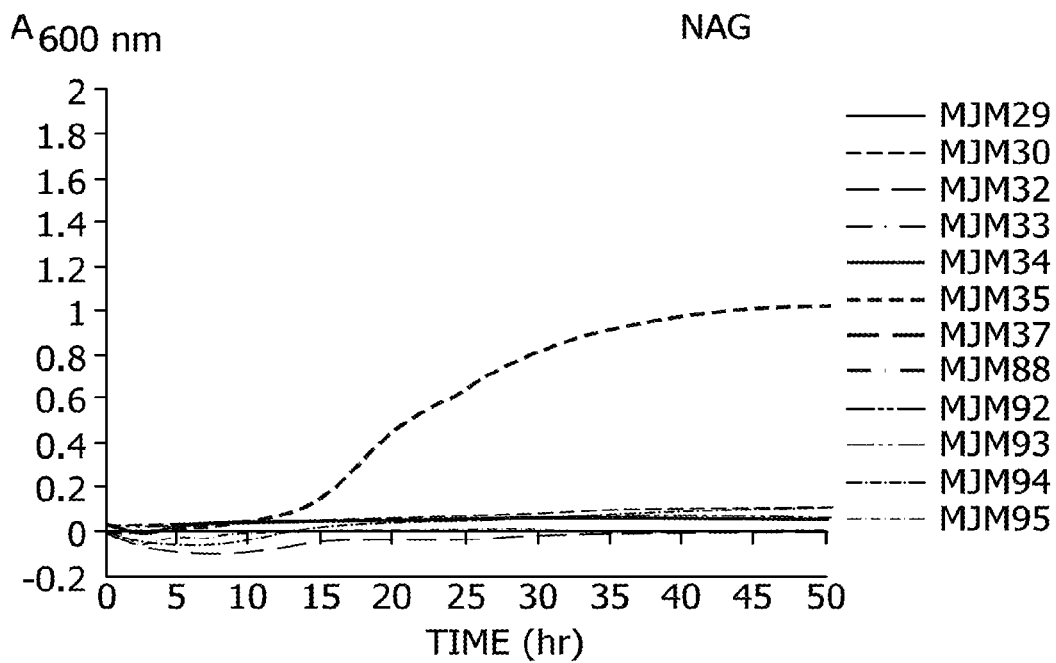
FIG. 5G depicts growth curves of various *Bifidobacterium* spp. as evaluated in Example 37.
Figure 5H:
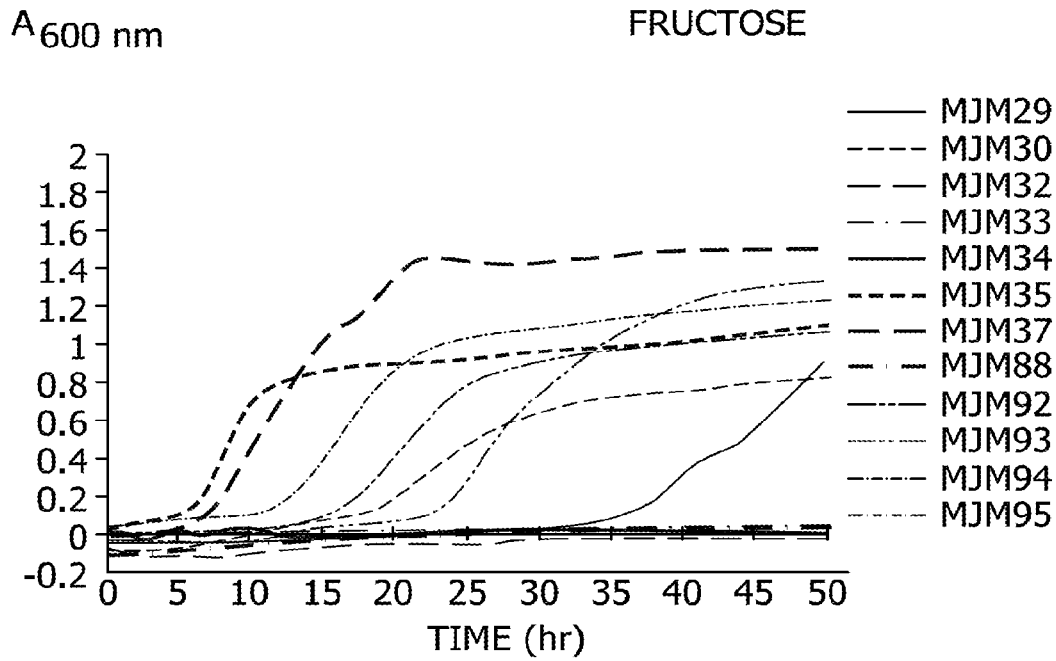
FIG. 5H depicts growth curves of various *Bifidobacterium* spp. as evaluated in Example 37.

All bifidobacteria tested grow very little in the basal media (sMRS+cysteine) (FIG. 5A), whereas they all grow well in glucose (FIG. 5B). In general, the bifidobacteria, which is not able to ferment galactose (FIG. 5C), also has reduced growth on lactose (FIG. 5D). None of the bifidobacteria are able to ferment L-fucose (FIG. 5E) or sialic acid (FIG. 5F), two key constituents of HMOs and mucin. Only B. breve ATCC 15700 is able to ferment NAG (FIG. 5G), a key component of HMOs and mucin. Lastly, the majority of bifidobacteria is able to ferment fructose (FIG. 5H).

Prebiotic Fermentation

Figure 6A:
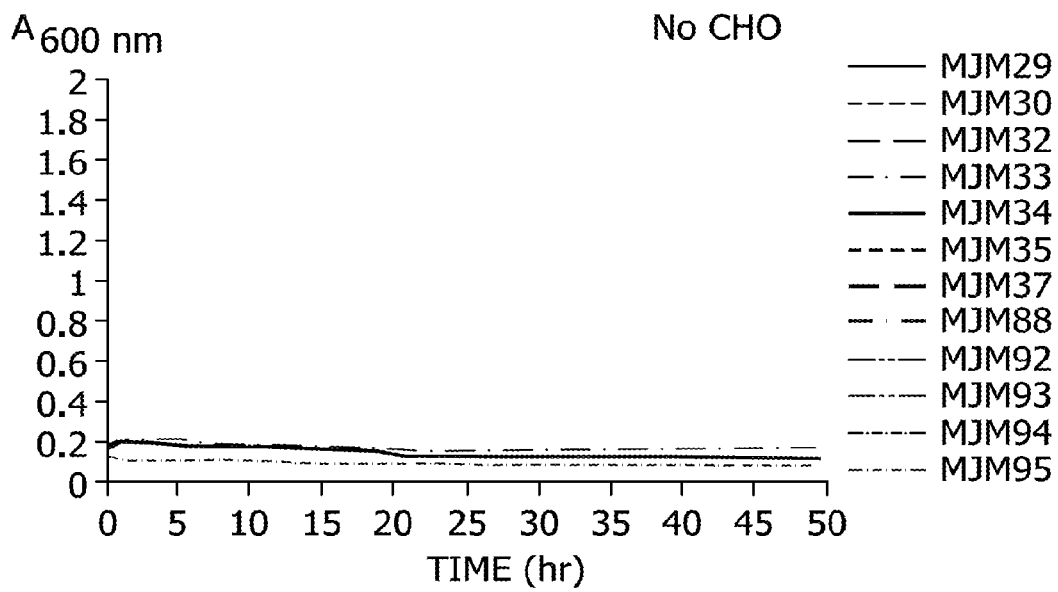
FIG. 6A depicts growth curves of various *Bifidobacterium* spp. as evaluated in Example 37.
Figure 6B:
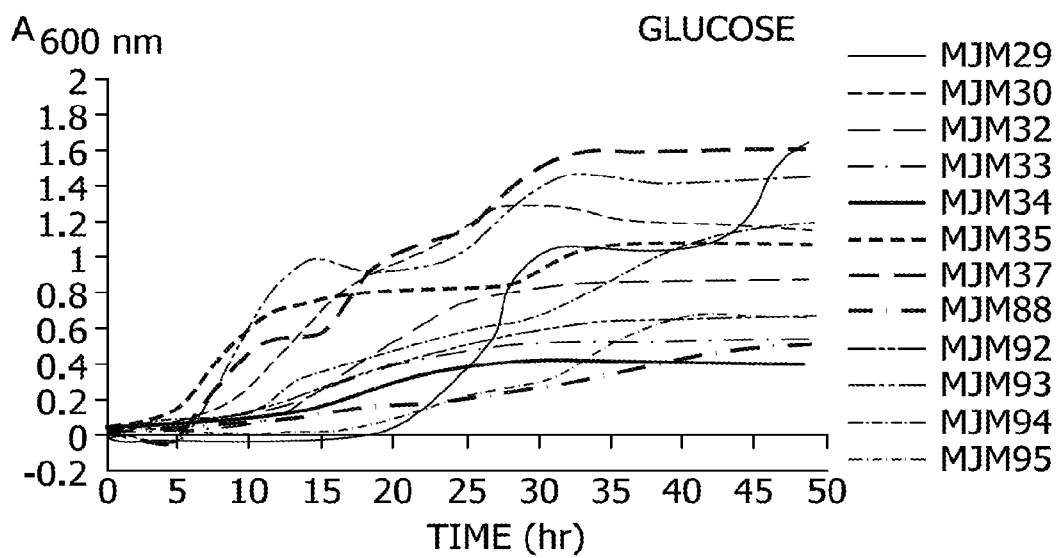
FIG. 6B depicts growth curves of various *Bifidobacterium* spp. as evaluated in Example 37.
Figure 6C:
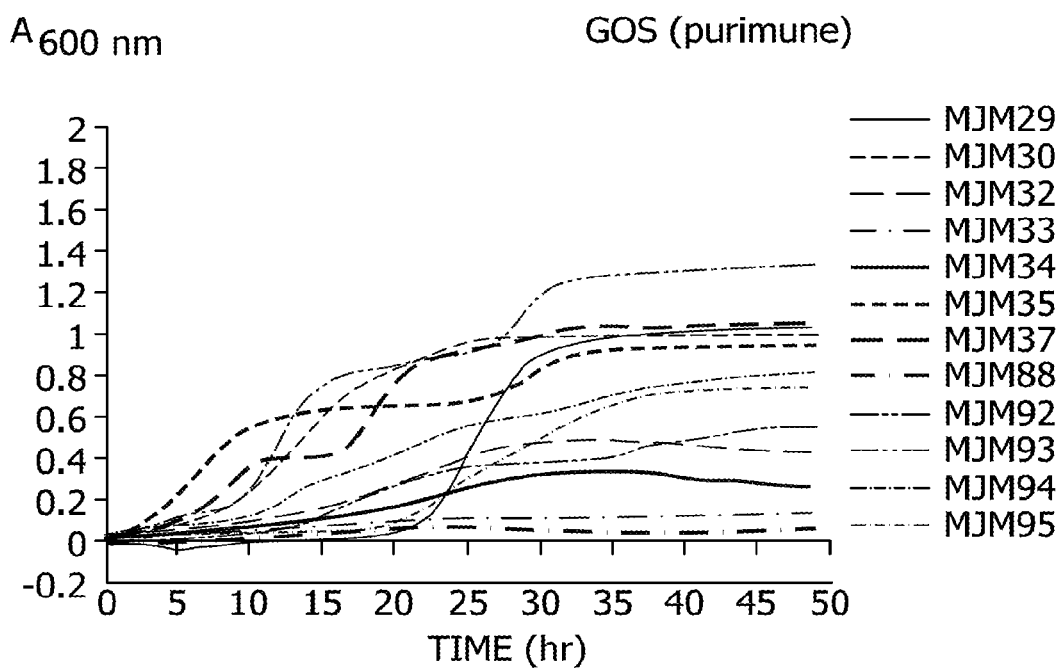
FIG. 6C depicts growth curves of various *Bifidobacterium* spp. as evaluated in Example 37.
Figure 6D:
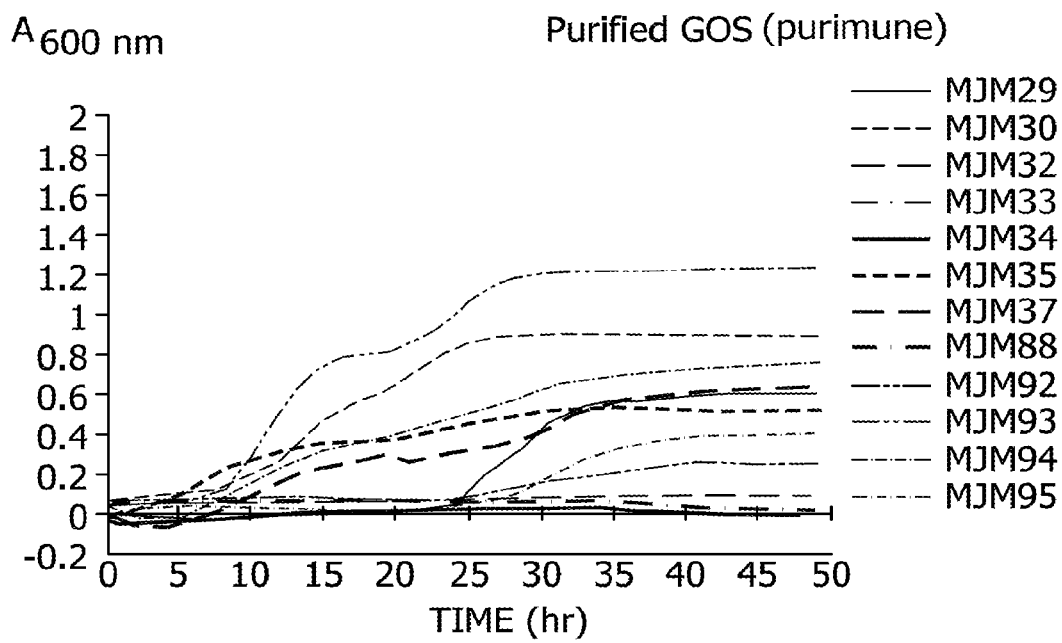
FIG. 6D depicts growth curves of various *Bifidobacterium* spp. as evaluated in Example 37.
Figure 6E:
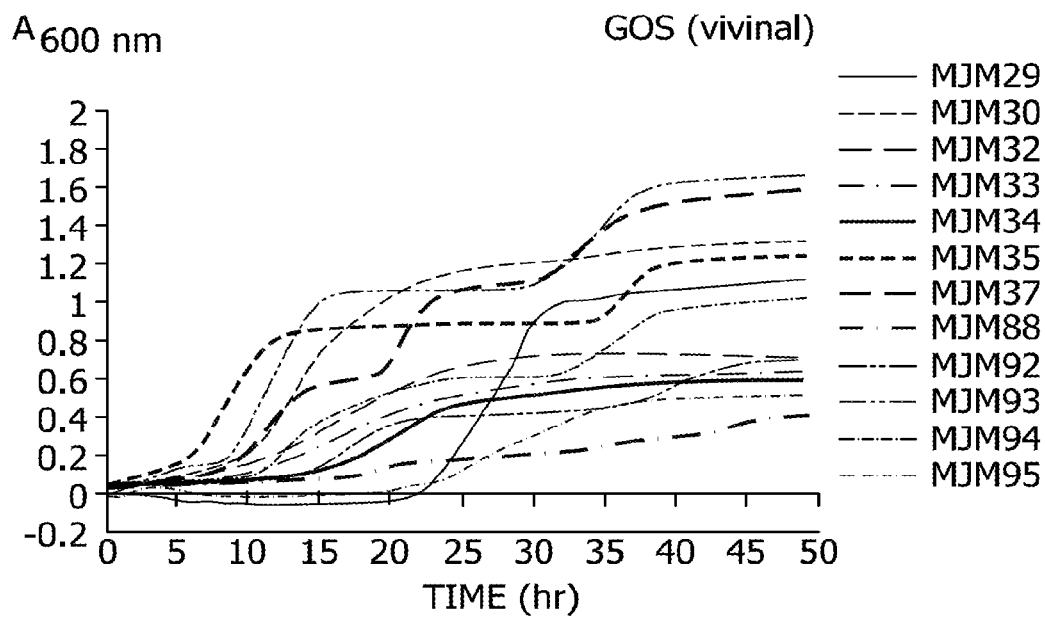
FIG. 6E depicts growth curves of various *Bifidobacterium* spp. as evaluated in Example 37.
Figure 6F:
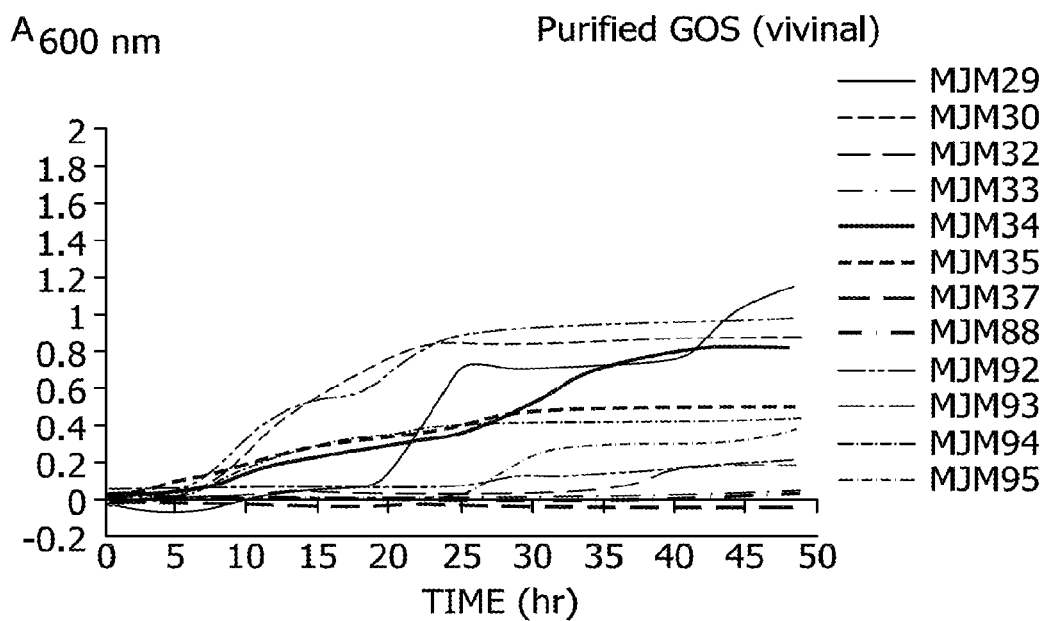
FIG. 6F depicts growth curves of various *Bifidobacterium* spp. as evaluated in Example 37.
Figure 6G:
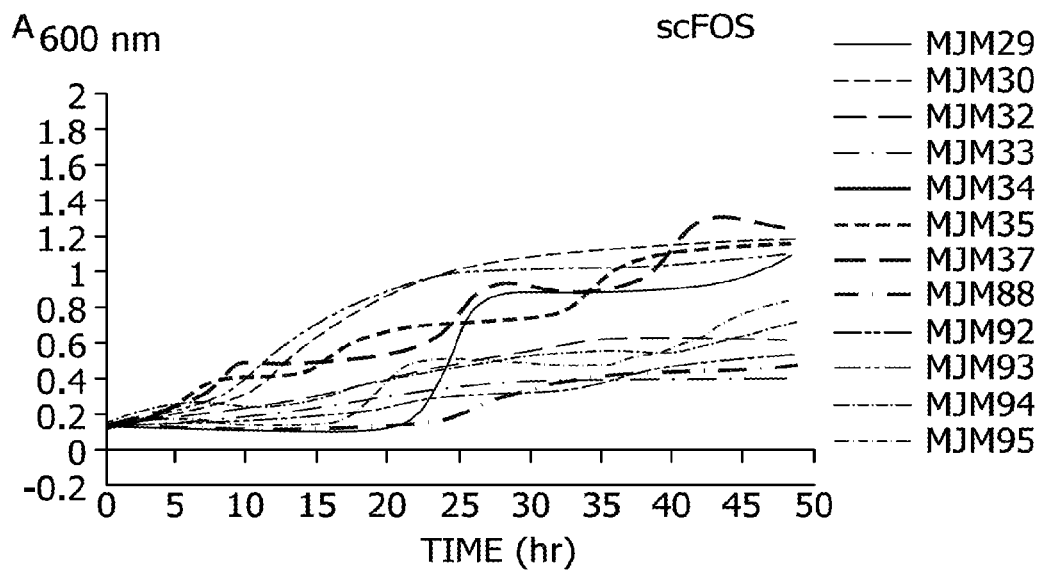
FIG. 6G depicts growth curves of various *Bifidobacterium* spp. as evaluated in Example 37.
Figure 6H:
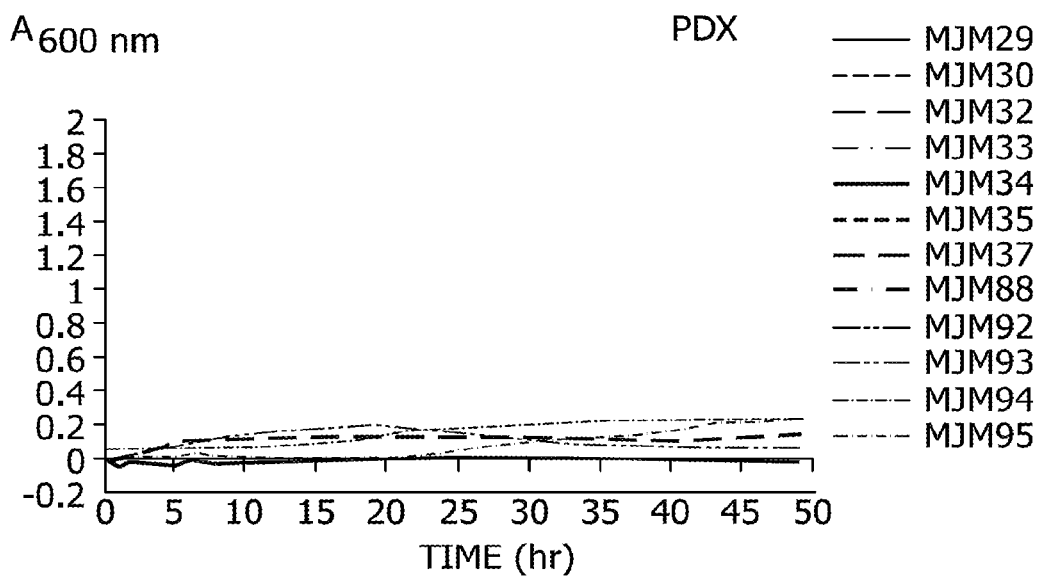
FIG. 6H depicts growth curves of various *Bifidobacterium* spp. as evaluated in Example 37.

Removal of mono- and disaccharides from Purimune™ GOS results in a decrease in growth for all bifidobacteria (FIG. 6A). In fact, B. lactis DSM 10140, B. animalis ATCC 25527, B. bifidum ATCC 29521, B. lactis Bf-6 and B. longum are not able to ferment the purified Purimune™ GOS (FIG. 6D). A similar pattern is seen with purified Vivinal® GOS (FIG. 6F), except more growth is seen with Vivinal® GOS than Purimune™ GOS. In order to mimic the colonic situation, the free mono- and disaccharides present in these products need to be removed. Also, it is clear that Purimune™ GOS has a higher relative concentration of oligosaccharides. Both B. infantis strains are among the best growers on purified GOS as determined by 40D, confirming that GOS is a reasonable prebiotic to add to infant formula if the goal is to increase B. infantis. All bifidobacteria tested, except for B. animalis ATCC 25527, are able to ferment scFOS (FIG. 6G), whereas no bifidobacteria are able to ferment polydextrose (PDX) (FIG. 6H).

HMO Fermentation

Figure 7A:
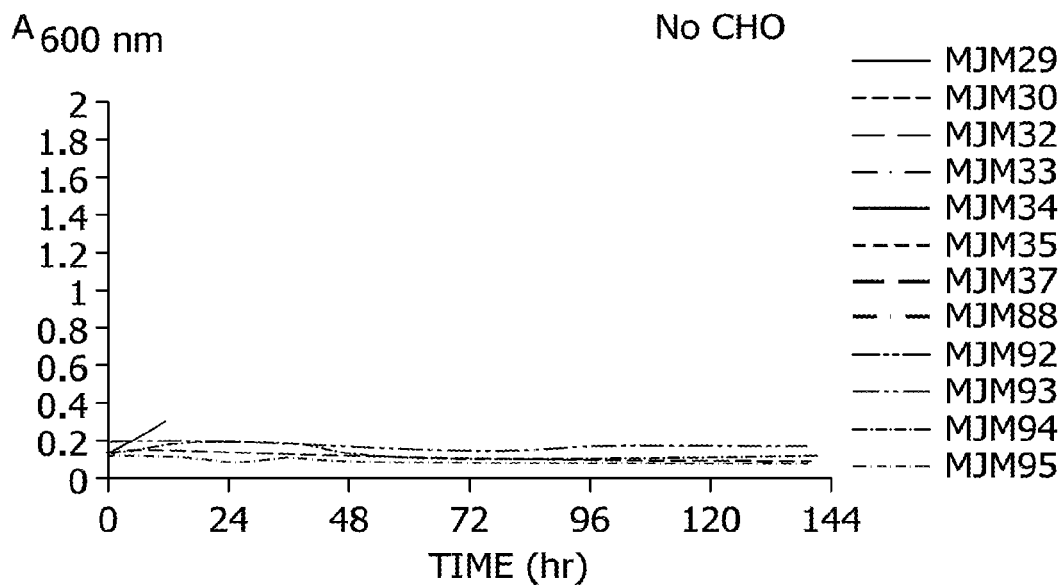
FIG. 7A depicts growth curves of various *Bifidobacterium* spp. as evaluated in Example 37.
Figure 7B:
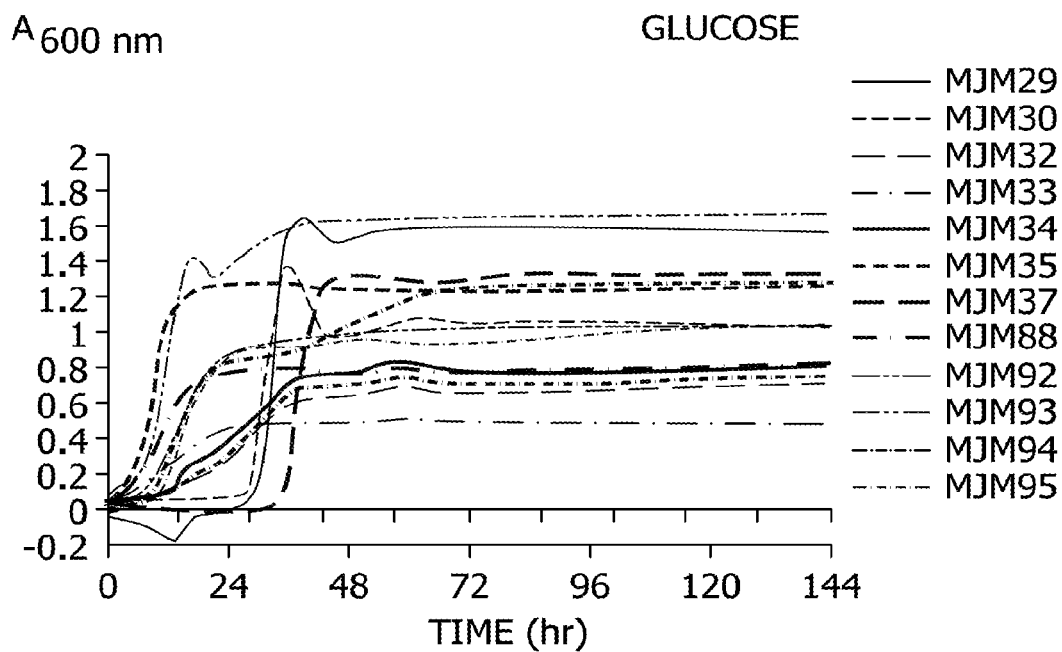
FIG. 7B depicts growth curves of various *Bifidobacterium* spp. as evaluated in Example 37.
Figure 7C:
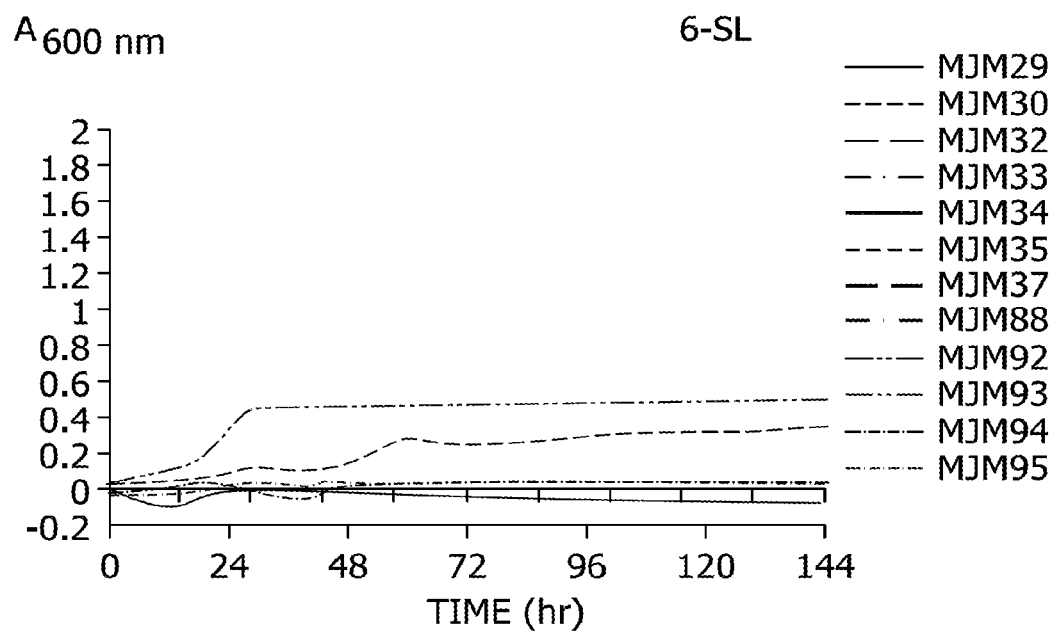
FIG. 7C depicts growth curves of various *Bifidobacterium* spp. as evaluated in Example 37.
Figure 7D:
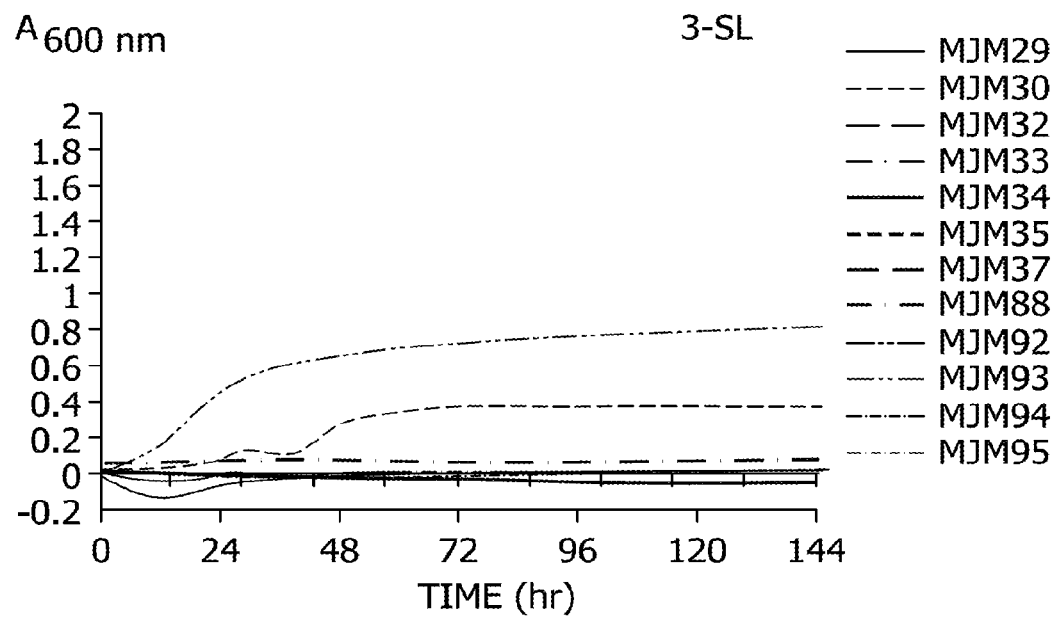
FIG. 7D depicts growth curves of various *Bifidobacterium* spp. as evaluated in Example 37.
Figure 7E:
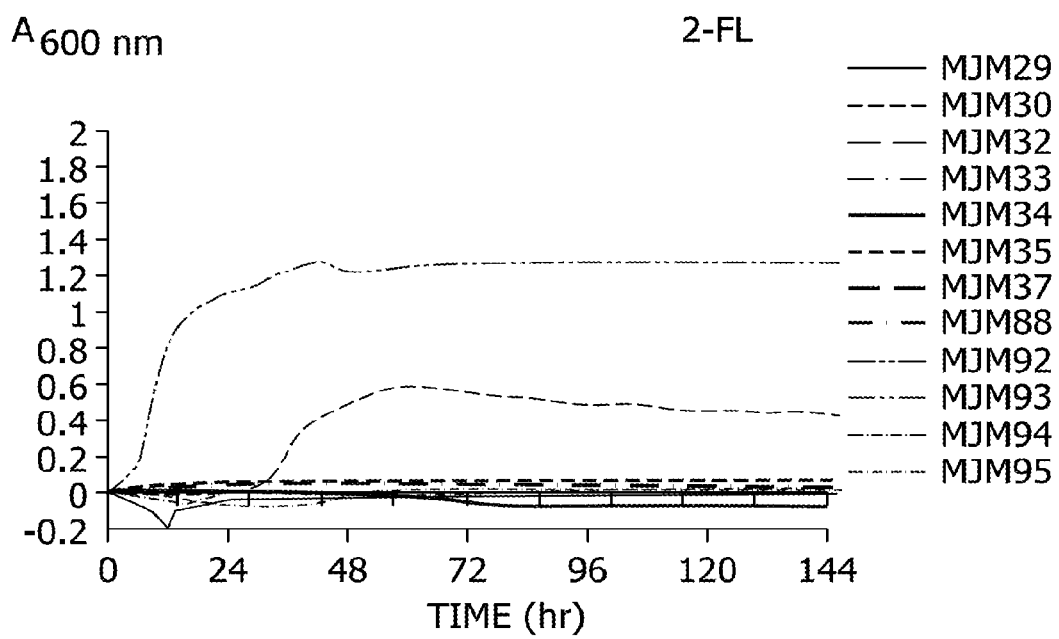
FIG. 7E depicts growth curves of various *Bifidobacterium* spp. as evaluated in Example 37.
Figure 7F:
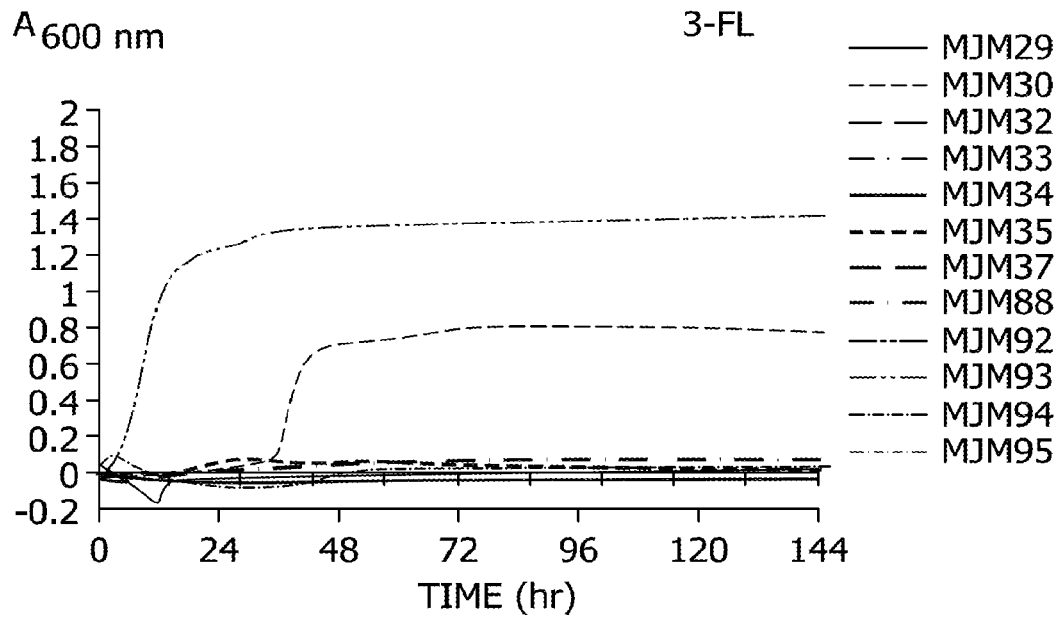
FIG. 7F depicts growth curves of various *Bifidobacterium* spp. as evaluated in Example 37.
Figure 7G:
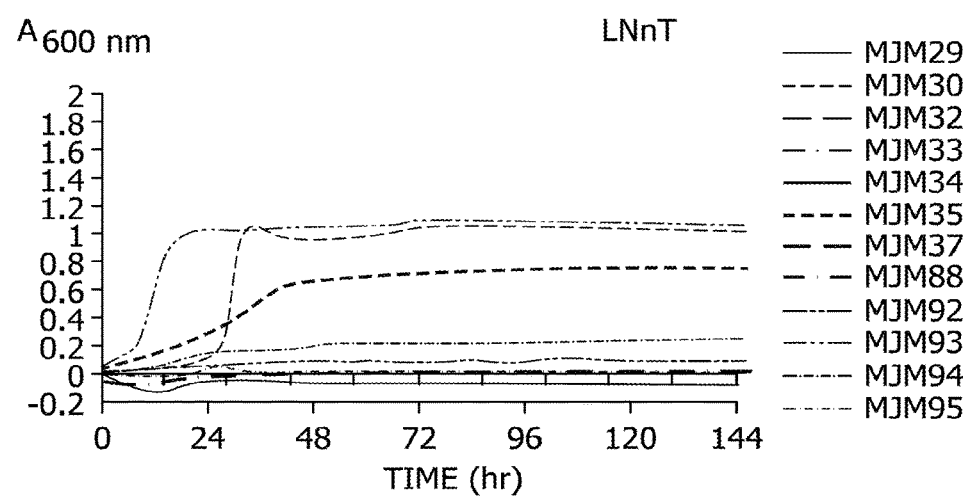
FIG. 7G depicts growth curves of various *Bifidobacterium* spp. as evaluated in Example 37.

Only B. infantis ATCC 15697 and B. infantis M-63 are able to ferment 6'-SL, 3'-SL, 2'-FL and 3'-FL (FIG. 7C-7F). In all cases, B. infantis M-63 grows better than B. infantis ATCC 15697. On the more complex LNnT (FIG. 7G), B. breve ATCC 15700 and the two B. infantis strains grow well but not B. breve M16-V. In addition, the ability of the two B. infantis strains to ferment HMOs correlates with the abundance of B. infantis found in breast fed infants. Curiously, both B. infantis strains are not able to ferment fucose or sialic acid.

Conclusions

There are significant differences amongst the tested bifidobacteria strains regarding their abilities to ferment HMO precursors, prebiotics and HMOs. Of the 12 bifidobacteria strains tested, none are able to ferment sialic acid. Regarding prebiotics, most of the bifidobacteria are able to ferment GOS and scFOS, but they are not able to ferment PDX. Amongst the bifidobacteria strains tested, only B. infantis ATCC 15697 and B. infantis M-63 are able to ferment 6'-SL, 3'-SL, 2'-FL and 3'-FL. *B. breve* ATCC 15700, *B. infantis* ATCC 15697 and *B. infantis* M-63 are able to ferment LNnT.

Example 38

In this Example, the ability of Lacto-N-neotetraose (LNnT), 2'-Fucosyllactose (2'FL), and 6'-Sialyllactose (6'SL) to protect against feeding intolerance and necrotizing enterocolitis (NEC) by inducing epithelial cell differentiation and barrier function (cell resistance), promoting digestive function, promoting antibacterial function are evaluated using cell culture models of the human small intestine. The ability of LNnT, 2'FL, and 6'SL to exert these protective and beneficial effects is evaluated using in vitro cultures representing various phases of the differentiated intestinal epithelium. Epithelial cells are cultured in the presence of various concentrations of LNnT, 2'FL, 6'SL or a control oligosaccharide of each of these human milk oligosaccharides (HMOs) and the impact of the LNnT, 2'FL, 6'SL or controls on cell differentiation, barrier function, digestive function, and protection from bacteria is measured.

Figure 8:
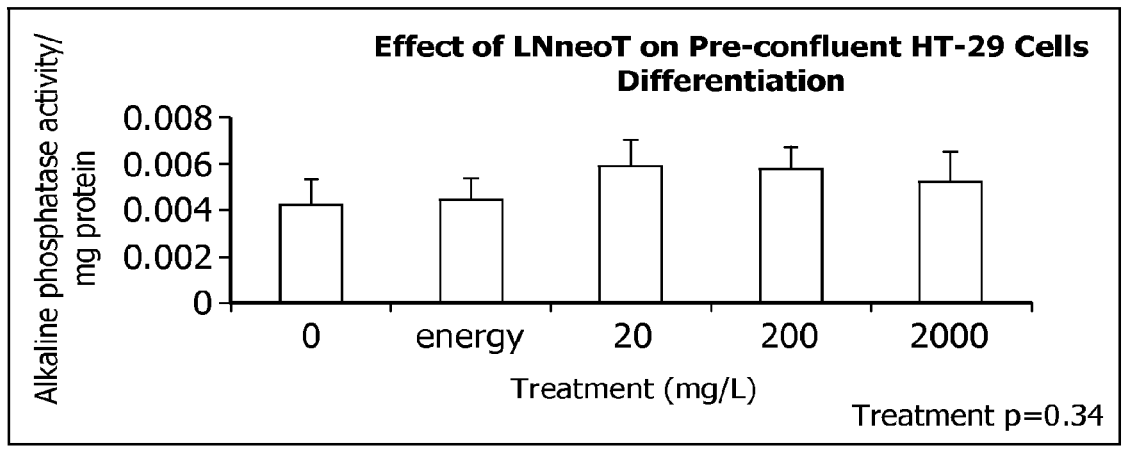
FIG. 8 is a graph showing Pre-confluent HT-29 epithelial cell differentiation in the presence of LNnT, 2'FL, and 6'SL.
Figure 9:
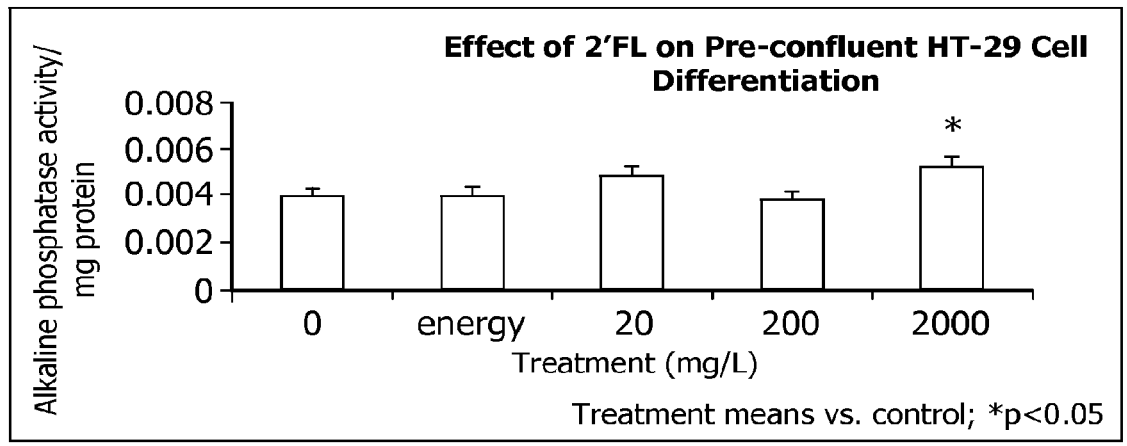
FIG. 9 is a graph showing Pre-confluent HT-29 epithelial cell differentiation in the presence of LNnT, 2'FL, and 6'SL.
Figure 10:
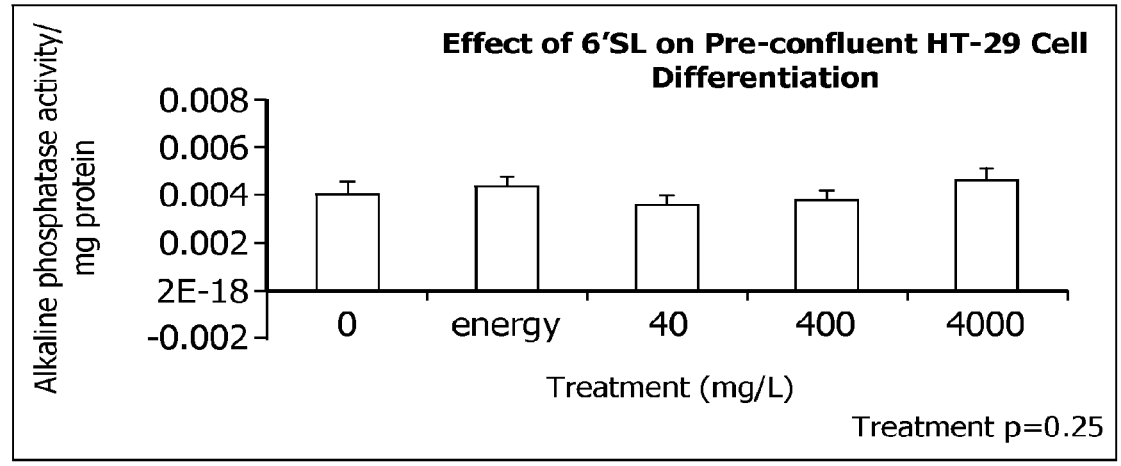
FIG. 10 is a graph showing Pre-confluent HT-29 epithelial cell differentiation in the presence of LNnT, 2'FL, and 6'SL.

In a first experiment, HT-29 cells, which model the immature epithelial cells of the small intestine, were incubated in a humidified atmosphere of 5% carbon dioxide at 37° C. in the presence of LNnT or 2'FL at concentrations of 0 mg/L ("0"), 20 mg/L ("20"), 200 mg/L ("200"), and 2000 mg/L ("2000") or in the presence of 6'SL at concentrations of 0 mg/mL ("0"), 40 mg/mL ("40"), 400 mg/mL ("400"), and 4000 mg/mL ("4000") for 72 hours. The culture medium utilized is Dulbecco's Modified Eagle Medium (Life Technologies, Foster City Calif.) supplemented with 10% fetal calf serum and 2 mM glutamine The controls ("energy") consisted of 91.5 mg lactose and 64.2 mg N-acetyllactosamine/L for LNnT; 133 mg lactose and 67 mg fucose/L for 2'FL; and 195 mg lactose and 205 mg/L sialic acid for 6'SL. The impact of the LNnT, 2'FL, and 6'SL at various levels and the controls on the alkaline phosphatase activity per milligram of protein for HT-29 cells is measured. Alkaline phosphatase activity is important for nutrient digestion, important for breakdown of the harmful bacteria lipopolysaccharide molecules that induce inflammation, and is a marker of cell differentiation. The results of the measurements are shown in FIGS. 8-10, which indicate that there is a significant increase in alkaline phosphatase activity (and thus an increase in cell differentiation, digestive function, and protection against harmful effects of bacteria) at the high dose of 2'FL, a trend toward an increase in cells treated with LNnT, and no apparent effect on cells treated with 6'SL.

Figure 11:
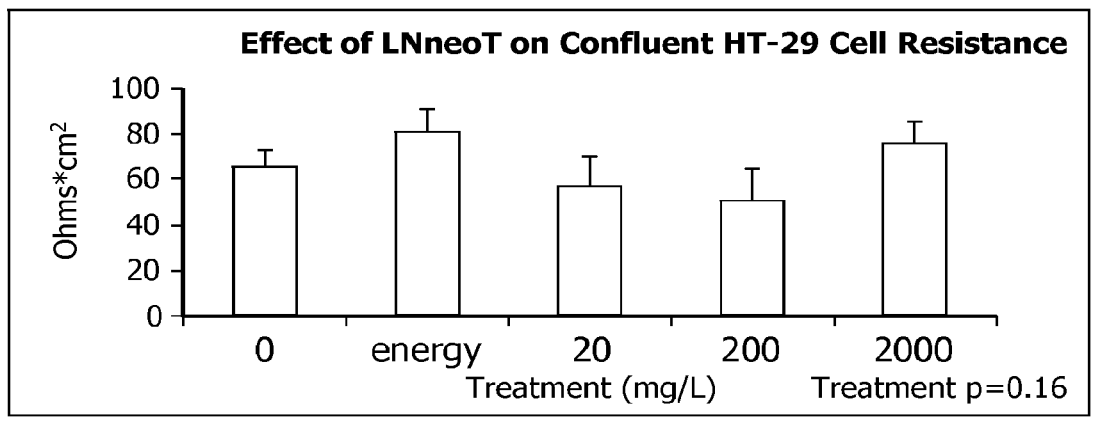
FIG. 11 is a graph showing Confluent HT-29 epithelial cell resistance in the presence of LNnT, 2'FL, and 6'SL.
Figure 12:
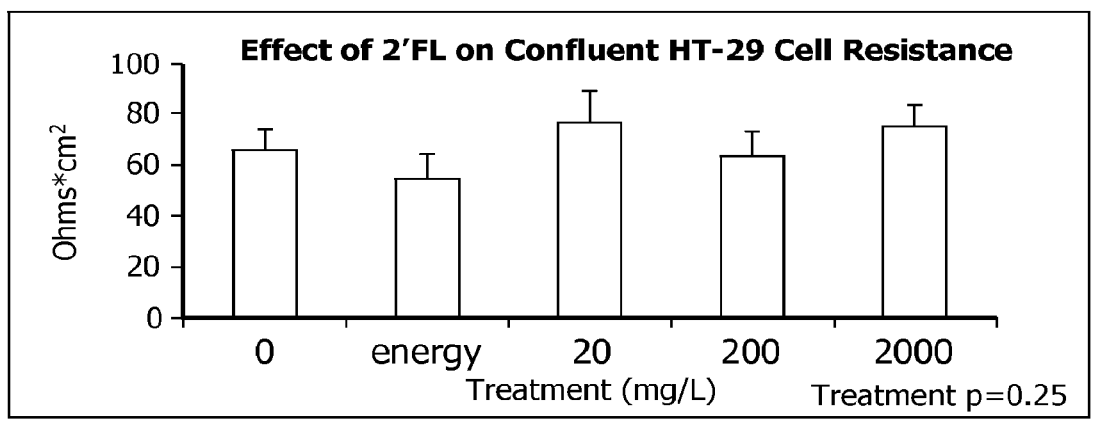
FIG. 12 is a graph showing Confluent HT-29 epithelial cell resistance in the presence of LNnT, 2'FL, and 6'SL.
Figure 13:
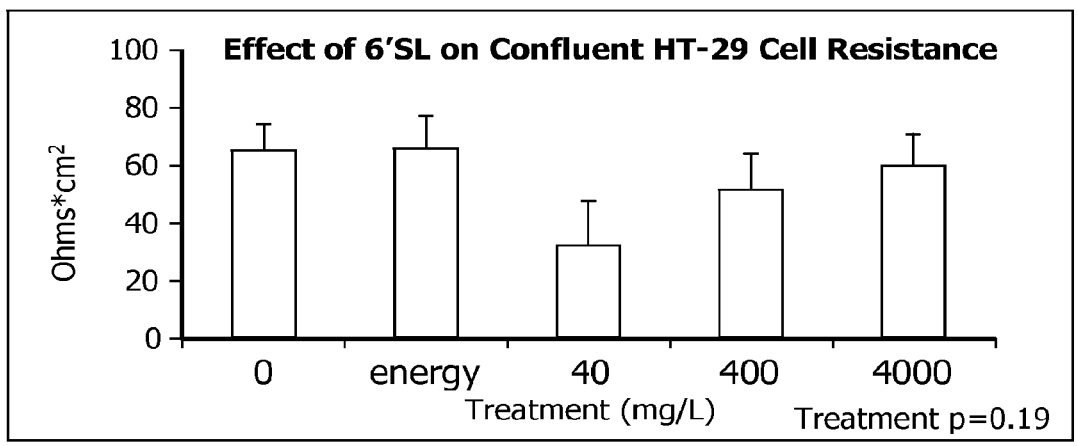
FIG. 13 is a graph showing Confluent HT-29 epithelial cell resistance in the presence of LNnT, 2'FL, and 6'SL.

FIGS. 11-13 illustrate the effect of LNnT, 2'FL, and 6'SL on cell resistance (transepithelial resistance), which is a marker for epithelial barrier function, wherein a higher resistance is associated with a higher barrier function. Epithelial cell resistance or barrier function is a measure of differentiated epithelial cell function. Specifically, as the cells mature, tighter junctions between the cells are formed resulting in a stronger epithelial cell barrier. This barrier prevents the movement of large molecules, bacteria, or viruses from one side of the barrier to the other, which could improve resistance to infection, sepsis, and NEC. Transepithelial resistance is measured using Transwell Snapwell inserts containing the desired cell culture and are transferred to modified Ussing chambers and bathed in modified Kreb's solution at 37° C. with 95% oxygen and 5% carbon dioxide. Transepithelial resistance is measured as the passive transport of ions across the monolayers.

Figure 14:
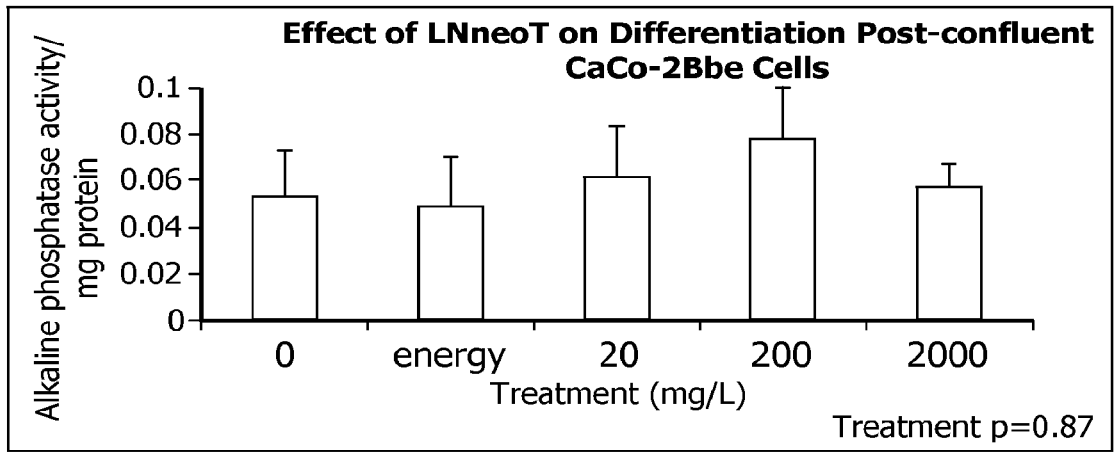
FIG. 14 is a graph showing Post-confluent CaCo-2Bbe epithelial cell differentiation in the presence of LNnT, 2'FL, and 6'SL.
Figure 15:
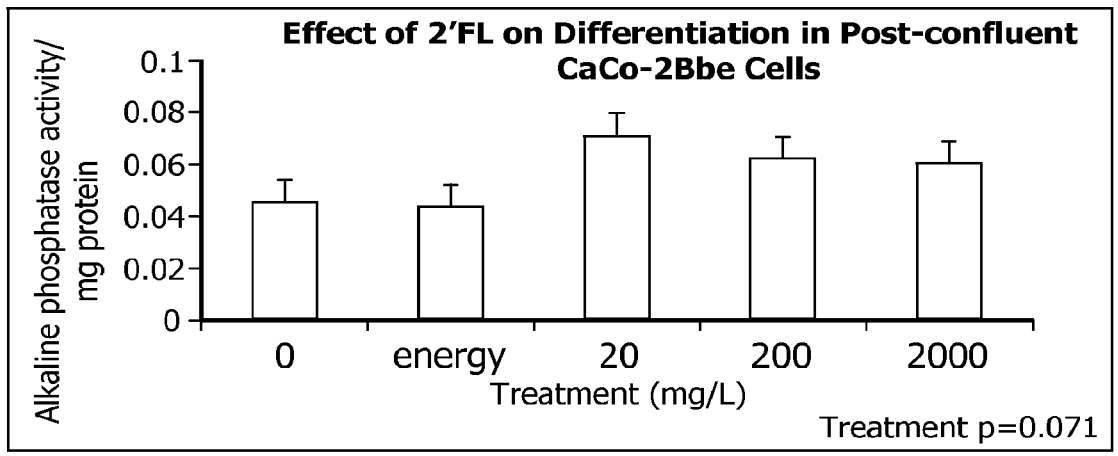
FIG. 15 is a graph showing Post-confluent CaCo-2Bbe epithelial cell differentiation in the presence of LNnT, 2'FL, and 6'SL.
Figure 16:
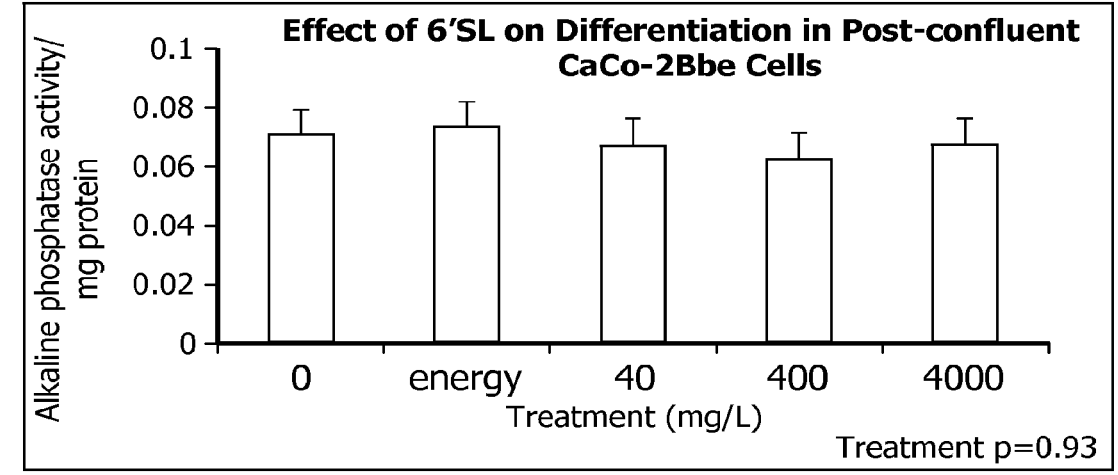
FIG. 16 is a graph showing Post-confluent CaCo-2Bbe epithelial cell differentiation in the presence of LNnT, 2'FL, and 6'SL.

In a second experiment, Caco-2 cells, which model more mature epithelial cells of the small intestine, were incubated in a humidified atmosphere of 5% carbon dioxide at 37° C. in the presence of LNnT or 2'FL at concentrations of 0 mg/L ("0"), 20 mg/L ("20"), 200 mg/L ("200"), and 2000 mg/L ("2000") or in the presence of 6'SL at concentrations of 0 mg/mL ("0"), 40 mg/mL ("40"), 400 mg/mL ("400"), and 4000 mg/mL ("4000") for 72 hours. The culture medium utilized was Dulbecco's Modified Eagle Medium (Life Technologies, Foster City Calif.) supplemented with 10% fetal calf serum and 2 mM glutamine The controls ("energy") consisted of 91.5 mg lactose and 64.2 mg N-acetyllactosamine/L for LNnT; 133 mg lactose and 67 mg fucose/L for 2'FL; and 195 mg lactose and 205 mg sialic acid/L for 6'SL. The impact of the LNnT, 2'FL, and 6'SL at various levels and the controls on the alkaline phosphatase activity is important for nutrient digestion, for breakdown of the harmful bacterial lipopolysaccharide molecules that induce inflammation, and is a marker of cell differentiation. For these reasons, intestinal tissue with greater alkaline phosphatase activity would be expected to be more resistant to inflammation and NEC. The results of the measurements are shown in FIGS. 14-16, which indicate that there is a trend toward increased alkaline phosphatase activity (and thus an increase in cell differentiation, digestive function, and protection against harmful effects of bacteria) in 2'FL treat cultures, a trend toward an increase in cells treated with LNnT, and no apparent effect on cells treated with 6' SL.

Figure 17:
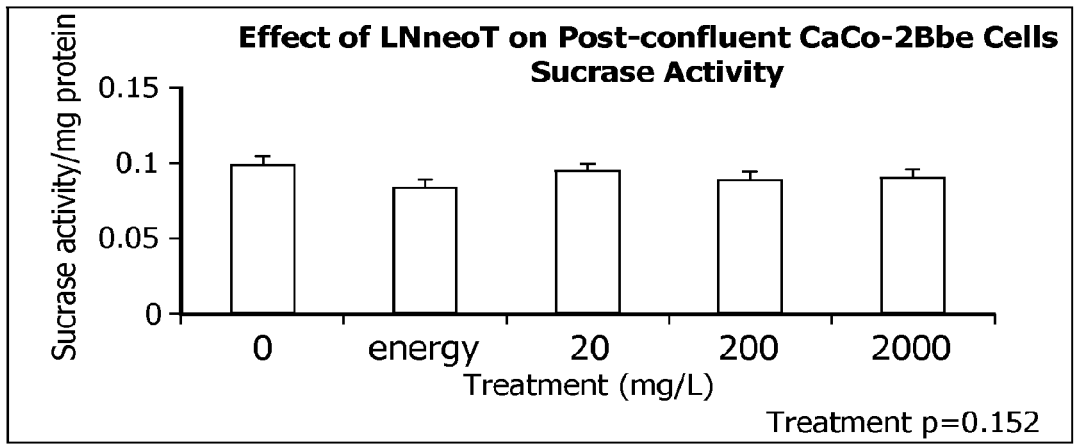
FIG. 17 is a graph showing Post-confluent CaCo-2Bbe epithelial cell sucrase activity in the presence of LNnT, 2'FL, and 6'SL.
Figure 18:
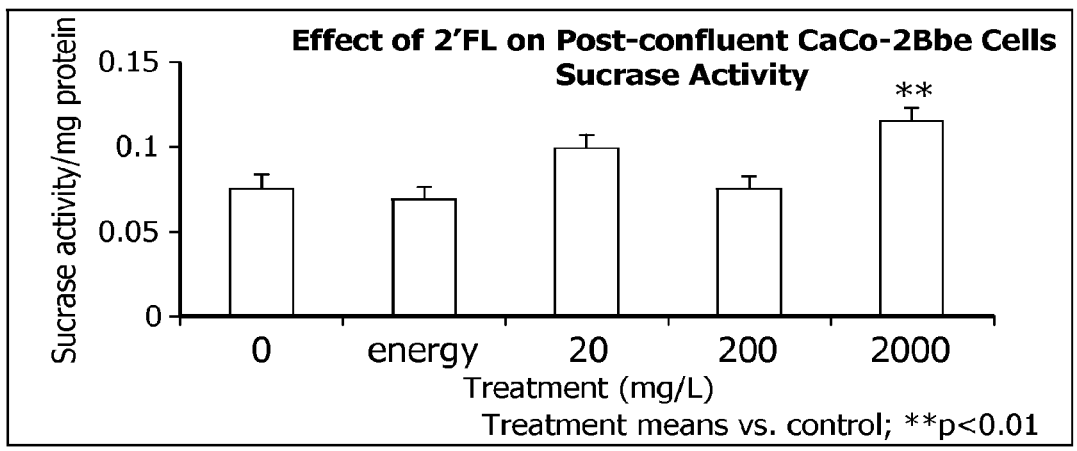
FIG. 18 is a graph showing Post-confluent CaCo-2Bbe epithelial cell sucrase activity in the presence of LNnT, 2'FL, and 6'SL.
Figure 19:
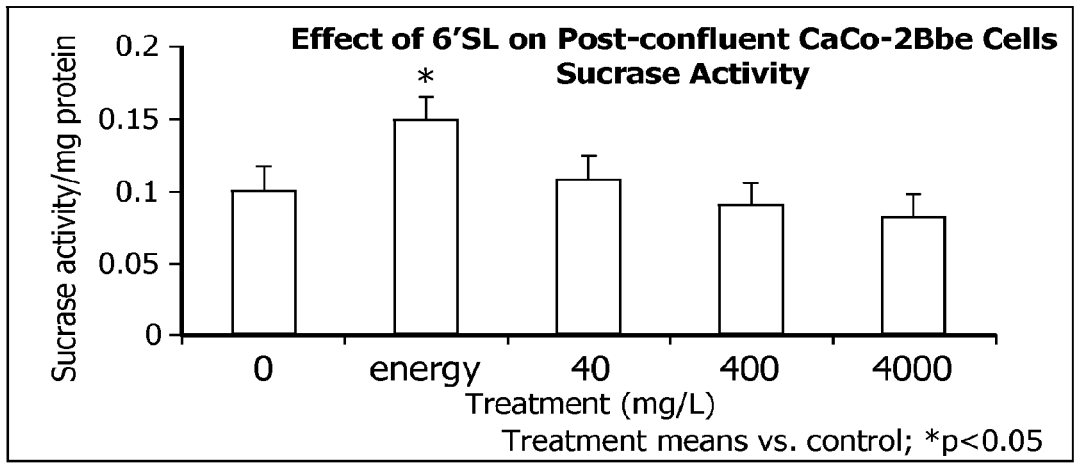
FIG. 19 is a graph showing Post-confluent CaCo-2Bbe epithelial cell sucrase activity in the presence of LNnT, 2'FL, and 6'SL.

The impact of LNnT, 2'FL, and 6'SL at various levels and the controls on the sucrase activity per milligram of protein for Caco-2 cells is measured as another indication of digestive function. The results of the measurements areshown in FIGS. 17-19, which indicate that there is a trend toward sucrase activity (and thus an increase in digestive function) in 2'FL treated cultures, and no apparent effect on cells treated with LNnT or 6'SL.

Figure 20:
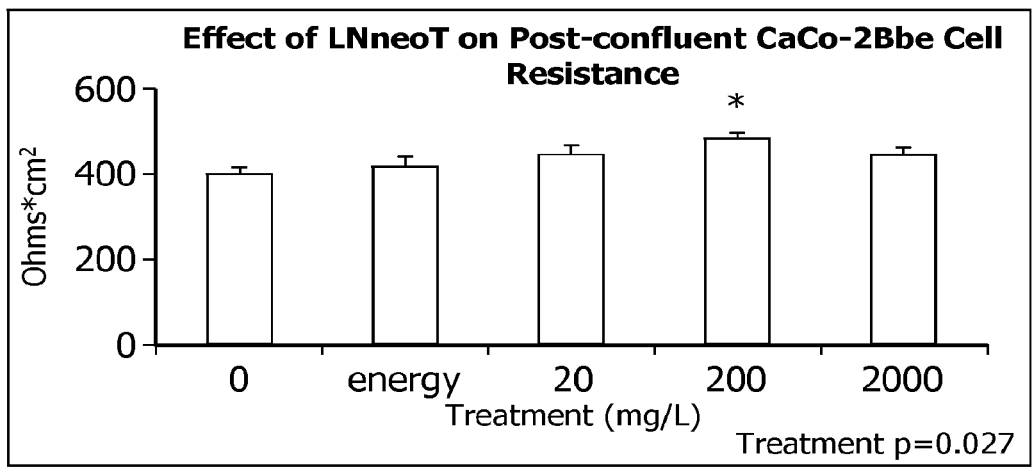
FIG. 20 is a graph showing Post-confluent CaCo-2Bbe epithelial cell resistance in the presence of LNnT, 2'FL, and 6'SL.
Figure 21:
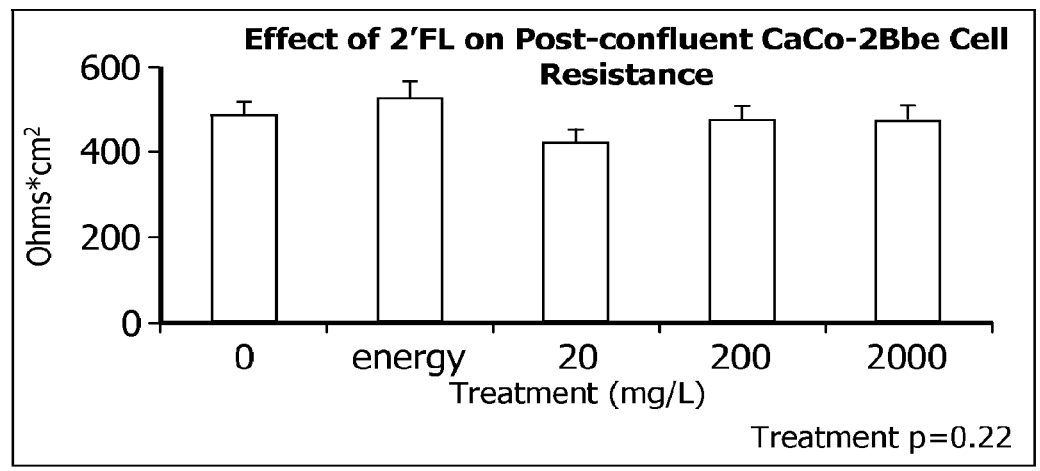
FIG. 21 is a graph showing Post-confluent CaCo-2Bbe epithelial cell resistance in the presence of LNnT, 2'FL, and 6'SL.
Figure 22:
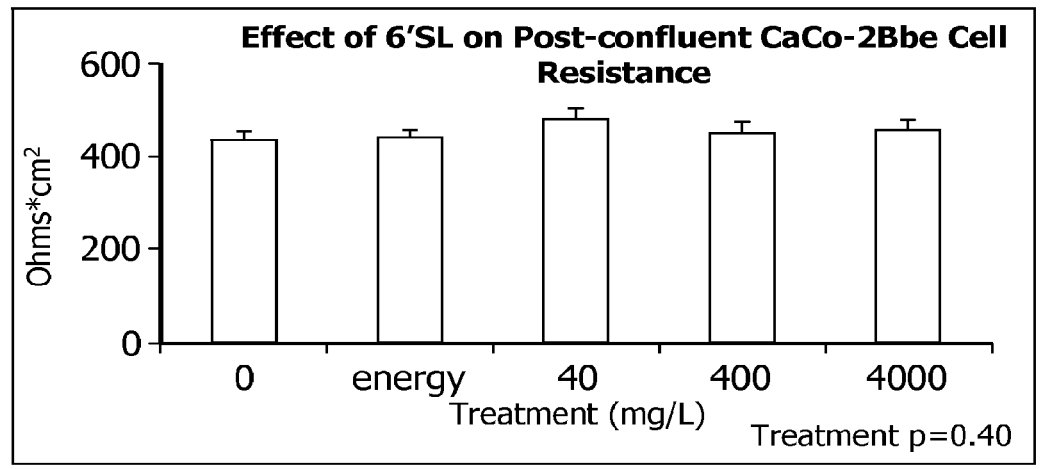
FIG. 22 is a graph showing Post-confluent CaCo-2Bbe epithelial cell resistance in the presence of LNnT, 2'FL, and 6'SL.

FIGS. 20-22 illustrate the effect of LNnT, 2'FL, and 6'SL on cell resistance (transepithelial resistance), which is a marker for epithelial barrier function, wherein a higher resistance is associated with a higher barrier function. Epithelial cell resistance or barrier function is a measure of differentiated epithelial cell function. Specifically, as the cells mature, tighter junctions between the cells are formed resulting in a stronger epithelial cell barrier. This barrier prevents the movement of large molecules, bacteria, or viruses from one side of the barrier to the other, which could improve resistance to infection, sepsis, and NEC. The results indicate that LNnT can have a positive effect on cell resistance for more mature Caco-2 cells. Transepithelial resistance was measured using Transwell Snapwell inserts containing the desired cell culture and were transferred to modified Ussing chambers and bathed in modified Kreb's solution at 37 C with 95% oxygen and 5% carbon dioxide. Transepithelial resistance was measured as the passive transport of ions across the monolayers.

Conclusions

The data reported in FIGS. 8-22 indicate that LNnT and 2'FL promote intestinal functions including digestion, barrier function, and protection against bacterial components that are known to induce inflammation. Promotion of digestive function, through increased digestive enzyme activities (sucrase and alkaline phosphatase) can help prevent or reduce the severity of feeding intolerance. Combined with effects on barrier function and protection against harmful bacterial metabolites, these data provide ample evidence that these HMOs could help protect against intestinal inflammation and NEC.

Example 39

In this Example, the effect of HMOs, and the dose-dependency thereof, on increasing the expression of TFF3 and other goblet cell genes that promotefeeding tolerance through enhanced gastrointestinal barrier function and healing by HMOs is analyzed.

Pooled HMOs are tested with respect to their ability to induce MUC2, TFF3, RELMβ, CHST5, and GAL3ST2 expression in the human LS174T cell culture model of goblet cells. The human LS174T colorectal cancer cell line is obtained from the American Type Culture Collection (ATCC). LS174T cells are maintained in minimum essential medium (MEM) supplemented with 10% Fetalplex (Gemini Biosciences), 1.5 g/L of $Na_2CO_3$, 10 ml/L penicillin G-streptomycin solution (Gemini Bio-products) at 37° C. in 5% $CO_2$. Pooled HMOs are obtained from Lars Bode (University of California, San Diego) and dissolved in cell culture grade water to required concentration. The solution is subsequently filter sterilized and used for cell culture studies. LS174T cells are treated with the media described above containing 0, 1, or 5 mg HMO/mL.

LS174T cells are collected and suspended in Trizol reagent and total RNA is isolated using the RNeasy Plus Kit (Qiagen) according to the manufacturer's instructions. The quality and quantity of RNA isolates are determined by Nanodrop (Thermo Fisher Scientific). RNA isolates are reverse transcribed using the High Capacity cDNA Reverse Transcription Kit (Applied Biosystems) to create cDNA, which is to assess gene expression via quantitative PCR.

For quantitative RT-PCR, specific TaqMAN gene expression assays are obtained from Applied Biosystems, which include expression assays for MUC2 (Hs00159374_m1), TFF3 (Hs00173625_m1), RELMβ (Hs00395669_m1), CHST5 (Hs00375495_m1), GAL3ST2 (Hs00223271_m1) and GUSB (Hs99999908_m1). Quantitative real-time PCR is performed using TaqMAN PCR Master Mix (Applied Biosystems). Reactions are run in duplicates in a 384-well plate using an Applied Biosystems 7900HT Fast Real-Time PCR System. The results are analyzed using SDS 2.3 software and calculated by delta delta Ct method. All samples are normalized to Gus-13 expression and fold induction is calculated over untreated controls. Gene expression is expressed as fold increase compared to HMO-free control cells. The experiment is repeated three times. Data represent means+ SEM (n=3 plates per experiment). Statistical differences are indicated by different letters ($P<0.05$).

Figure 23A:
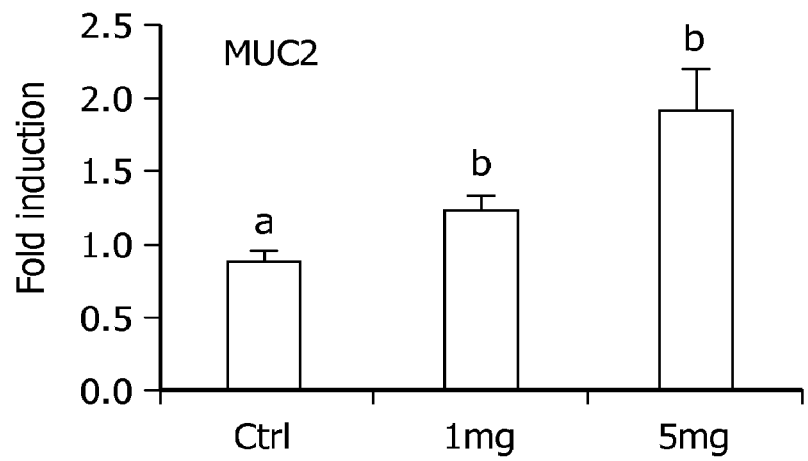
FIG. 23A is a chart depicting the effect of human milk oligosaccharides and dose dependency thereof on the expression of MUC2 as measured in Example 39.
Figure 23B:
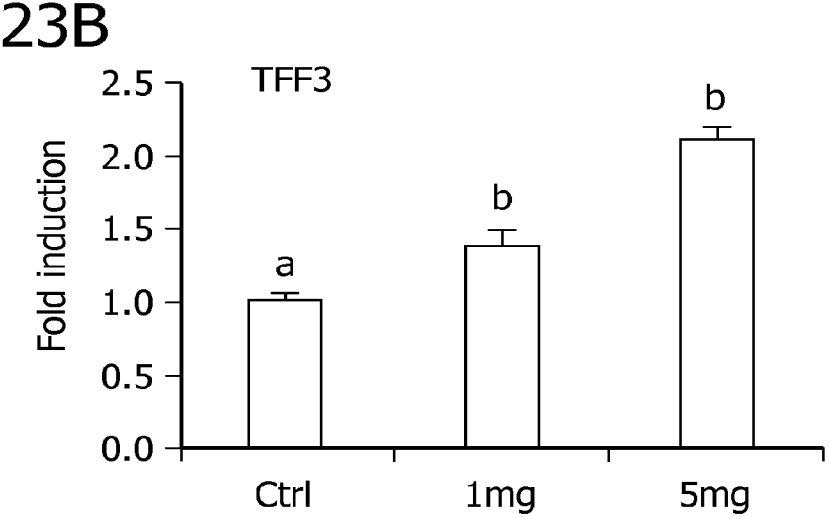
FIG. 23B is a chart depicting the effect of human milk oligosaccharides and dose dependency thereof on the expression of TFF3 as measured in Example 39.
Figure 23C:
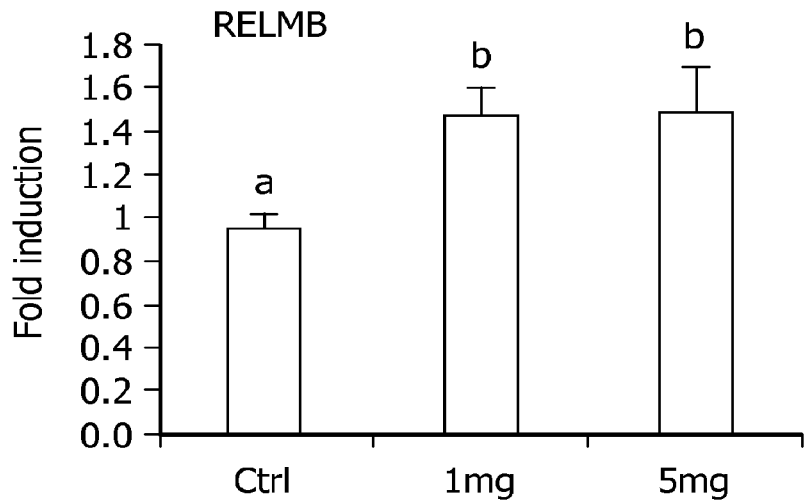
FIG. 23C is a chart depicting the effect of human milk oligosaccharides and dose dependency thereof on the expression of RELMβ as measured in Example 39.
Figure 23D:
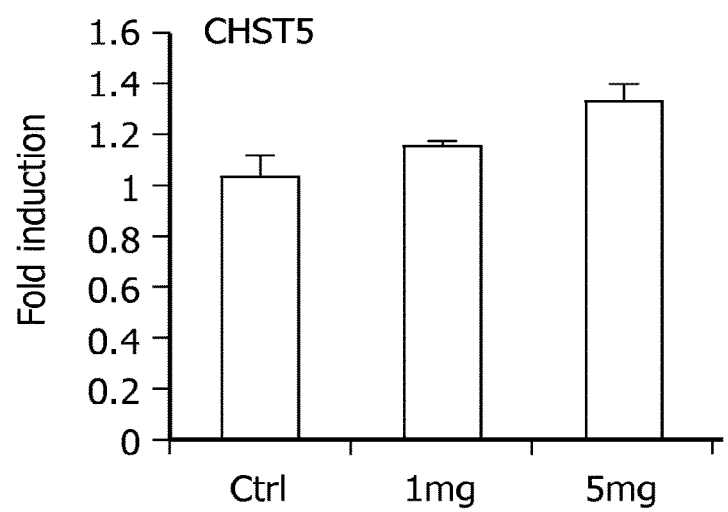
FIG. 23D is a chart depicting the effect of human milk oligosaccharides and dose dependency thereof on the expression of CHST5 as measured in Example 39.
Figure 23E:
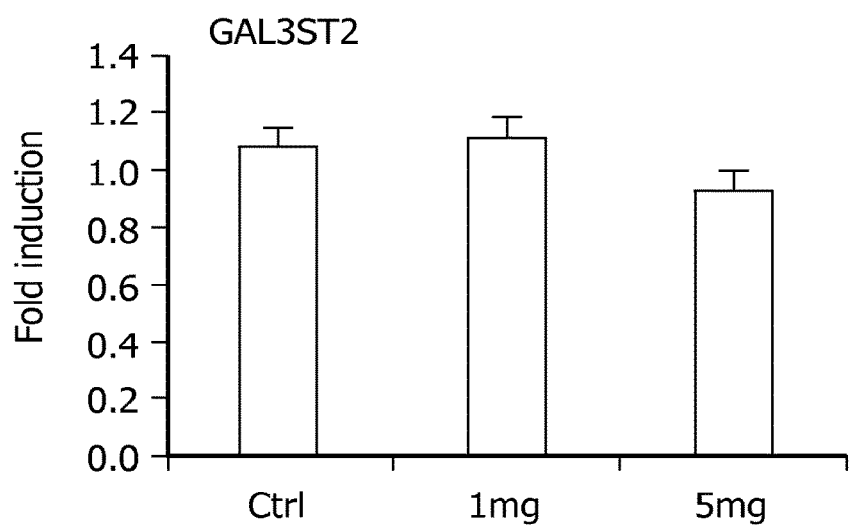
FIG. 23E is a chart depicting the effect of human milk oligosaccharides and dose dependency thereof on the expression of GAL3ST2 as measured in Example 39.

FIGS. 23A-23E represent the combined results of three replicate experiments. Specifically, FIGS. 23A, 23B, and 23C illustrate that the treatment with HMOs at a level of at least 1 mg/mL increases the expression of the MUC2, TFF3, and RELMβ genes compared to control cultures. Increased expression of goblet cell genes is specific and not universal, as evidenced by the minimal induction or lack of induction of CHST5 and GAL3ST2, respectively, by treatment with HMOs at either 1 mg/mL or 5 mg/mL.

In addition, FIGS. 23A and 23B indicate a dose dependent increase in expression of MUC2 and TFF3, with a modest induction (~1.5 fold) noted at the 1 mg/mL treatment level and more pronounced increases (~2 fold) at 5 mg/mL. In addition, the expression levels of RELMβ (FIG. 23C) were increased (~1.5 fold) at each of the 1 mg/mL treatment level and the 5 mg/mL treatment level. In contrast, gene expression of CHST5 (FIG. 23D) and GAL3ST2 (FIG. 23E) is not significantly impacted at any dose. As such, it can be concluded that the impact of HMOs on expression of several genes involved in the healing response of the gastrointestinal tract is dose-dependent.

These results indicate that HMOs promote the expression of several genes involved in GI barrier function and in the healing response of the GI tract. First, the protein products of the MUC2, TFF3, and RELMβ genes, each of which was induced by HMOs, work synergistically to create the mucus barrier that protects the GI tract from pathogens. Also, expression of TFF3 has been positively associated with prevention and restitution of gastrointestinal damage to the epithelial cells in the intestine of mammals. Oral treatment with TFF3 reduces the damage associated with different forms of colitis in animal models. Additionally, HMOs induce the expression of MUC2, which provides a barrier that protects the gastrointestinal tract from infection and other sources of injury. Further, HMOs induce the expression of RELMβ, which is a protein associated with resolution of inflammation. Because tissue damage is difficult to heal when inflammation is abundant, the inflammation resolving effects of RELMβ induced by HMOs also supports healing. The combinedimpact of HMOs on expression of TFF3, MUC2, and RELMβ enables a product to prevent necrotizing enterocolitis and support wound healing through its synergistic effects on cell healing, resolution of inflammation and promotion of barrier function.

What is claimed is:

1. A method of improving the feeding tolerance of an infant, toddler, or child, the method comprising administering to an infant, toddler, or child in need thereof a nutritional composition comprising at least one human milk oligosaccharide selected from the group consisting of 2'-fucosyllactose, lacto-N-neotetraose, and combinations thereof in a total amount of from about 0.001 mg/mL to about 20 mg/mL.

2. The method of claim 1, wherein the composition comprises from 0.001 mg/mL to less than 2 mg/mL of 2'-fucosyllactose.

3. The method of claim 1, wherein the composition comprises from 0.001 mg/mL to less than 0.2 mg/mL of lacto-N-neotetraose.

4. The method of claim 1, wherein the at least one human milk oligosaccharide is present in a total amount of from about 0.001 mg/mL to less than 2 mg/mL.

5. The method of claim 1, wherein the nutritional composition further comprises at least one of a probiotic, a long chain polyunsaturated fatty acid, an antioxidant, a milk protein of human origin, and a milk protein of bovine origin.

6. The method of claim 1, wherein the nutritional composition further comprises at least one of 3'-sialyllactose, 6'-sialyllactose, and combinations thereof.

7. The method of claim 1, wherein the nutritional composition further comprises at least one of inulin, a gum, polydextrose, and combinations thereof.

8. A method of improving the feeding tolerance of an infant, toddler, or child, the method comprising administering to an infant, toddler, or child in need thereof a nutritional composition comprising 2'-fucosyllactose and 6'-sialyllactose, wherein the 2'-fucosyllactose and 6'-sialyllactose are present in a total amount of from about 0.001 mg/mL to about 20 mg/mL.

9. The method of claim 8, wherein the nutritional composition further comprises a fructooligosaccharide.

10. The method of claim 9, wherein the fructooligosaccharide is present in an amount of about 0.001 mg/mL to about 20 mg/mL.

11. The method of claim 10, wherein the nutritional composition comprises from 0.001 mg/mL to less than 0.25 mg/mL of 6'-sialyllactose.

12. The method of claim 11, wherein the nutritional composition comprises from greater than 0.4 mg/mL to 10 mg/mL of 6'-sialyllactose.

13. The method of claim 10, wherein the nutritional composition comprises from 0.001 mg/mL to less than 2 mg/mL of 2'-fucosyllactose.

14. The method of claim 10, wherein the nutritional composition further comprises at least one of a probiotic, a long chain polyunsaturated fatty acid, an antioxidant, a milk protein of human origin, a milk protein of bovine origin, and a milk protein of combined bovine and human origin.

15. The method of claim 14, wherein the nutritional composition further comprises at least one of inulin, a gum, polydextrose, and combinations thereof.

16. A shelf stable synthetic formula for improving the feeding tolerance of an infant, toddler, or child, the synthetic formula comprising from about 0.001 mg/mL to about 20 mg/mL of an oligosaccharide blend, wherein the oligosaccharide blend comprises a first oligosaccharide, 2'-fucosyllactose, in a concentration of from 0.001 mg/mL to less than 2.0 mg/mL, and a second oligosaccharide, 6'-sialyllactose, in a concentration of from 0.001 mg/mL to less than 0.25 mg/mL.

17. The synthetic formula of claim 16, further comprising a fructooligosaccharide.

18. The synthetic formula of claim 16, further comprising a third oligosaccharide selected from the group consisting of inulin, a gum, polydextrose, and combinations thereof.

19. The synthetic formula of claim 16, wherein the oligosaccharide blend does not comprise human milk oligosaccharides other than 2'-fucosyllactose and 6'-sialyllactose.

* * * * *